United States Patent [19]
Muller et al.

[11] Patent Number: 5,273,905
[45] Date of Patent: Dec. 28, 1993

[54] PROCESSING OF SLIDE MOUNTED MATERIAL

[75] Inventors: Uwe R. Muller, Kendall County; Lawrence J. Mika; Donald J. Lindley, both of Naperville; Ernest J. Wisner, Elgin, all of Ill.

[73] Assignee: Amoco Corporation, Chicago, Ill.

[21] Appl. No.: 660,718

[22] Filed: Feb. 22, 1991

[51] Int. Cl.⁵ .............. C12M 1/20; G01N 21/00; G01N 31/00; G01N 33/00
[52] U.S. Cl. .................... 435/301; 435/287; 422/63; 422/67; 422/99; 422/100
[58] Field of Search ........... 435/284, 290, 299, 301, 435/294, 310, 970, 287; 422/63, 67, 99, 100

[56] References Cited

U.S. PATENT DOCUMENTS

| | | | |
|---|---|---|---|
| 3,764,215 | 10/1973 | Wallach | 356/36 |
| 3,837,795 | 9/1974 | Becker et al. | 8/3 |
| 4,039,247 | 8/1977 | Lawman et al. | 435/300 |
| 4,110,167 | 8/1978 | Melnyk | 435/293 |
| 4,141,312 | 2/1979 | Louder et al. | 118/7 |
| 4,296,069 | 10/1981 | Smith et al. | 422/64 |
| 4,731,335 | 3/1988 | Brigati | 436/180 |
| 4,847,208 | 7/1989 | Bogen | 436/174 |
| 4,859,419 | 8/1989 | Marks et al. | 422/56 |
| 4,908,319 | 3/1990 | Smyczek et al. | 435/285 |
| 4,948,728 | 8/1990 | Stephanopoulos et al. | 435/41 |
| 5,021,218 | 1/1991 | Davis et al. | 422/104 |
| 5,073,504 | 12/1991 | Bogen | 436/174 |
| 5,075,079 | 12/1991 | Kerr et al. | 422/64 |
| 5,080,869 | 1/1992 | McCormick | 422/102 |

Primary Examiner—James C. Housel
Assistant Examiner—N. Bhat
Attorney, Agent, or Firm—William E. Murray

[57] ABSTRACT

An apparatus for the sequential multi-step processing of slide surface portions. The apparatus includes subassemblies and assemblies and a computer driven control system therefor. The apparatus permits at least one step of such a process sequence to be carried out with minimal amounts of processing liquids which is advantageous for specimen treatment with costly reagents, such as aqueous compositions containing probes. Immunochemical and in situ hybridization procedures can be carried out.

20 Claims, 21 Drawing Sheets

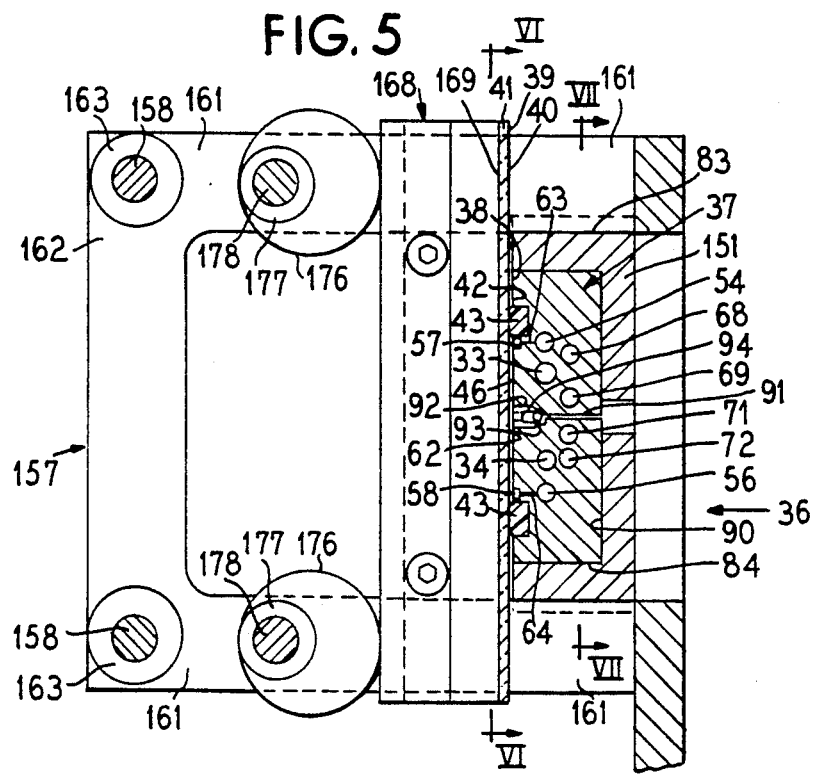
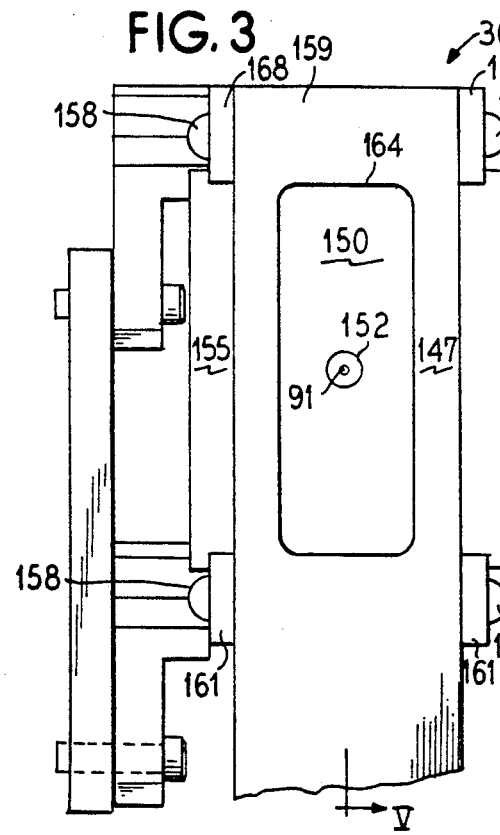
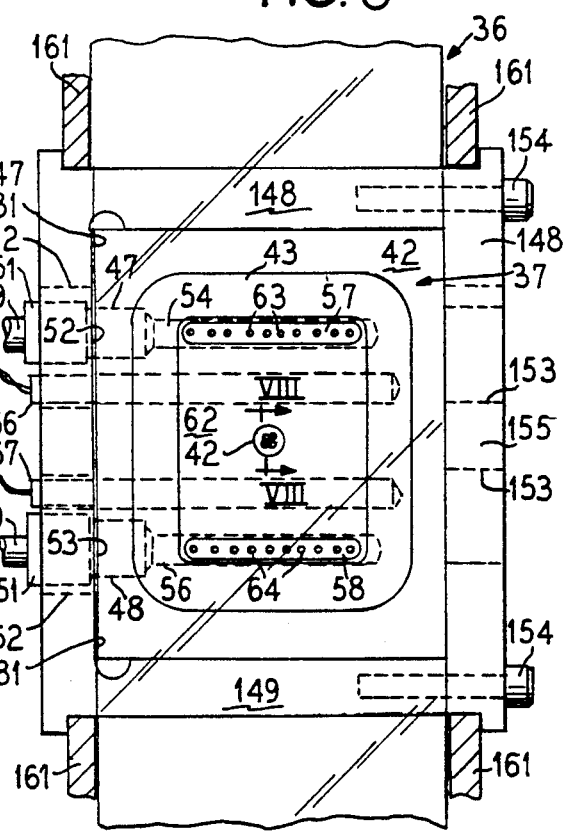

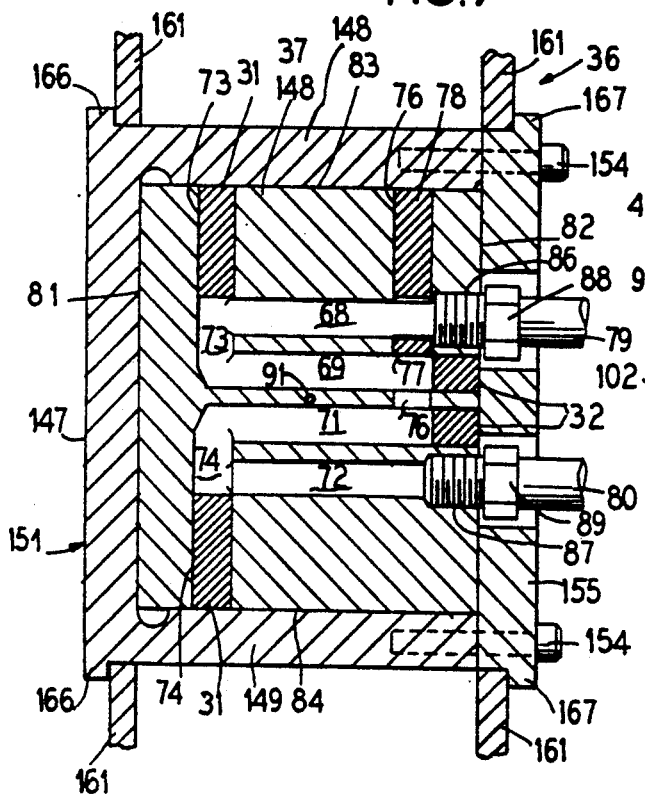
FIG. 7
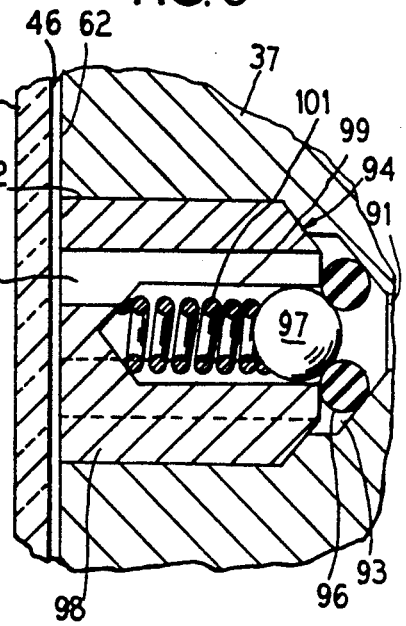
FIG. 8
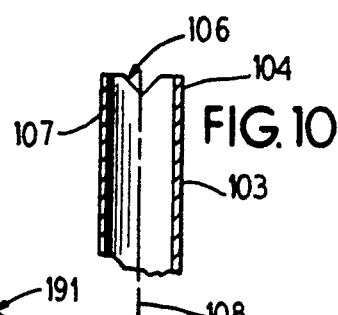
FIG. 9
FIG. 10
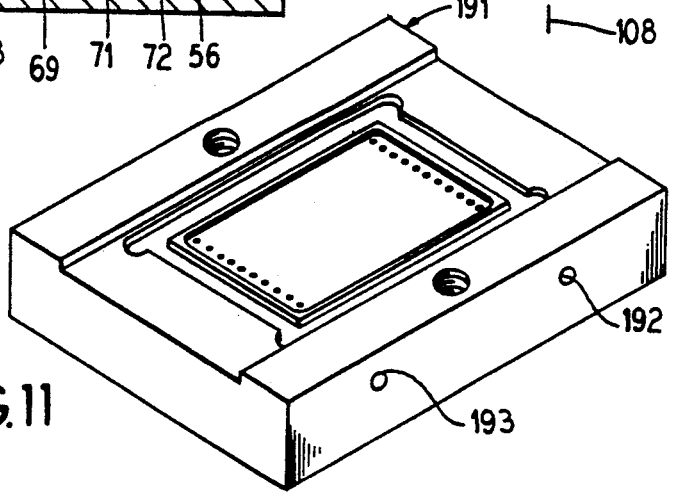
FIG. 11

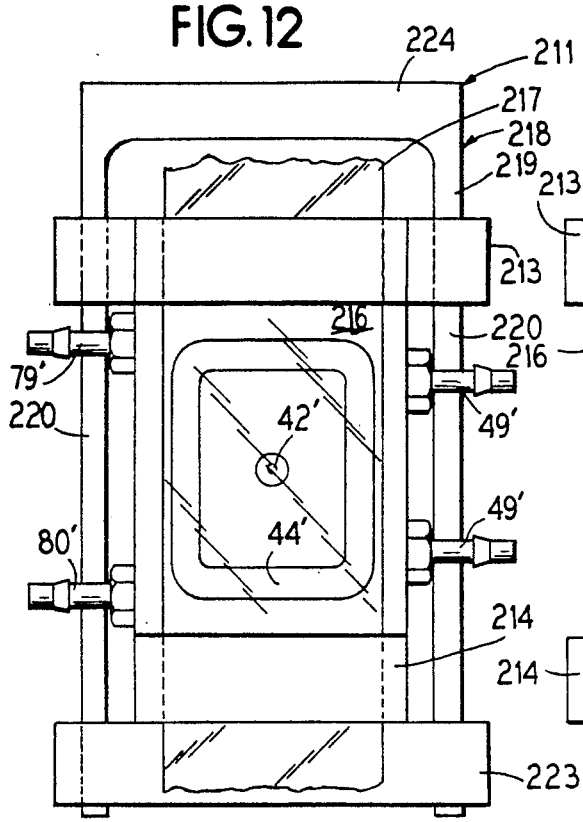
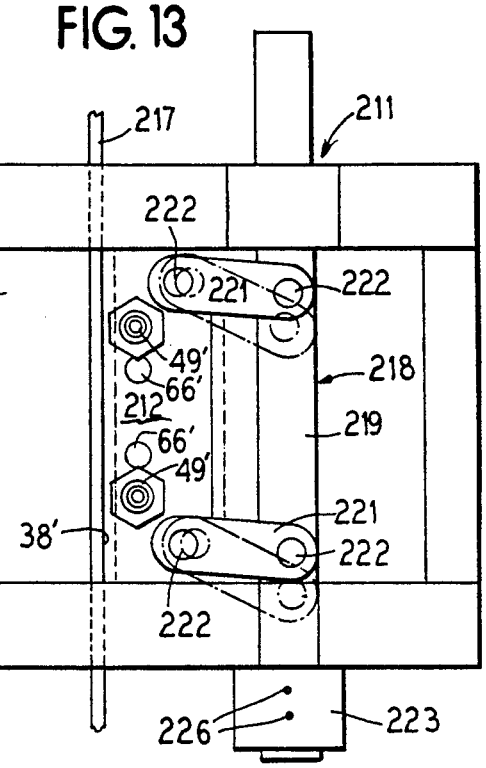
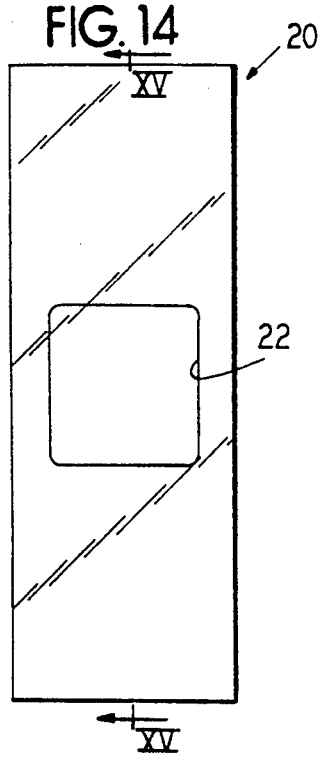
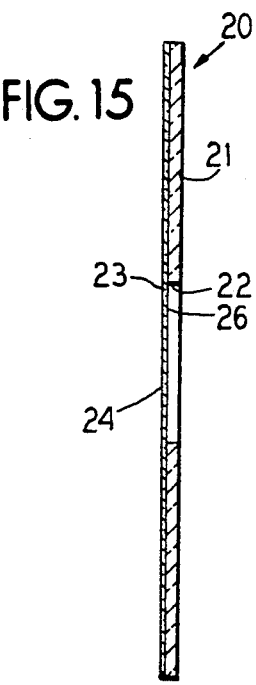
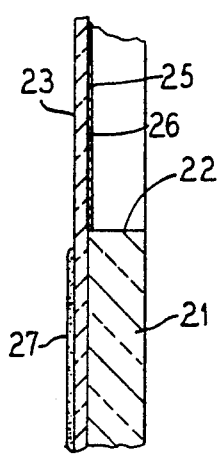

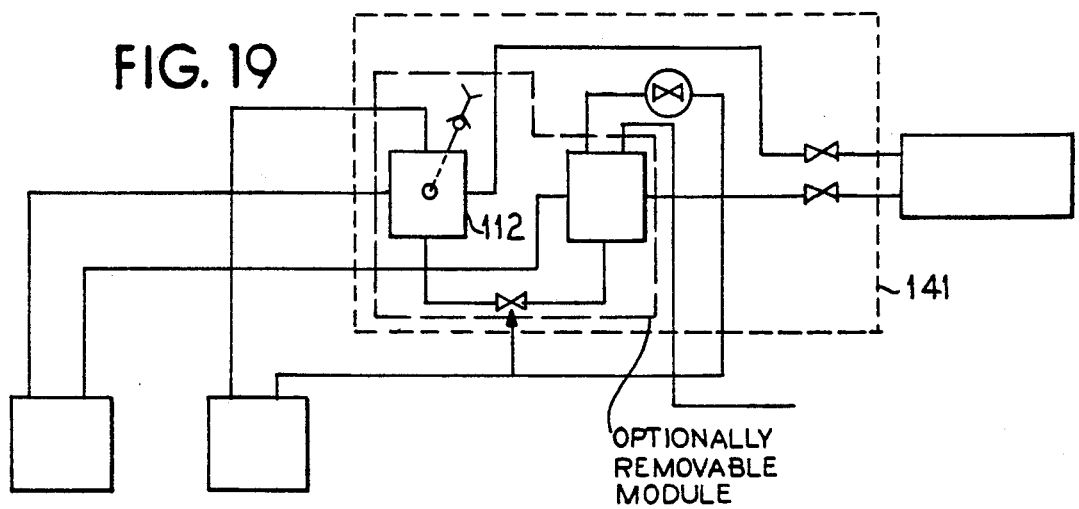
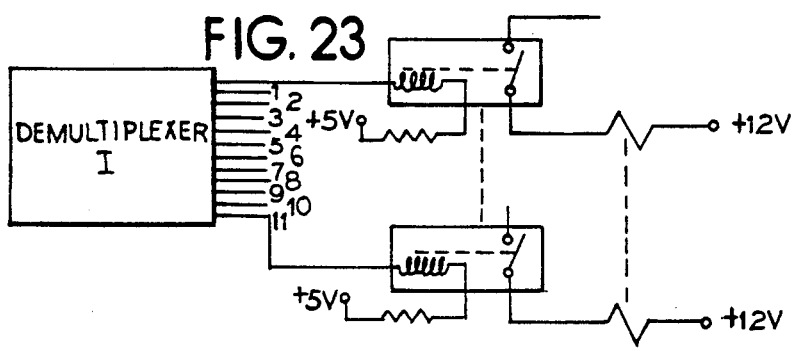
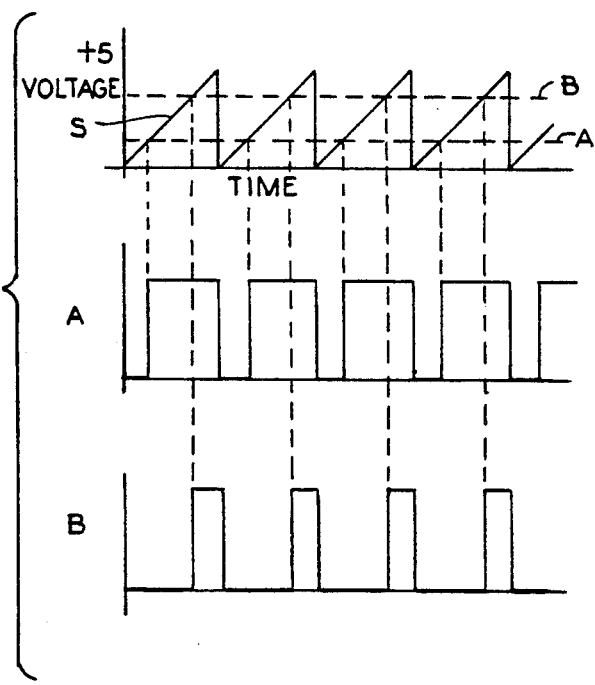

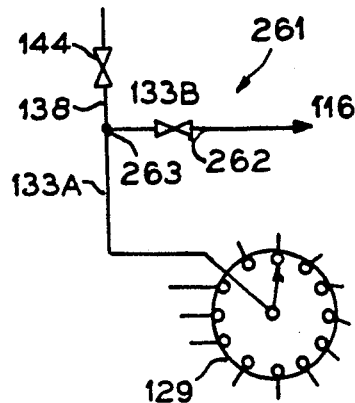
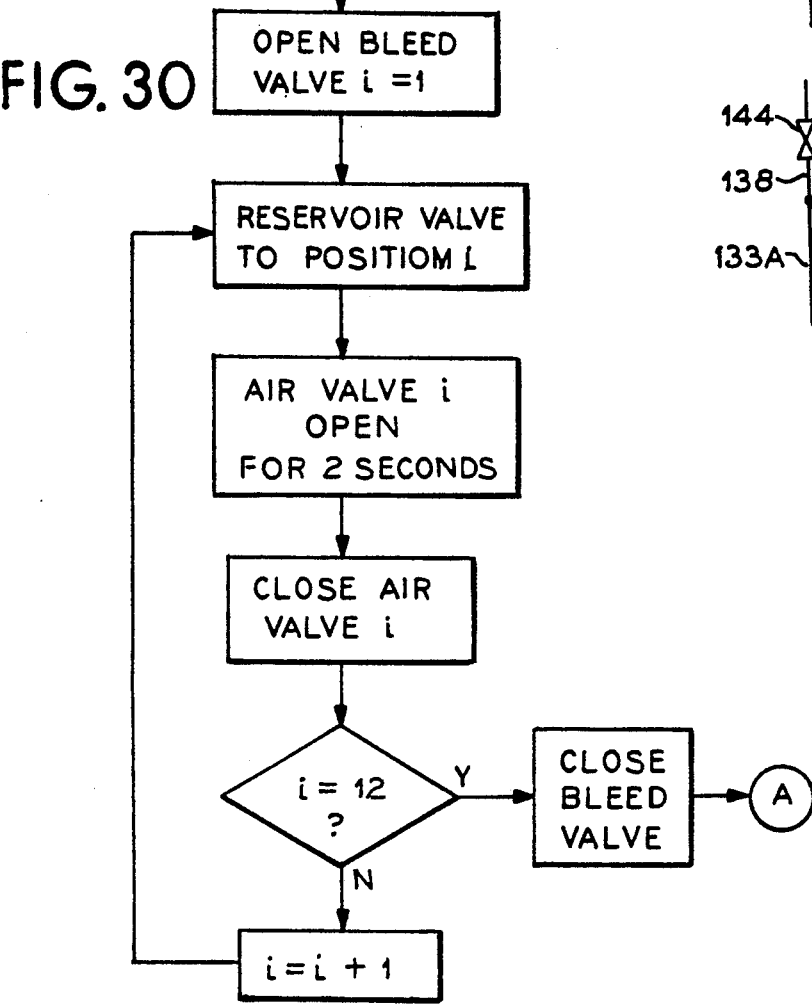
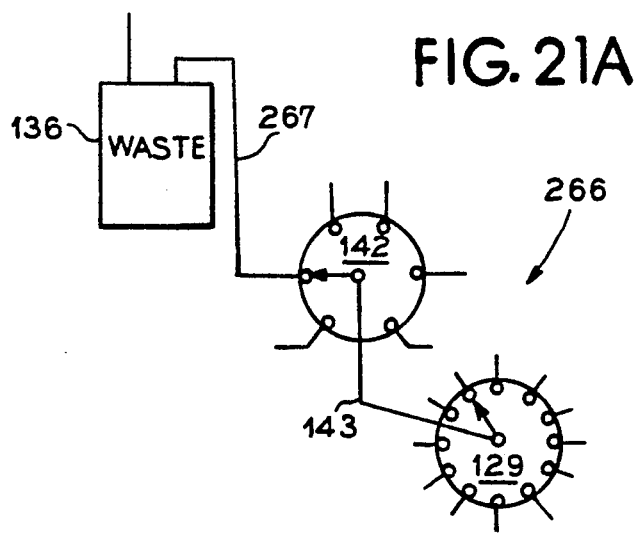

PROCESSING OF SLIDE MOUNTED MATERIAL

FIELD OF THE INVENTION

This invention relates to apparatus and methods for the sequential, multi-step, controlled processing of slide surface mounted material, particularly biological material, such apparatus and methods being particularly adapted for utilization with programmed, controlled, fluid-contacting steps and with minimizable fluid quantities.

BACKGROUND OF THE INVENTION

The sequential, step-wise processing of slide surface mounted biological material is known and used in various procedures. Some of such procedures have come into widespread common usage for analytical and diagnostic purposes in various biological disciplines including biotechnology, biochemistry, molecular biology, molecular genetics, cytogenetics, cell biology, pharmacology, immunology, and the like. Such procedures are commonly carried out with each one of a series of processing steps involving the contacting of such mounted material with a variety of fluids (liquid and/or gases). Unless the particular processing step sequence is properly carried out, the results desired are not obtained. The total number of such processing steps used in any given procedural embodiment can vary, depending upon many variables.

Examples of such procedures include staining of tissue, cell, and cell-derived material, such as immunohistochemical staining of slide mounted biological tissue, and the like; hybridization of slide-bound nucleic acids with labeled probes that incorporate complementary nucleotide sequences, such as in situ hybridization; and the like.

In, for example, the staining of slide mounted specimens of biological materials, the prepared slides may be dipped successively into individual ones of a series of small vessels or jars, each about 0.2 to about 2 liters in volumetric capacity, and each containing a particular liquid treating composition, such as washing agents, buffers, denaturation agents, dehydrating agents, dyes and the like. One or more dye materials may be used to highlight different cells, structures of cells, intracellular structures, cellular products or the like. Resulting dyed slides may be washed and dried, possibly stored, and then microscopically examined. Selective staining procedures using specific antibody or gene probes have been developed and are advantageously highly specific and sensitive. However, such procedures require many successive steps to be carried out.

In, for another example, in situ hybridization, the presence, location, identity, or quantity of a particular nucleic acid type in a given cell structure is determined. Starting cytological preparations mounted on glass slides may be variously treated. For instance, one step may involve a treatment to denature the DNA or RNA (without losing the identity of the cellular nucleic acid structures). Thereafter, the resulting slide may be contacted with a liquid composition containing an oligonucleotide probe which is labeled with an appropriate radioisotope, fluorophore, enzyme, hapten, avidin, or the like. Hybridization occurs between the probe and the complementary nucleic acid, such as a gene on a chromosome, a ribosomal RNA (rRNA), or the like. The resulting slide is suitably washed to remove residual probes Subsequent other further procedural processing steps may also be undertaken. The resulting slide is examined using an evaluation procedure such as, for example, microscopy, autoradiography, fluorescence measurement, photon emission, or the like. Up to about 30 or more controlled step sequences may be involved for a single hybridization procedure.

Since multi-step processing of slide mounted biological materials typically involves a multiplicity of slides, a plurality of process liquids, and a plurality of step conditions, control problems arise in achieving identical treatment of all slides of a slide plurality which are all undergoing the same processing sequence An added complication is that some processing liquids are very costly and must be used sparingly, such as liquids containing nucleotide probes. Such liquids are employed under conditions which differ from the conditions employed in other steps in the processing sequence Such make sequential problems multi-step processing techniques difficult to carry out identically for a plurality of slides.

There is a need in the art for apparatus and methods which can be operated and practiced so as to carry out a given multi-step slide processing sequence in a replicable manner. All variables affecting a slide surface during each individual step of the sequence need to be controlled, including temperature, time, and the fluid contacting variables, such as reagent concentration, fluid flow rate, slide surface residence time, and the like. Typically, it is desired that all slides of a group thereof should receive substantially identical processing whether or not individual slides of such group are processed parallel to one another in a given procedure or are in series relationship to one another in successive procedures Further, there is a need in the art for apparatus and methods which permit such a controlled step sequence to be automatically carried out under preliminarily programmed conditions. Still further, there is a need in the art for such apparatus and methods which can be practiced, if desired, with minimum amounts of processing fluids and agents particularly with regard to probes.

So far as is now known, apparatus and methods with such capability have not previously been known to the art.

SUMMARY OF THE INVENTION

This invention relates to apparatus and methods for the sequential, multi-step, controlled processing of slide surface mounted material, or the like.

In one aspect, this invention provides apparatus and methods for accomplishing a sequence of such processing steps while regulating the processing conditions employed in each of the steps. The apparatus and methods can be used with individual slides or a slide plurality. The slides can be processed in a serial manner or a parallel manner.

In another aspect, this invention provides such step sequencing apparatus and methods wherein the individual fluid flows employed in each sequenced processing step at one or more processing stations are controllably variable by means of a pulsed gas flow with such pulses being regulatable. This provides for efficient, reliable operation and minimizes the need for subcomponents which would otherwise be needed to achieve the same result by alternative means and/or techniques.

In another aspect, this invention provides automatic apparatus and methods for the computerized control and programmable operation of such step sequencing apparatus and methods. In one presently preferred operational mode using such computerized control and programmed operation, the step sequencing apparatus and methods are operator prechosen to follow a predetermined programmed sequence. In another presently preferred operational mode, a preset computer program is employed for operation of the step sequencing apparatus and methods, but the program is operator-interactive so that selected choices concerning particular apparatus modes and operational conditions can be made and/or varied by the operator either on-line or off-line. In another presently preferred operational mode, a combination of computer program and operator manual control is employed wherein an operator controls certain operational capabilities so that, if desired, the operator manually carries out one or more steps, or parts of steps, in a processing sequence. For example, the step of injecting of a probe-containing liquid into a particular processing station at a given time or in a given sequence and then selecting the duration (time) and temperature of the subsequent incubation step, or the like, can be operator controlled.

In another aspect, this invention provides such apparatus and methods that can be utilized, if desired, with one or more slides being simultaneously processed in a sequential manner, each slide being associated with a different processing station. The individual slide at each station when a slide plurality is being processed can be, if desired, identically or variously processed relative to other slides. For example, all slides of such plurality can undergo the same step-wise processing sequence at the same time, or the slides of such plurality can each be undergoing a processing sequence which is different from the processing sequences which others of such slide plurality are undergoing. In the alternative, the slides of such plurality can each be undergoing the same processing sequence, but at varying start times, or at variously selected conditions, or combinations thereof, or otherwise, as desired, depending upon the particular equipment used, the computer programming selected, the slide processing objectives, and the like.

In another aspect, this invention provides apparatus and methods which enable achievement of such slide surface processing with minimal amounts of processing fluids. Thus, the individual slide processing stations, and the cooperating, functionally associated apparatus elements, are preferably structured so that such a processing step sequence is achievable using small amounts of processing fluids while individual station temperature and fluid flow are each regulatable.

Also, the individual slide processing stations are preferably structured so that, during such a processing sequence, the total fluid put through a station chamber, the chamber fluid volume, the fluid residence time in a chamber, and the like is/are regulatable. For example, for at least one processing step of a sequence step plurality, the amount of liquid employed for slide surface contacting is reduced and minimized relative to the respective amounts of liquid employed in others of such steps of the processing sequence. For another example, the processing station chamber volume is reduced during at least one such fluid contacting step down to a volume which appears to be at a theoretical and practical limit for a slide contacting chamber and which volume is optionally at least about an order of magnitude smaller than the same chamber's volume that is used in at least one other fluid contacting step of a particular processing sequence. A slide contacting station with a chamber having such a small and variable volume has apparently not previously been known.

In another aspect, this invention provides a class of slide surface processing stations each of which is (a) individually both temperature controllable and chamber volume controllable, (b) utilizes relatively small volumes of treating fluids, (c) provides a flow pathway over slide surface portions which is laminar or approximately so, and (d) can be used for the entire step sequence of a multiple processing step procedure involving the surface portions of a single slide.

For example, one presently preferred such processing station is characterized by a capacity to undergo a controlled and, if desired, continuous or incremental chamber volume change; for example, the individual station chamber volume can range from about 500 $\mu$l (microliters) or greater down to about 10 $\mu$l or less, if desired. In one presently preferred operational mode, two stages of individual station chamber volume are utilized, with one chamber volume being, for instance, about 200 $\mu$l which is used for all steps of a processing sequence except for at least one and a second chamber volume being, for instance, about 10 $\mu$l which is used for such other steps of such sequence.

In another aspect, apparatus of this invention is provided with modular-type subassemblies, particularly processing station subassemblies. Thus, such a processing station module contains in combination a temperature regulated, slide processing chamber block assembly having a gasket-equipped, slide contacting chamber with input and output fluid passageways, a temperature regulated processing fluid delivery reservoir, interconnecting conduit means associating such reservoir with such chamber, adjustable pressurizing valve means for regulating the flow rate of fluid transported from such delivery reservoir to such chamber block. If desired, all or a portion of the components of such a processing station module may be formed into a separately insertable and removable station module unit which is preferably provided with suitable quick connect/disconnect terminal connectors for electrical control and fluidic supply. Such modules in apparatus embodiments of the invention not only achieve cost advantages in apparatus construction and maintenance, but also permit various operational and equipment configurations to be achieved and operated in a simple and reliable manner. Thus, the inventive apparatus and methods enhance economics and usage of various sequential multi-step processing procedures, as desired.

In another aspect, the present invention provides a computer based control system for carrying out sequential, multi-step, fluidic processing of material at one or more processing stations using (a) a plurality of processing fluids each initially being in a respective regulatable reservoir, (b) multiple position switching valve means, and (c) regulatable pumping valve means. Processing station temperature control can also be achieved. The system utilizes a computer-produced analog signal and multiplexed binary digital signals for control purposes, and peripheral means functionally associated with individual regulatable components of the processing apparatus so that such computer generated control signals are converted into regulating command signals for operating such regulatable components. The control system is well adapted for use with relatively small amounts of processing material and processing fluids.

In another aspect, this invention provides an improved process for accomplishing the sequential, multi-step, controlled processing of slide surface mounted material involving the steps of: (a) selecting a computer program for slide surface sequential step processing which program commands usage of particular sequencing and step conditions during each sequential step of such a processing, (b) positioning a slide having a surface portion with mounted material thereon at a slide processing chamber, the chamber being in operative functional association with temperature regulating means and with regulatable fluid transporting means for regulating fluids passed sequentially through the chamber over the surface portion, and (c) associating the program with the temperature regulating means and with the regulatable fluid transporting means (including valves, conduits, and the like) so that the program is executed relative to the slide surface.

In another aspect, this invention provides automatic processes for accomplishing staining of slide surface mounted material under controlled conditions. Such a process comprises of least two preliminary steps of slide surface fluidic treatment, at least one step of staining, and at least two terminal steps of slide surface fluidic treatment. Such process is carried out with the involved slide being positioned so as to constitute one wall portion of a relatively small slide surface processing chamber which preferably has a volume that is not more than about 500 $\mu$l.

In another aspect, this invention provides automatic processes for accomplishing hybridization of slide surface mounted cytological material containing nucleic acids under controlled conditions. Such a process comprises at least two preliminary steps of slide surface fluidic treatment, at least one step of hybridizing probe exposure, and at least two terminal steps of slide surface fluidic treatment. Such process is carried out with the involved slide being positioned so as to constitute one wall portion of a relatively small slide surface processing chamber which preferably has a volume that is not more than about 500 $\mu$l.

An outstanding feature of this invention is that slide surface processing is accomplished using minimal amounts of processing fluids by either flow or injection procedures. Expensive processing liquids, for example, can be injected in minimal amounts. Also, usage of individual slide processing stations permits each slide to receive identical processing liquids that are uncontaminated by materials from other slides.

Other and further embodiments, features, purposes, advantages, objects, aims, applications, uses, and the like will be apparent to those skilled in the art from the present teachings taken with the accompanying drawings and the appended claims.

BRIEF DESCRIPTION OF THE DRAWINGS

In the drawings:

FIG. 3 is an end elevational view of the block assembly shown in FIG. 2;

FIG. 5 is a cross-sectional view taken along the line V—V of FIG. 3 with some parts thereof removed;

FIG. 6 is a cross-sectional view taken along the line VI—VI of FIG. 5;

FIG. 7 is a cross-sectional view taken along the line VII—VII of FIG. 5;

FIG. 8 is a fragmentary cross-sectional view taken along the line VIII—VIII of FIG. 6;

FIG. 9 is a cross-sectional view through the chamber block structure with the gasket in place taken along the line IX—IX of FIG. 6;

FIG. 10 is a greatly enlarged side elevational view of one embodiment of a hypodermic needle tip region structure adapted for use with the slide processing station of FIGS. 2-9;

FIG. 11 is perspective view of an alternative chamber block structure adapted for use in the processing station shown in FIGS. 2-9;

FIG. 12 an end elevational view of another embodiment of a slide processing chamber block assembly employable in apparatus such as shown in FIG. 1 which block assembly is equipped with a toggle-type slide holding means;

FIG. 13 is a side elevational view of the assembly shown in FIG. 12;

FIG. 14 is a plan view of one embodiment of a slide structure adapted for use in the practice of the present invention;

FIG. 15 is transverse sectional view taken along the line XV—XV of FIG. 14;

FIG. 15A is an enlarged fragmentary detailed section of a mid region of the view shown in FIG. 15;

FIG. 19 is a schematic view of a single slide processing station module comprised of a chamber block assembly and a delivery reservoir which module is employable in sequential multi-step processing apparatus of this invention;

FIG. 20A is a fragmentary view of apparaties as shown in FIG. 20, but showing an alternative arrangement of components in the region of the multiport distribution valve;

FIG. 21A is a fragmentary view of apparatus as shown in FIG. 21, but showing an alternative arrangement of components in the region of the two multiport distribution valves;

FIG. 23 is a schematic-type diagram of one embodiment of computer controlled electrical means for opening and closing the fluid supply valves employed in the apparatus of FIGS. 20-22;

FIG. 24 is a graphical presentation illustrating conversion of a saw-tooth wave form into voltage pulses whose duration and frequency are controllably variable, thereby permitting individual processing station module valves that are responsive to pulse width modulation to operate and produce different fluid flow rates;

FIG. 30 is a flow diagram of one embodiment of a computer program step sequence employable in the program of FIG. 28 for accomplishing a line bleed sequence in operating apparatus such as shown in FIG. 21;

DETAILED DESCRIPTION

Starting Slides

Figure 1:
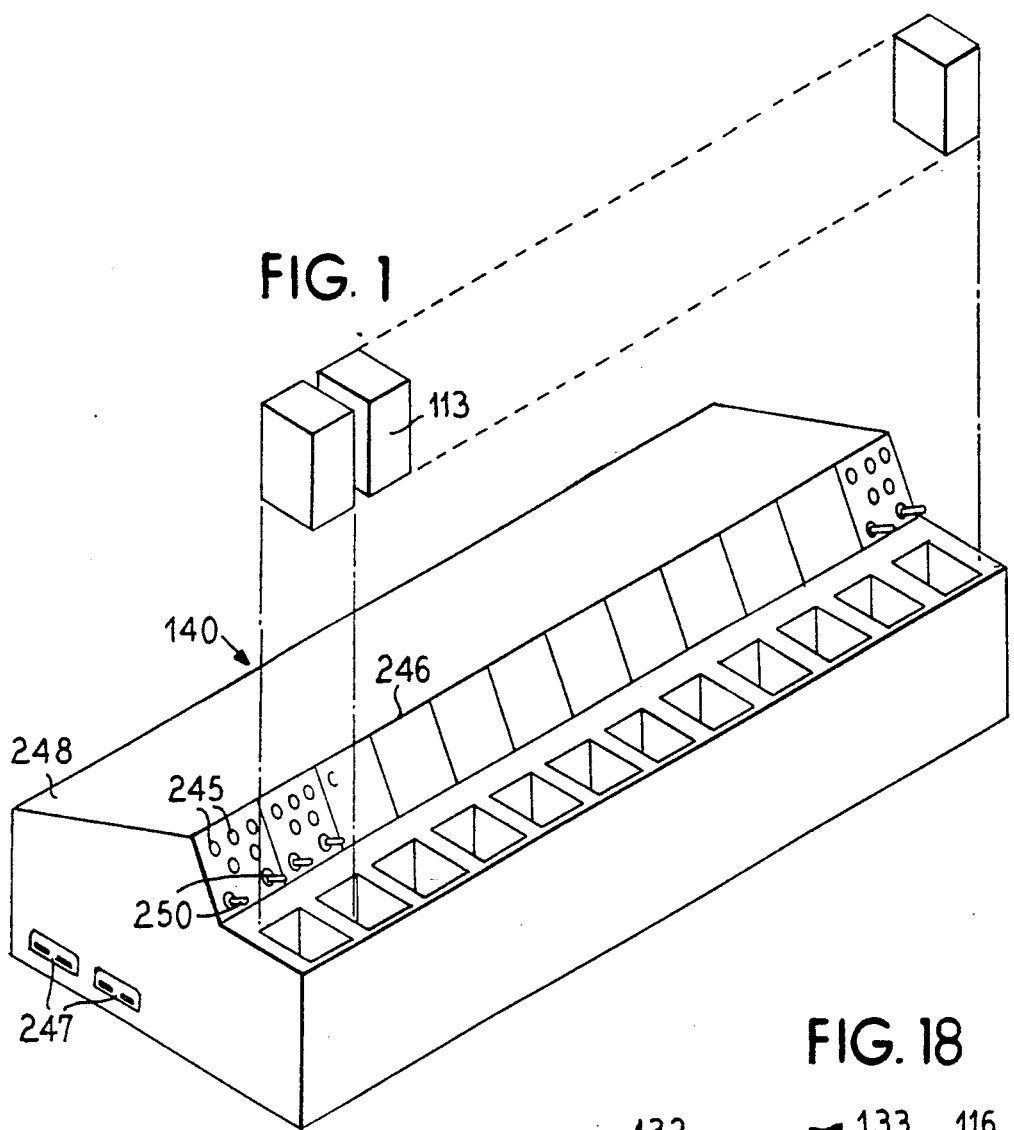
FIG. 1 is a perspective view of one embodiment of sequential multi-step slide processing apparatus of the present invention.

A slide is a self supporting, generally flattened plate of self-supporting substance upon at least one surface of which a material to be examined, processed, or the like can be placed, supported, and preferably adhered or bound by some means.

In the present preferred practice of this invention, a material to be processed in a sequential, multi-step procedure is mounted on a surface portion of a slide. Such surface portion lies within or on a predetermined surface location of a slide. Such slide surface location is positioned in or on, or forms one wall of, a chamber of a given slide processing station with which the resulting slide is to be associated in the practice of this invention.

Typically and even preferably, the slide surface portion is pretreated to achieve better material retention thereto than is achieved on the bare slide surface. Various slide pretreating procedures can be used, as desired.

One common pretreating procedure involves subbing the slide surface with a composition of gelatin and chrome alum.

Another known slide pretreating procedure involves use of a polylysine coating for slides that are used in certain protocols for cytological preparations.

The foregoing slide preparation procedures are illustrative for use with glass slides particularly. While conventional glass slides are presently preferred, those skilled in the art will readily appreciate that any convenient slide structure or slide preparation procedure can be employed for purposes of utilizing the apparatus and methods of this invention. In place of glass slides, slides comprised of plastic, metal, ceramic, or the like can be employed. A slide need have no particular characteristics for use in this invention. Slides known to the prior art or otherwise can be employed, if desired.

For example, the sequential multi-step surface treatment of a specimen deposit on a slide structure 20 such as shown in FIGS. 14 and 15 may be used, if desired. Slide structure 20 employs a substrate 21 that is preferably configured as a rectangular slide-like member which is relatively rigid, self-supporting, dimensionally stable, and preferably transparent. Substrate 21 can be comprised of a molded thermoplastic, such as an acrylic resin like polymethylmethacrylate, or other acrylate polymer, or the like, or of glass, such as a silicate, or the like. A convenient thickness for substrate 21 is in the range of about 0.5 to 2.5 mm although thicker and thinner structures can be employed. Convenient outside perimeter dimensions for substrate 21 are in the width range of about 1.5 to about 2.5 centimeters and in the length range of about 10 to 40 centimeters, although longer and shorter such dimensions can be used, if desired. Presently most preferred dimensions are similar to those of the conventional glass slide.

Substrate 21 has a large (relative to the total substrate 21 surface area) aperture 22 centrally located therein and transversely extending therethrough. The perimeter configuration of aperture 22 can be circular, oval, square, rectangular (presently preferred), or the like. The perimeter dimensions of the aperture 22 are a matter of user choice, but it is presently preferred to have a border along the sides thereof which provides sufficient structural integrity for practical use presently preferred. The area of this aperture 22 can range from about 100 $mm^2$ to about 600 $mm^2$ although larger and smaller such areas can be employed depending upon circumstance.

Laminated over preferably the entire surface of one of the opposed parallel faces of substrate 21 is a layer 23 comprised of a plastic which is conveniently translucent or preferably transparent. The lamination can be accomplished by any convenient means, including, for example, heat sealing, an adhesive (not shown), or the like. Layer 23 is flexible, resilient, and dimensionally stable at ambient conditions. Also, layer 23 is, like substrate 21, relatively inert, but is able to have mounted thereon on its outside surface portions 24 (particularly in the region thereof opposite aperture 22) a thin layer 25 (whose thickness, in effect, is exaggerated in FIG. 15 for illustrative purposes), or the like, of a specimen material which is to undergo a multi-step processing procedure, such as taught, for example, by the present invention. Preferably and conveniently, such a specimen material can be so mounted on surface 24 by procedures known to the prior art.

Layer 23 is further characterized by a capacity to deform elastomerically particularly in regions thereof that are adjacent to the perimeter of aperture 22 when a super-atmospheric or subatmospheric fluidic (preferably gaseous, such as air, nitrogen, or the like) pressure is applied against the inside surface 26 of layer 23 through the aperture 22. Such deformability is utilized, as hereinbelow described, at a processing station in a multi-step processing sequence using apparatus and methods such as taught in the present invention when the station chamber volume is being changed (see FIGS. 16 and 17 and the herebelow description relative thereto). The layer 23 can be comprised of various polymers, such as polyethylene terephthalate, polyvinylidene chloride, and the like. A convenient thickness for layer 23 is in the range of about 5 to about 50 microns, although thicker and thinner such layers can be employed, if desired. Suitable adhesives for laminating a layer 23 of polyethylene terephthalate to a substrate 21 of acrylic polymer include low molecular weight polyoletin and the like. The adhesive layer can have a thickness of about 5 to about 20 microns, although thicker and thinner layers can be used.

Regions adjacent to aperture 22 on each opposed interior (relative to substrate 21) side thereof provide surface areas which can, if desired, be associated with identifying indicia, such as alphanumeric characters, bar codes, and/or the like (not shown). Also, if desired, such an indicia-bearing surface area can be associated with a relatively short strip 27 of magnetic material which is mounted by an adhesive or the like (not shown) on the outside surface portions 24 of layer 23. Identifying information in machine readable form can be recorded in strip 27. Thus, the slide structure 20 provides the capabilities for completely automating the sequential, multi-step processing of a plurality of such slide structures 20 using apparatus and methods of this invention.

In general, for the practice of this invention, slides of conventional dimensions can be used and are presently preferred. For example, a standard glass slide such as is used for biological material mounting has a width of about 25 mm, a length of about 75 mm, and a thickness of about 1 mm.

Specimen Preparation

Conventional material or specimen preparation and slide mounting procedures can be employed for use in the practice of the present invention. Many such procedures are known to the prior art and such do not per se constitute a part of the present invention.

In general, it is preferred, for purposes of practicing this invention, that slides which have been prepared with a surface portion thereof that has mounted or coated thereon an adhering layer of a specimen material which is to be processed using the teachings of the present invention also have adjacent surface portions which are uncoated with such specimen material. This permits the uncoated surface portions to be used for other purposes, such as slide labeling for identification purposes, or handling, positioning, holding during processing, and the like.

The mounting of a biological specimen on a slide, such as a tissue slice, or the like, can involve biological tissue from any known source and such tissue can be mounted on a slide by using well established procedures. Specimen material coatings can likewise be prepared from any known source using established coating procedures. Terms such as "coating", "mounting", and the like are, for convenience, used interchangeably herein.

While the thickness of a specimen material coating on a slide can vary, depending upon such factors as the specimen, the objectives, and the wishes of a user, it is presently preferred for slide processing purposes in accord with the present invention that the specimen material coating be uniform, and have a thickness which is presently preferably not more than about 0.001 inch (about 25 microns). Also, the specimen material coating should be sufficiently structurally porous or permeable to permit fluids that are contacted therewith during a multi-step processing procedure that is conducted in accord with teachings of the present invention to penetrate to all portions of the coating. A presently most preferred coating thickness is substantially uniform. The surface area occupied by such a specimen material coating (or layer) on a slide surface can vary greatly in size depending upon the desires of the user and the particular equipment limitations, such as in the processing chamber size, or in apparatus reservoir capacity, etc. A presently preferred coating area size, for example, when employing a glass slide having the foregoing conventional dimensions, is in the range of about 100 $mm^2$ to about 600 $mm^2$ although larger and smaller such surface areas can be employed, if desired, depending upon such factors as processing station chamber dimensions, and the like, as will be appreciated by those skilled in the art.

Great variations in specimen material coating (including tissue slices) thickness, coated area, composition, and other characteristics are possible. In general, various coatings can be used in the execution of a multi-step processing sequence that is suitably carried out utilizing the teachings of the present invention, as those skilled in the art will readily appreciate.

Starting Probes

When it is desired to employ a probe or probes for slide surface treatment in the course of a multi-step processing sequence that is carried out in accord with the teachings of this invention, one can employ probes known to the prior art. Known processes can be used for the preparation thereof. Recombinant DNA technology now provides the opportunity to obtain either DNA or RNA probes of any desired sequence. One can choose between single stranded and double stranded probes. For hybridization to DNA or to RNA in a cytological preparation, as in in situ hybridization, double- and single-stranded probes, both DNA and RNA, have been successfully used. Particularly for hybridization to RNA in cytological preparations, it is generally preferred to use short probes that contain, for example, about 50 to about 150 nucleotides each because such seem to yield the most efficient hybridizations. Prior art indicates that RNA probes produce less background than DNA probes.

Procedures known to the prior art can likewise be used for the preparation of probes into compositions for use in a hybridization carried out using a processing step sequence in accord with the teachings of this invention. Such preparation procedures and compositions do not constitute per se a part of the present invention. If desired, an aqueous probe treating composition can contain, for example, in addition to a labeled probe, *E. coli* DNA or RNA to reduce non-specific binding of a DNA probe, Denhardt's solution (0.02% each of bovine serum albumin (BRL), Ficoll (Sigma), and polyvinyl pyrollidone (Sigma)) to reduce the background, dextran sulfate to accelerate hybridization, or the like.

For purposes of understanding and illustration in relation to utilization of the apparatus and methods of this invention, multi-step prior art processing procedures for staining and hybridization of slide mounted material are now briefly reviewed:

Prior Art: Staining

For example, in prior art immunohistochemical staining, for purposes of microscopic study and analysis or the like, an organ or the like that has been imbedded in paraffin or the like and/or has been frozen is cut using a microtome into sections perhaps about 3 to about 5 microns thick and attached to glass slides. The frozen tissue sections may be treated with acetone and then washed a plurality of times with buffered saline solution or the like before use. Paraffin treated tissue sections may be heat treated at about 56° C. or the like, and then washed in xylene to remove (dissolve) the paraffin. Thereafter, the specimen may be rehydrated in decreasing grades of ethanol, then treated with dilute aqueous hydrogen peroxide for about 30 minutes, and then washed with buffered saline. After drying, the resulting specimen can be contacted with a staining agent, which can be an antibody-mediated staining agent, or the like, incubated, and washed a plurality of times in buffered saline solution or the like to remove such excess staining agent. After drying, the resulting specimen may be contacted with another reagent, incubated, and washed similarly a plurality of times. Such an incubation and wash sequence may be repeated three, four, or more times before a final drying is carried out.

In accord with the present invention, the various post-slide mounting procedural steps for staining, can, if desired, be carried out using apparatus and methods of the present invention.

In general, an immuno-staining protocol calls for a fixing and permeabilizing step (methanol or other alcohol or aldehyde treatment), the binding of a polyclonal or monoclonal primary antibody to the target hapten, followed by the binding of a secondary antibody that is enzyme (or otherwise labeled) to the primary antibody, and finally a detection step. The nature of the detection step depends upon the label that is attached to the secondary antibody. The resulting processed slides are viewed under a light microscope.

If desired, the secondary antibody can be omitted, in which event, the label can be attached directly to the primary antibody.

A detailed description of the use of antibodies for cell or tissue staining is given, for example, in "Antibodies. A Laboratory Manual," Ed Harlow & David Lane, Cold Spring Harbor Laboratory, 1988.

Of course, less complicated staining procedures may be used, such as procedures which do not involve the use or application of reagents that stain cells or tissues directly without the aid of coupling agents such as DNA probes or antibodies. A comprehensive listing of such prior art staining procedures and starting materials can be found in "Staining Procedures" 4th Edition, George Clark (Ed), Williams & Williams.

Prior Art: In Situ Hybridization

For another example, in prior art in situ hybridization, for purposes of cell component study and analysis, or the like, a cytological material or material preparation is spread upon and retained over a slide surface portion using one of the many prior art procedures. The mounted material contains DNA and/or RNA sequences (the nucleic acid targets). In a step of a multi-step sequential processing procedure, such targets are selectively bound to labeled complementary nucleic acids (the probes). A preliminary cytological preparation procedure preferably gives well spread and very flat slide mounted preparations since such preparations have the best morphology and give the best hybrid signals. Some fixatives, such as those containing formaldehyde, appear to interfere with the denaturation and so are preferably avoided. Excessive acid treatments may depurinate the nucleic acids and so reduce the level of hybridization. Storage of slide mounted preparations in ethanol may cause loss of nucleic acids and reduce hybridization.

Typically, once a cytological preparation is slide mounted, processing for hybridization can begin. Depending upon the specimen, various procedures can be practiced. For example, a mounted specimen of *Drosophila polytene* chromosomes or of squashed tissue cells may be given preliminarily three successive washes of 95% ethanol of 10 minutes each, then air dried. Pretreatment of slide surface mounted cytological material before hybridization can involve various steps. For example, a prior art pretreatment of such slides before hybridization to DNA that is taught by Mary L. Pardue in "In Situ Hybridization", pp. 179-202 in "Nucleic Acid Hybridization", B. D. Hames and S. J. Higgins, Ed., published by IRL Press 1985, last reprinted in 1988, involves the following steps:

1. Incubate the slides in 2X SSC at 70° C. for 30 minutes. The composition of SSC is 0.15M NaCl, 0.015M trisodium citrate, pH 7.0 (with NaOH).
2. Transfer the slides to 70% ethanol at room temperature for 10 minutes. Wash again in 70% ethanol and then in 95% ethanol for 5 minutes. Air dry.
3. Arrange the slides in a moist chamber containing 2X SSC). Place 100 μl of RNase (100 μg/ml in 2X SSC) over the preparation on each slide and cover each with a coverslip (22 mm$^2$). The RNase is pancreatic in origin and is dissolved at the rate of 1 mg/1 mg in 20 mM sodium acetate, pH 5.0, and placed in a boiling water bath for 5 minutes. Aliquots are stored at −20° C. and diluted as required immediately before use. Pre-treatment of cytological preparations with RNase to remove total RNA is carried out with a high enzyme concentration (100 μg/ml). Post-treatment of preparations after hybridization to remove only non-hybridized RNA is carried out at a lower concentration of enzyme (20 μl/ml).

4. Incubate the slides at room temperature for 2 hours. Then remove the coverslips gently by dipping the slides into a beaker of 2X SSC to float off the coverslips.
5. Wash the slides in 2X SSC (about 3 to 5 minutes), 70% ethanol (about 2 to 10 minutes) and 95% ethanol (5 minutes). Air dry.
6. Suspend the slides in 0.1M triethanolamine-HCl, pH 8.0. Stir the solution vigorously and add acetic anhydride to 5 ml per liter.
7. When the acetic anhydride is thoroughly dispersed, stop the stirring and leave for 10 minutes.
8. Wash the slides in 2X SSC (5 min, 70% ethanol (about 2 to 10 minutes) and 95% ethanol (5 minutes). Air dry.
9. Place the slides in 70 mM NaOH for 3 minutes. Then wash the slides in three changes of 70% ethanol (10 minutes each) and two changes of 95% ethanol (5 minutes each).
10. Air dry.

For another example, a prior art pretreatment of such slides before hybridization to RNA that is also taught by Pardue (supra) involves the following steps:
1. The slide mounted cytological preparation may be preliminarily digested with protease to improve access of the probe to cellular RNA.
2. Acetylate the preparation (using, for example, steps 6-9 in the foregoing procedure) to reduce non-specific binding of the probe. Alternatively, wash the preparation with physiological buffer with the choice of buffer depending upon the tissue under study, transfer to distilled water, and use immediately for hybridization. In this case, take care that no water is left on the slide to cause dilution of the probe.

Hybridization, or the contacting of mobile probes with mounted targets (in such a mounted, processed slide cytological preparation), can be carried out by various procedures. Pardue (supra), for example, teaches that hybridization can be carried out either in an aqueous salt solution, such as TNS buffer (0.15M NaCl, 10 mM Tris-HCl, pH 6.8) at a high temperature, or in the presence of formamide at lower temperature.

For example, hybridization in aqueous salt solution at high temperature is commonly carried out in 0.3M NaCl, 20 mM Tris-HCl, pH 6.8 at 67° C. using 1-10 ng of the probe per slide. If a DNA probe is being used, sheared, denatured $E.\ coli$ DNA may also be added at a rate of, for example, 4.0 $\mu$g per slide to reduce non-specific binding of the probe. If an RNA probe is being used, $E.\ coli$ rRNA is added instead. About 15 to about 20 $\mu$l, for instance, of the hybridization mixture is placed over each slide mounted cytological preparation and covered with a coverslip (18 mm$^2$). Slides are maintained over a reservoir of hybridization buffer in a tightly-sealed moist chamber at 67° C. The amount of liquid in the chamber must be sufficient to prevent evaporation from under the coverslip. Typical hybridization times are about 12 to about 14 hours at 67° C.

For another example, hybridization in aqueous formamide solution is commonly carried out using, for example, 40% formamide in 4X SSC at 40° C. The amounts of probe and $E.\ coli$ DNA used per slide are as above described for hybridization in aqueous salt solution. Here, for example, 5 $\mu$l of the hybridization mix is placed over each preparation and covered with a coverslip (18 mm$^2$). The coverslip is sealed with a thick coat of rubber cement which saves the expense of filling a moist chamber with formamide buffer to prevent evaporation from under the coverslip. The sealed slides are incubated in a closed container on moist paper towels to prevent drying of the rubber cement. Typical incubation times are about 12 to about 14 hours at 40° C.

After hybridization, processing of slide surfacemounted cytological material can involve various steps. After removal from the moist chambers, the coverslip and the hybridization mixture are washed off using, for example 2X SSC in a beaker and slide dipping. Alternatively, if the slides were sealed with rubber cement, such cement is peeled off first. Then, the slides are placed in a staining dish containing 2X SSC and left for perhaps 15 minutes.

Thereafter, non-specifically bound nucleic acid probe can be removed, for example, by washes, particularly at a temperature which is slightly less than the hybridization temperature or by RNase treatment. Pardue (supra) describes the following post-hybridization procedure for RNA probes:
1. Place slides in RNase (as above characterized herein) 20 $\mu$g/ml in 2X SSC or in 0.5M NaCl, 10 mM Tris-HCl, pH 8.0, at 37° C.) for ½ to 1 hour.
2. Rinse slides in 2X SSC at 37° C. twice for 10 minutes each or wash in the above Tris-HCl containing buffer for 30 minutes at 37° C., then in 0.1X SSC for 10 minutes at 50° C., and then 0.1X SSC at room temperature for 10 minutes.
3. Dehydrate in 70% ethanol, then 95% ethanol, and air dry.

And the following procedure for DNA probes:
(1) Remove non-hybridized probe by repeated washing in hybridization buffer at a temperature a few degrees below the temperature of hybridization,
(2) Wash slides at room temperature in 0.1X SSC,
(3) Dehydrate in 70% ethanol, then 95% ethanol, and air dry.

In addition, when the probe is indirectly labeled, further processing steps are needed to react the probe labels with moieties which render the probes and their bound nucleic acids visible or detectable. For example, when the probe is initially labeled with biotin or a hapten, and, after hybridization has occurred, the residual probes have been removed, the hybrids are contacted with a coupling agent, such as, for example, avidin, streptavidin, or antibody that is labeled with, for example, a fluorophore-containing, radioisotope containing chromogen-containing, or enzyme-containing moiety, or the like. Thereafter, residual unbound coupling agent material is removed by washing When the probes are initially labeled with an enzyme, and, after hybridization has occurred, the residual probes have been removed, the slide bound hybrids are contacted with an identifying substrate which converts by enzyme action thereon to a chemiluminescent agent which emits photons. Alternatively, a chromogen substrate is added which is likewise enzyme converted to a color body. Thereafter, residual unbound substrate material is removed by washing.

When the probe is initially labeled with avidin, streptavidin or antibody, and, after hybridization has occurred, and the residual probes have been removed, the resulting hybrids are contacted with a biotin or hapten which is labeled with, for example, a fluorophore, radioisotope, chromogen, enzymatically active protein, or the like to produce a detectable label moiety. Thereafter, residual so labeled unbound material is removable by washing.

Advantageously, various prior art post-slide mounting slide fluid contacting procedural steps for hybridization can, if desired, be utilized when using the present invention. Also, the present invention makes possible new and very useful hybridization procedures.

Apparatus: Processing Stations

Particularly for utilization in apparatus for sequential, multi-step processing of slide surface mounted material, the present invention provides new and very useful processing station apparatus for contacting slide surface portions with fluids.

Referring to FIGS. 2 through 9, there is seen one embodiment 36 of a slide processing station which is provided by the present invention and which is useful in sequential multi-step processing apparatus of the present invention as described herein. Station embodiment 36 incorporates a block member 37 which is comprised of a material with good heat transfer characteristics, preferably a metal, with aluminum or aluminum alloy being presently most preferred. Block member 37 generally has a rectangular configuration and includes a flat surface 38 for accommodating adjacently thereto one surface 39 of a conventional glass slide 41, or the like.

Surface 38 is provided with an interior region or portion 42 whose perimeter is defined by an open channel or groove 43 which is preferably generally rectangular in cross-section. Seated in groove 43 is a gasket 44 which extends about the perimeter of interior portion 42 and is adapted to make a fluid tight seal between the interior portion 42 and adjacent portions of surface 39 of slide 41 (see FIG. 9). The block member 37, the gasket 44, and the slide 41 cooperate to define a chamber 46 that is located between the slide surface 39 and interior portion 42. A present preference is to use a chamber 46 which is characteristically shallow in depth and elongated in breadth and length.

As shown, for example, in FIG. 9, the embodiment of the gasket 44, has, in vertical section, a generally flat bottom with generally symmetrically tapered but flattened side walls and a rounded top. Other gasket cross sectional configurations can be used, if desired. Gasket 44 extends continuously in groove 43. For example, for a conventionally sized glass slide, wherein the specimen coating occupies an area of about 400 mm$^2$, the transverse width of groove 43 around its perimeter can be, for example, about 0.125 inch and the transverse width of gasket 44 across its bottom can be about 0.113 inch. Also, and for the same example, the depth of groove 43 can be about 0.080 inch and the height of gasket 44 can be about 0.113 inch. Other such dimensions can be used, as those skilled in the art will appreciate.

Functionally, in the present embodiment of this invention, gasket 44 is elastomeric and compressible. Thus, when compressive pressure is vertically applied between its top and bottom, gasket 44 is compressed, and, with increasingly greater applied compression force, gasket 44 becomes distorted from its initial relaxed configuration, such as shown in FIG. 9. As the gasket 44 spreads, its cross-section deforms transversely (laterally). Thus, gasket 44 when compressed is adapted to fill at least some more of the channel 43 than it does when the gasket 44 is in its initial or relaxed state in channel 43.

The gasket 44 is preferably compressable vertically to an extent sufficient to cause the vertical height thereof to be equal to the vertical height of the groove 43, yet the gasket 44 is still sealingly engaged with adjacent surface portions of groove 43 and slide 41. Gasket 44, for example, can have a durometer hardness of about 25 shore A scale, although smaller and larger such durometer values can be used. Gasket 44 is preferably substantially inert, non-porous, and non-foamed so as to reduce and preferably prevent take-up (i.e., absorption or the like) by gasket 44 of common liquids, gases, and even solids, particularly aqueous liquids and also gases, such as air, nitrogen, and the like. Gasket 44 can be comprised of any suitable and convenient elastomeric material, including a silicone rubber, such as a polysiloxane, or the like.

Gasket 44 should preferably be sufficiently elastomeric to reassume its initial relaxed configuration when a vertical compressive force is removed therefrom, and preference gasket 44 should preferably be able to cycle from an uncompressed state to a virtually fully compressed condition an indefinite but large number of times (i.e., such as exists when gasket 44 is compressed into a configuration resembling groove 43 and is then allowed to expand back to its initial uncompressed condition). The size (i.e., volume) of a given chamber 46 is affected by the compressability of gasket 44 while maintaining its capacity to remain in sealing engagement with surfaces contacted therewith.

Block member 37 has fluid inlet and outlet channels 47 and 48 formed in side 81 thereof. In block member 37, channels 47 and 48 extend in generally spaced, parallel relationship to one another, for example, as shown, in FIG. 6. Each channel 47 and 48 has a block port 52 and 53, respectively, defined in the longitudinal side edge 81 of block member 37, and each such port 52 and 53 is provided with a relatively short, outwardly projecting conduit member or nipple 49 (paired). Each nipple 49 is conveniently comprised of stainless steel, copper, copper alloy, rigid plastic, or the like.

Over outside terminal surface portions of each nipple 49 a flexible plastic tube member (not detailed), or the like, is mountable by clamps, or the like, as desired. For purposes of mounting each nipple 49 in ports 52 and 53 of block member 37, the inside terminal surface portions of each nipple 49 are provided with a suitable metallic collar 51, and such arrangement is secured together into the ports 52 and 53 of block member 37 by swaging, soldering, engaged threads, or the like, as desired.

Each of the channels 47 and 48 graduates from its respective ports 52 and 53 downwardly to a smaller elongated channel 54 and 56 for flow enhancement purposes. The diameter of each channel 54 and 56 is preferably equal to the other thereof, an illustrative diameter being about 0.094 inch although larger and smaller such diameters can be used. Each channel 54 and 56 extends interiorly under the central flat surface 62 of interior portion 42 along the opposed side edges 59 and 61, respectively, of interior portion 42 and also adjacently to the gasket groove 43 as such extends along the side edges 59 and 61.

Over each of the channels 54 and 56 at opposed edge portions of central flat surface 62, a straight, elongated plennum 57 and 58, respectively, is formed. Each respective plennum 57 and 58 has arcuately and concavely shaped sides and a bottom which is depressed in block member 37 below the flat central surface 62 of interior portion 42. Each plennum 57 and 58 extends transversely across, and adjacently to, a different one of side edges 59 and 61. Each plennum 57 and 58 is in vertically, generally equally spaced relationship to a different adjacent underlying respective channel 54 and 56. In effect, plenna 57 and 58 reduce the surface area of central flat surface 62.

The surface area occupied by the flat surface 62 and also the plenna 57 and 58 is adapted to approximately correspond to the surface area occupied by a layer of specimen material that has been coated upon the surface 39 of a slide 41 which is to undergo multi-step processing in accord with the teachings of this invention. Illustrative dimensions are given above.

A plurality of small channels 63 and 64, which are vertically oriented relative to the plenna 57 and 58, respectively, are placed along the bottom of each plennum 57 and 58 in generally equally transversely spaced relationship to one another. Such channel pluralities 63 and 64 extend in block member 37 from the bottom of their associated respective plennum 57 and 58 interiorly to the top of the respective underlying channels 54 and 56. It is presently preferred for the diameters of the channels 63 and 64 to be equal to one another an illustrative diameter being about 0.0135 inch although larger and smaller diameters can be used. Thus, a fluid passageway is provided in each channel 47 and 48 extending from port 52 and 53 to the channels 63 and 64, such channels providing orifice means for fluid ingress and egress into chamber 46.

The interrelationship between the channels 63 and 64 is preferably such that a processing fluid can flow into chamber 46 from (when a slide 41 is engaged with block member 37 as described herein) for example, channels 63 and travel over the central flat surface 62 in chamber 46 in a laminar manner to exit through channels 64, or vice versa. As used herein with reference to flow, the term "laminar" has reference to a Reynolds number which is not more than about 2300. Thus, process fluids can be circulated to, through, and away from chamber 46.

To heat block member 37, a pair of electric resistance heater elements 66 and 67 are located in bore holes 33 and 34 (FIG. 5) formed in side 81 of block member 37. Heaters 66 and 67 are positioned so as to be in spaced, parallel relationship to one another between the channels 47 and 48 (see, for example, FIGS. 5 and 6) beneath the central flat surface 62.

To cool, and also to perhaps to heat, block member 37, as operational variables which may be regulated by an operator (depending upon operating conditions), a serpentine-like fluid passageway is provided in block member 37 which is located below the heaters 66 and 67. Such passageway is defined by drilling four spaced parallel bore holes 68, 69, 71, and 72 in side 82 of block members 37 such as shown, for example, in FIG. 7. The interior end of each outside bore hole 68 and 72 is interconnected with the interior end of the respective adjacent bore hole 69 and 71, respectively, by drilling opposed bore holes 73 and 74 from each one of the opposed sides of 83 and 84 block member 37 which are adjacent to the side 82 wherein such four bore holes 68, 69, 71, and 72 enter, the depth of each respective such bore hole 73 and 74 being sufficient to interconnect the end of bore hole 68 with bore hole 69, and the end of bore hole 72 with bore hole 71. Thereafter, each of such opposed bore holes 73 and 74 is plugged by a plug 31 which extends from respective sides 83 and 84 down to the edge of the respective bore holes 68 and 72. The respective outer end regions 86 and 87 of each bore hole 68 and 72 adjacent side 82 are enlarged and threaded with a tap, and the corresponding end region of each bore hole 69 and 71 is plugged by a plug 32 which extends from side 82 inwardly about the same distance that is occupied by threaded regions 86 and 87 in bore holes 68 and 72. To provide an interconnection between bore holes 69 and 71 in regions thereof adjacent the inner ends of the plugs 74, a bore hole 76 is placed in the side 83 of block member 37. Once this interconnection is achieved, a short plug 77 is placed in bore hole 76 in the region thereof which extends through the body portion of block member 37 separating bore hole 68 from bore hole 69, and another and longer plug 78 is placed in bore hole 76 in the region thereof which extends through the body portion of block member 37 from bore hole 68 to the side 83. Thus, the serpentine-like fluid passageway is provided extending from end region 86 progressively through the bore holes 68, 73, 69, 76, 71, 74 and 72 to end region 87.

Each threaded outer end region 86 and 87 is fitted with a threaded connector 88 and 89, respectively, that is, in turn, engaged with a conduit member 79 and 80. Each conduit member 79 and 80 can be a longitudinally short metal sleeve, if desired, which is insertable into the end of a flexible and clampable plastic tube (not shown), or the like, as desired, so that a temperature regulating liquid can be circulated through such serpentine passageway.

The use of such a combination of both electrical and fluidic temperature regulating means for block member 37 is employed as a present preference; other means for temperature regulation of block member 37 can be used, if desired. The present combination, however, provides excellent capacity for temperature control including the feature of being able to relatively rapidly change the temperature of block member 37 and also of a slide 41 that is associated therewith from one value to another, such as is sometimes desired, for example, in carrying out successive steps in a given multi-step processing sequence.

Block member 37 is further provided with a small channel 91 that extends normally therethrough from the back face 90 thereof to a location in about the middle of flat surface 62 in interior portion 42. Channel 91 in the region thereof adjacent to surface 62 during manufacture of block member 37 is enlarged by a counter bore 92 (as shown in FIGS. 5 and 8, for example) which terminates in a valve seat 93. Seat 93 is producable by first boring channel 91 with a smaller sized drill than that used to form the counter bore 92, but which is larger than the drill used to form channel 91, and then drilling bore 92. To provide a check valve assembly 94, an O-ring 96 is rested against the inclined surface of seat 93 and a ball 97 is nested thereagainst. A cylindrical valve body 98 is slidably forced into bore 92 and swaged in place, or the like, as desired, to retain body 98 in bore 92. Valve body 98 includes a blind interior central channel 99 within which is positioned along the axis of body 98 a coiled compression spring 101 which yielding maintains the ball 97 normally in sealing and seated engagement with O-ring 96. Longitudinally extending in radially spaced relationship to the longitudinal axis of valve body 98 are a plurality of circumferentially spaced fluid channels 102, preferably four. These channels each overlap upon a longitudinally extending edge portion of central channel 99, thus providing passages so that fluid can flow from channel 91 through and out of channels 102 when the ball 97 is unseated from O-ring 96.

The check valve assembly 94 and the channel 91 are of small size. For example, the diameter of channel 91 can be about 0.022 inch, although larger and smaller diameters can be used. The O-ring 96, for example, can have an outside diameter in the range of about 0.055 to about 0.060 inches (preferably about 0.057 inches) and an inside diameter of about 0.015 to about 0.020 inches (preferably about 0.017 inches)

To open check valve assembly 94, and introduce a fluid into chamber 46 through channel 91, a hypodermic needle 103 with a point region 104 that is notch configured as shown in FIG. 10 is used. Preferably, the hypodermic needle 103 has an outside diameter such as about 0.020 inches, which permits easy slidable engagement with channel 91. Such point region 104 has an inwardly extending notch 106 formed therein whose interior apex 107 is at the axis 108 of hypodermic needle 103. Each side 109 of notch 106 is preferably symmetrically configured relative to the other thereof. Preferably, each side 109 makes an angle of about 45° with respect to the axis 108 when needle 103 is viewed in side elevation (as shown in FIG. 10).

Figure 2:
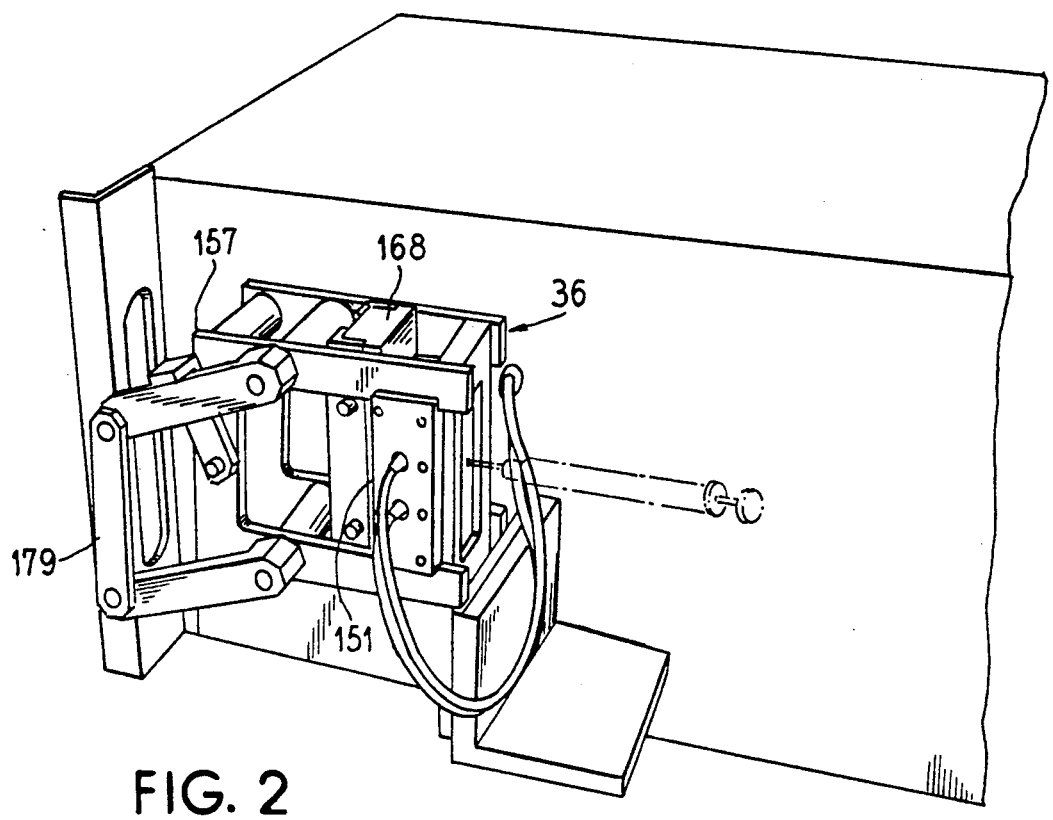
FIG. 2 is an environmental view in perspective showing one embodiment of a slide processing chamber block assembly employable in apparatus such as shown in FIG. 1 which block assembly is equipped with a cam type slide holding means, this Figure also showing in phantom a hypodermic syringe and adapted needle in functional association therewith.

When as illustrated in FIG. 2 the hypodermic needle 103 is inserted from the back side 90 of block member 37 into channel 91, the point region 104 engages ball 97 and sufficient longitudinal pressurizing force is applied to needle 103 to unseat ball 97 from O-ring 96. The needle then passes through the O-ring 96 forming a seal which prevents fluid from escaping back between the needle 103 and the channel 91. Fluid can then be injected in a measured amount from a hypodermic syringe associated with needle 103 through needle 103 past notch 106 and hence into fluid channels 102 for transfer into chamber 46. Thereafter, when needle 103 is withdrawn from channel 91, the ball 97 reseats against O-ring 96, thereby sealing channel 91 and preventing movement of fluid back out from chamber 46 past the check valve assembly 94 and out through channel 91. Utilization of channel 91, check valve assembly 94, hypodermic needle 103, and associated components in the practice of this invention is described hereinbelow.

For positioning, holding and temperature regulation purposes, the block member 37 is nestably positioned in a formed (by machining or molding) container-like housing 151 comprised of a thermally insulating plastic, such as a nylon, a polyester, an acetal, or the like. The back face 90 of block member 37 rests against the inside surface of the back 150 of housing 151, and the sides 83 and 84 of block member 37 rest against the respective inside surfaces of the sides 148 and 149 of housing 151. Side 81 of block member 37 rests against the inside surface side 147 of housing 151. The remaining side 82 of block member 37 is covered by cover plate 155 which is secured to edge portions of sides 148 and 149 and back 150 by machine screws 154, or the like. Apertures 153 are provided in cover plate 155 for extension therethrough of connectors 88 and 89 and conduits 79 and 80. Also, apertures 152 are provided in side 147 of housing 151 for the electric heating elements 66 (pair) and the associated collar and nipple assemblies 51 and 49 (paired). The back 150 has an aperture 152 centrally located therein which is preferably centered over the entrance to channel 91 in back face 90. The surface 38 of block member 37 remains uncovered.

To hold slide 41 against surface 38 of block member 37, station embodiment 36 is provided with a releasable slide holder subassembly 156 which incorporates a pair of U-shaped frame members 157. Each member 157 is disposed in spaced, parallel relationship relative to the other thereof. A region of the open end portion of each leg 161 (paired) of each member 157 extends upwardly (relative to surface 38 of block member 37) from a position that is spatially adjacent one respective side edge 83 and 84 of block member 37. The integral crossover 162 of each member 157 is thus elevated relative to its adjacent side edge 83 and 84. The open end of each leg 162 is secured by machine screws 158 or the like to adjacent side edge portions of a bottom plate 159 that rests against back 159. The opposite end of each crossover 162 is secured by machine screws 158 or the like to an abutting end of a spacer bar 163 (paired). Bottom plate 159 has a relatively large, centrally located, generally rectangularly configured aperture 164 formed therein to provide easy access therethrough past aperture 152 in housing 151 to channel 91. For positioning and holding the housing 151 against adjacent portions of the legs 161 of U-shaped members 157, side 147 is provided with a pair of outwardly projecting, integral, opposed ears or flanges 166 and cover plate 155 is provided with a pair of corresponding outwardly projecting opposed ears or flanges 167. These flanges 166 and 167 cooperate with legs 161 in holding housing 151.

The holder subassembly 156 further incorporates a slide retaining plate assembly 168 (see FIG. 5) which incorporates a transparent block or plate 169 preferably comprised of a transparent, relatively thermally insulative material that is preferably comprised of a plastic, such as an acrylic polymer, or the like. One flat face 171 of block 169 is adapted to fit against the back or opposed flat surface 40 of slide 41. The opposed face 172 of plate 169 is provided along each of its longitudinal side edges with L-shaped metallic mounting brackets 173 (paired). Each bracket 173 is inset into adjacent portions of block 169 and is mounted by machine screws 164 or the like. Thus, slide 41 is viewable through plate 169 when the plate assembly 169 is positioned adjacent face 40 of a slide 41. The plate assembly is sized so that block 169 and its associated brackets 173 are slidably moveable between the pair of U-shaped frame members with the opposed, outwardly projecting heads of the machine screws 154 slidably engaging inside edge portions of each adjacent leg 161.

Between face 172 of plate 169 and each spacer bar 163 and between each of the legs 161, a pair of transversely positioned, cylindrically surfaced cam rollers 176 are rotatably but eccentrically mounted between the U-shaped frame members 157, by means of end associated spacer washers 177 and machine screws 178 extended though apertures formed in each leg 161 for threaded engagement with each roller 176. Thus, one cam roller 176 extends transversely between each spaced parallel pair of legs 161. The cam eccentricity is such that, when each roller 176 is rotated on its rotational axis to a location where the radial distance between the roller 176 axis is at about a minimum, a slide 41 can be inserted and removed from surface 38, yet, when each roller 176 is further rotated on its rotational axis, surface portions of each roller engage and exert compressive force against portions of angles 173 and the face 172 of plate assembly 168, thereby moving and compressing the surface 39 of slide 41 against the surface 38 of block member 37. The arrangement is preferably such that, when each roller 176 is moved to a position where such exerts a desired camming action against plate assembly 168, the gasket 44 is compressed to a desired extent. Maximum compression is achieved when gasket 44 is fully receivable within the channel 43, as discussed herein.

To rotate the two cam rollers 176 synchronously relative to each other, a parallelogram-type of actuating mechanism generally indicated by the numeral 179 is utilized. Mechanism 179 utilizes an identical lever arm 181 pair. One end of each lever arm 181 is pivotally associated with the rotation axis of each cam roller 176 and is fixed to rotate therewith about the same pivot axis.

The oriented position of each cam roller 176 is adjusted to be identical to the other thereof. The rotational movement of each cam roller 176 is fixedly coupled to each respective associated lever arm 181. Thus, arcuate movement of the opposed end of each level arm 181 produces a corresponding angular pivoting movement of the respective associated cam roller 176. At a given position of each cam roller 176, the lever arms 181 are in spaced, parallel relationship to each other.

A connecting arm 182 is rotatably secured by machine screws 183 or the like across the respective opposed ends of the lever arms 181 to complete a parallelogram-type lever arrangement such that spatial displacement of arm 182 regulates identical pivotal rotational movements of each cam roller 176.

Figure 4:
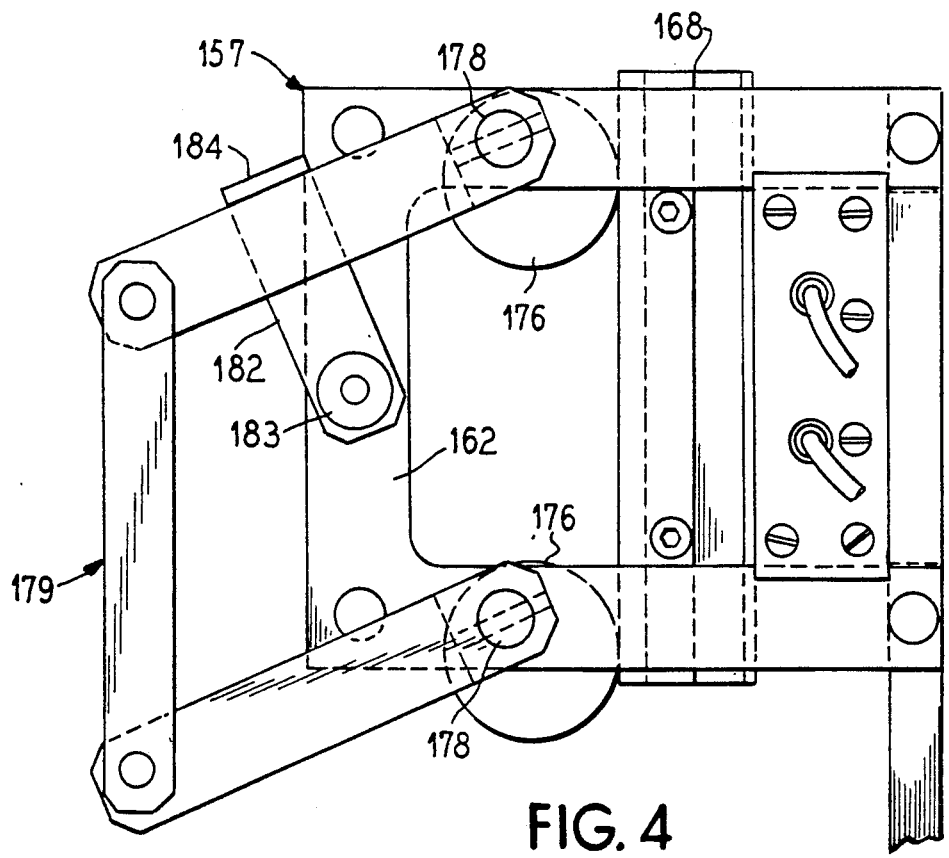
FIG. 4 is a side elevational view of the block assembly shown in FIG. 2.
Figure 4A:
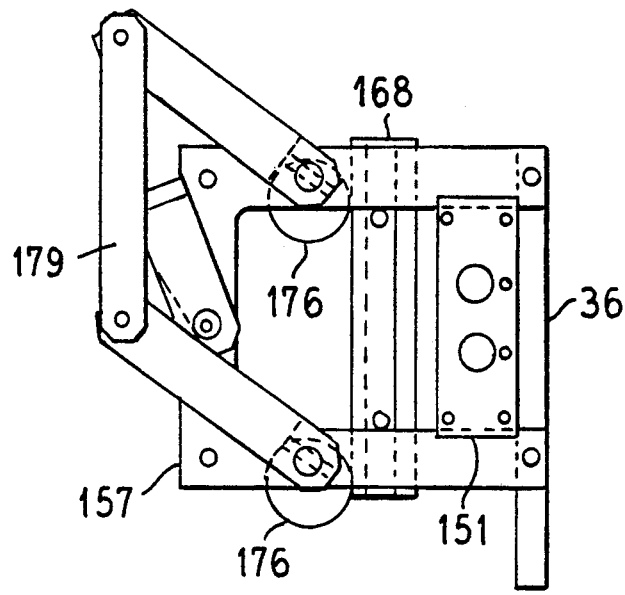
FIGS. 4A, 4B, and 4C are view search similar to FIG. 4, but illustrating three successive positions of advance for a slide holding block relative to a slide surface treating block using a parallelogram-type of cam actuated mechanism.
Figure 4C:
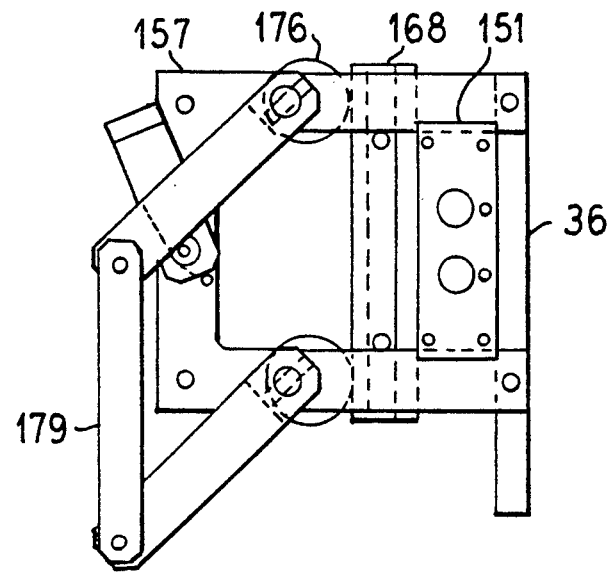
Figure 4B:
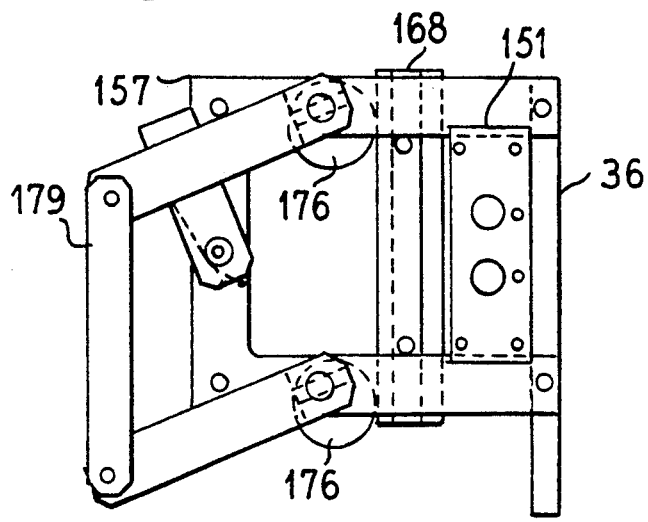

Those skilled in the art will readily appreciate that any desired setting can be selected for the spatial orientation of the lever arms 181 and connecting arm 182. However, for the exemplary and presently preferred arrangement is shown in FIGS. 2 and 4, the parallelogram-type of actuating mechanism 179 is moved and set (fixed) at any one of three positions, which are progressively illustrated in FIGS. 4A, 4B, and 4C, respectively. Specifically, position (a) as shown in FIG. 4A is an open position where the plate assembly 168 is in an open configuration relative to the block member 37, such as is useful for loading and unloading a slide 41. Position (b) as shown in FIG. 4B is an intermediate position, where the surface 39 of slide 41 has been positioned over the surface 38 of block 37 and the gasket 44 has been compressed by compression of plate assembly 168 against slide 40 to an extent sufficient to achieve a desired volume for the chamber 46. Position (c) as shown in FIG. 4C is a final position, where the gasket 44 has been compressed to an extent sufficient to completely contain gasket 44 in groove 43. The sequencing can be reversed, if desired.

In position (c) (see FIG. 4C), the surface 38 of block member 37 is in face-to-face engagement with the portions of surface 39 of slide 41 adjacent thereto. In order to achieve such a face-to-face engagement, adjustments may have to be made in mechanism 179 and in plate assembly 168, as those skilled in the art will appreciate. For example, shims (not shown) can be placed between plate 169 and angles 173.

In position (b) (see FIG. 46), the cam rollers 176 are partially extended against plate assembly 168. To maintain this position, a flattened retaining arm 182 is provided which has one end that pivots about the axis of a machine screw 183, or the like, that mounts such one end approximately in a mid-region of crossover 162. The opposite end of arm 182 is provided with a flange 184 positioned to overlie perpendicularly arm 182. When the parallelogram actuating mechanism 179 is positioned as shown in FIGS. 2 and 4 where the flat inside surface of the flange 184 rests against the edge of a mid region of one (here the uppermost) lever arm 181, the parallelogram actuating mechanism 179 is in effect retained or locked in such position or configuration. The retaining arm is preferably equipped with a biasing spring 186 (shown in phantom in FIGS. 4A, 4B, and 4C) that extends from screw 183 to one side of arm 182 so that arm 182 is urged into engagement with portions of actuating mechanism 179, as shown in FIGS. 4A, 4B, and 4C.

The volume of the chamber 46 when the slide 41 is in face-to-face engagement with the block 37 is determined by the spacing between the surface 39 of slide 41 and the surface 62 of interior portion 42 of surface 38 of member 37. In a region adjacent to interior portion 42, slide 41 has mounted thereon, as described herein, a layer or coating of specimen material which is to undergo multi-step sequential processing in accord with the teachings of this invention. When this layer is not more than about 0.001 inch (about 25 microns) in thickness, as is presently preferred, and when the surface 62 is lower (or is inset) relative to the surrounding surface 38 by about 0.001 inch (about 25 microns), as is presently preferred, the volume of chamber 46 (not counting the volume embraced by the plenna 57 and 58) is about 10 microliters for an exemplary surface area of surface 62 of about 400 mm$^2$ (which corresponds to a preferred area of specimen material deposited on a slide for processing, as above explained).

Although such a volume can be adjusted by controlling such a factor as the thickness of the layer of slide specimen material on a slide 41, tests and evaluations, as well as practical and theoretical considerations, indicate that a volume for a chamber 62 of about 10 microliters is a minimum value for a slide surface area of about 400 mm$^2$. Smaller volumes tend to cause contact areas between the commonly present coated slide surface irregularities (owing to the specimen and to the slide coating procedure) and the adjacent surface 62, so that "dry" or unprocessable areas on the coated slide surface result, which are generally regarded as unacceptable for uniform multi-step processing purposes. Also, treating liquid viscosity, surface tension, capillary properties, and the like seem to present handling and processing problems when and if smaller volumes for a chamber 46 are used.

While processes of using a slide processing station 36 are hereinafter described, it is here noted that for a conventional standardized slide with the dimensions hereinafter indicated having a coating of specimen material that is not more than about 25 microns in thickness and that occupies a surface area of about 440 mm$^2$ (which corresponds to the combined surface area of flat surface 62 and gutters 57 and 58), and for the gasket 44 and the groove 43 having dimensions and characteristics as above indicated, the maximum volume of chamber 46 can be, for example, in the range of about 650 to about 700 microliters with an effective fluid seal being maintainable between gasket 44 and slide surface 39, although higher and lower values can be obtained. However, with such slide parameters, it is presently preferred, and operationally convenient, to employ a fluid volume for chamber 46 which is about 200 to about 250 microliters for purposes of conducting multi-step fluid processing in accord with the teachings of this invention when process fluids are being passed (i.e., circulated) through chamber 46 using ports 52 and 53. The actuating mechanism 179 is adjusted (i.e., set) so that such is in the above described position (b) when such a chamber 46 volume of 200 microliters is described. Then, when a chamber 46 volume of the order of about 10 microliters or the like is desired, the actuating mechanism 179 is readjusted (i.e., set) so that such is in the above-described position (c).

Although the operations of slide 41 positioning and removal upon block 37, and the associated operations of positioning the actuating mechanism 179 and the plate assembly 168, are accomplishable manually, those skilled in the art will appreciate that slide surface processing apparatus of this invention can be provided with means which will permit fully automated operations which would thereby eliminate such manual actions, if desired. For example, the actuating mechanism 179 can be operated remotely by a fluidic cylinder, such as a pneumatic cylinder that is actuated by computer controlled, solenoid actuated valves (not shown) or the like. Also, although the actuating mechanism 179 is here used in only three operating positions, those skilled in the art will appreciate that an indefinitely large number of operating positions can be used therewith, if desired, such as when and if it is desired to operate the apparatus and methods of this invention with more than two operating volumes for chamber 46 with a slide 41 in place. Of course, and as explained herein, processes and apparatus of this invention can be carried out, if desired, using only a single volume for such a chamber 46.

When station 36 is employed in a multi-step sequence where one step of the sequence has a reduced or even minimized volume for chamber 46, the apparatus operation can be carried out using a step sequence employing a first relatively large volume for chamber 46. At the end of this sequence, the chamber 46 can optionally be subjected to drying conditions, as in a separate step of the sequence. Thereafter, with the processing station positioned so that the associated slide is preferably vertically oriented, a small amount such as an amount less than about 20 µl of a processing liquid, such as an expensive aqueous probe containing processing liquid or the like, is input into chamber 46 using a hypodermic needle as shown in FIG. 10 through the channel 91. The apparatus configuration is illustrated in FIG. 2 with such syringe and needle being shown in phantom. The amount of such processing liquid injected is influenced by the size of the slide surface area that is undergoing processing and by the size of the chamber 46 which is subsequently to be achieved. For example, for a slide processing area of about 400 mm² and about a 10 microliter chamber volume, about 10 microliters of processing liquid is injected. Thereafter, the chamber 46 volume is reduced by operation of the holder subassembly 156. The effect of the compression thus produced between the surface 39 of slide 41 and the surface 62 of block 37 is to cause a squashing action on the so injected liquid which spreads out over the slide surface being processed, as desired The block 37 temperature is preferably concurrently regulated to a desired value.

After a predetermined time interval, such as an incubation time in the case of hybridization, the chamber 46 volume is expanded and a liquid circulation therethrough is commenced, such as a wash liquid in the case of hybridization. The injected liquid is thus swept out of the chamber 46 and removed from the slide surface (without reuse). Other steps of a multi-step processing sequence can then be subsequently executed.

Referring to FIG. 11, there is seen another embodiment of a block member 191 which is useful in a slide processing station adapted for employment in sequential multi-step processing apparatus of this invention. For example, block member 191 can be adapted to replace block member 37 in slide processing station 36.

Block member 191 can be considered to have an internal structure which is comparable both to the internal structure of block member 37 as regards processing fluid throughput, and also to electrical and fluidic temperature regulating means. For example, the ports 192 and 193 can be considered to correspond to the ports 52 and 53 of block member 37, and the channels 194 and 195 can be considered to correspond to the channels 63 and 64, respectively, of block member 37. Plenna comparable to the plenna 57 and 58 are not utilized in block member 191 which employs in place of the combination of central flat surface 42 and plenna 52 and 63 a single central flat surface 197. The preferred laminar flow of processing liquid over central flat surface 197 from channels 194 to channels 195, or vice versa, is achievable.

Surface 197 is depressed as regards its spatial level relative to the surrounding flat surface 198. Dimensionally, the surrounding flat surface 198 is adapted for receipt adjacently thereto of a slide member, such as a conventional glass slide (not shown), or the like, which has coated on one surface thereof a specimen material that is ready for sequential multi-step processing whose surface area preferably corresponds approximately to the surface area of flat surface 197. Such a specimen material coating can then be faced towards flat surface 197 with adjacent surrounding slide surface portions being in adjacent relationship to the surrounding flat surface 198.

In flat surface 198, and adjacent to and also around the perimeter of central flat surface 197, a shallow trough or groove 199 is provided which has a flattened bottom. Groove 199 serves as a seat for a gasket 200 (shown fragmentarily) (needs to be added to FIG.). Such a gasket is adapted to make sealing engagement with the slide surfaces positioned thereagainst. For example, a suitable gasket can be cut from a sheet of a latex-type elastomer. Suitable elastomers include polyurethane, polysiloxane, polybutadiene, or the like. The thickness of about 20 thousandths of an inch of such gasket is somewhat greater than the depth of the groove 199. Illustratively, the gasket can be derived from a latex sheet and can have a width of about 1 to about 4 mm, a thickness of about 0.5 to about 1.0 mm, and a durometer value in the range of about 20 to about 40. A shoulder of surrounding flat surface 198 is provided between groove 199 and central flat surface 197.

The depth of the central flat surface 197 relative to the surrounding flat surface 198 can vary, but a present preference is to employ a depth of about 0.015 to about 0.019 mm, with a depth of about 0.018 mm being presently more preferred. When a slide is positioned over such central flat surface 197, and the slide has a specimen material coating centrally disposed thereon as above indicated, then the volume of the processing chamber thus defined can range widely, thereby to achieve the particular value which a given user may desire. A present preference is to employ a chamber volume which is in the range of about 150 to about 600 microliters with volumes in the range of about 200 to about 350 microliters being presently more preferred.

The block member 191 is not provided with any avenue of processing fluid entry into the processing chamber other than through one of the ports 192 or 193. Instead of flowing a highly expensive liquid, such as a probe containing composition, into and through such a chamber via the ports 192 or 193, or vice versa, one can, for example, introduce only a limited quantity of liquid therein. The quantity used can be sufficient to fill the volume of the chamber. Such quantity of liquid is allowed to remain in the chamber for a specified time period (while controlling chamber temperature, if desired). Thereafter, one can either withdraw the liquid quantity from the chamber or flush (wash) the liquid quantity from the chamber. Such a wash can be carried out by flowing a wash liquid, or the like through chamber.

For example, when (a) block member 197 is positioned on one end thereof spatially, (b) a port 192 thereof is located at the gravitationally lowermost end thereof, and (c) such port 192 is provided with a Y-type three-way valve 201 of the type where one leg 202 thereof is normally closed, thereby permitting process fluid to flow from a second leg 203 through valve 201 into third leg 204 on into port 192, then a limited amount of a processing liquid, such as an aqueous probe-containing composition, or the like, can be input into such chamber by following a procedure.

First, continuous flow of process fluid through such chamber is terminated; for example, at the end of a process step in a step sequence. If the process fluid is a liquid, then such is drained from such chamber successively through the legs 204 and 203 with the conduit 206 that is associated with the other port 193 being vented to the atmosphere through an associated three-way valve 207, or the like. Valve 201 is then reconfigured so that fluid flow into or from leg 203 is cut off while fluid flow through leg 202 through valve 201 into leg 204 can take place, and the aqueous probe containing composition or other processing liquid is introduced into the chamber from a syringe or the like in an amount only sufficient to fill the volume of the chamber. Since conduit 206 is vented to the atmosphere, air or other gas in the chamber is displaced to the atmosphere as such introducing occurs. Thereafter, following a predetermined or measured residence time in the chamber, the composition or processing liquid may be withdrawn, if desired, back into the syringe by reverse action. Valve 201 then is reconfigured to its normal state with leg 202 closed and leg 203 open.

Alternatively, if desired, without so withdrawing the composition or processing liquid, valve 201 is reconfigured with the composition still in the chamber. In either event, after valve 207 is closed to its normal configuration so that fluid flow through conduit 206 occurs and atmospheric venting is terminated, then fluid flow through the chamber can again take place so that any of the composition or processing liquid in the chamber is immediately swept out therefrom and removed (though additional flushing or washing may be desired). Of course, since the volume of the chamber is fixed, the block member 191 inherently uses a greater quantity of such a composition or processing liquid than is used by the block member 37 when block member 37 is operated with at least two chamber positions and the chamber position used for input of such a composition or processing fluid is smaller in volume than that associated with the block member 191.

When block member 191 is used in the processing station embodiment 36, the parallelogram actuating mechanism is conveniently and preferably adjusted to one slide holding setting which achieves a desired chamber volume.

Referring to FIGS. 12 and 13, there is seen another embodiment 211 of a slide processing station which is provided by the present invention and which is useful in sequential multi-step processing apparatus of the present invention as described herein. Station embodiment 211 incorporates a block member 212 which can be structurally and functionally similar to that of block member 37 in station embodiment 36. Some comparable parts of block member 212 are numbered for convenience, and the numbers are similar to corresponding parts in block member 37 but with the addition of prime marks thereto for present identification purposes.

Station 211 employs a pair of circumscribing frame or support members 213 and 214 which are in spaced, parallel relationship to each other. Between frame members 213 and 214 and adjacent one side thereof is mounted a block 216 of transparent material which is conveniently and preferably comprised of plastic, such as a polymer comprised of acrylic resin, polycarbonate, or the like. The back surface of a slide is positioned against the inside face of block 216. The front face of slide 217, which has coated on a central area thereof a layer of specimen material (not shown) to be processed, is positioned against the surface 38' of block 212.

Block 212 is adapted for limited transverse sliding movements towards and away from slide 217 along and between the respective frame members 213 and 214. In FIG. 13, block 212 has been moved against slide 217 so that slide 217 is in sealed engagement with gasket 44' and is held between block 216 and block 212.

To regulate the sliding movements of block 212, a toggle mechanism 218 is provided. Mechanism 218 incorporates a U-shaped frame member 219 whose legs 220 (paired) each slidably extend across slots formed in each of the frame members 213 and 214. U-shaped frame member 219 can thus be reciprocatorily moved across frame members 213 and 214 with a fixed transverse spacing relative to block 212 and with the crossover portion 224 of U-shaped frame member 216 serving as a grasping handle for directing such movements thereof.

The sides of block 212 adjacent each leg of the U-shaped frame member 219 are interconnected by four toggle links 221, each one thereof being pivotally associated with both block 212 and such legs 220 by pins 222, or the like, that extend through the respective opposite end region of the link 221. Sliding movement of U-shaped frame member 219 thus produces transverse sliding movement of block 212.

Figure 16:
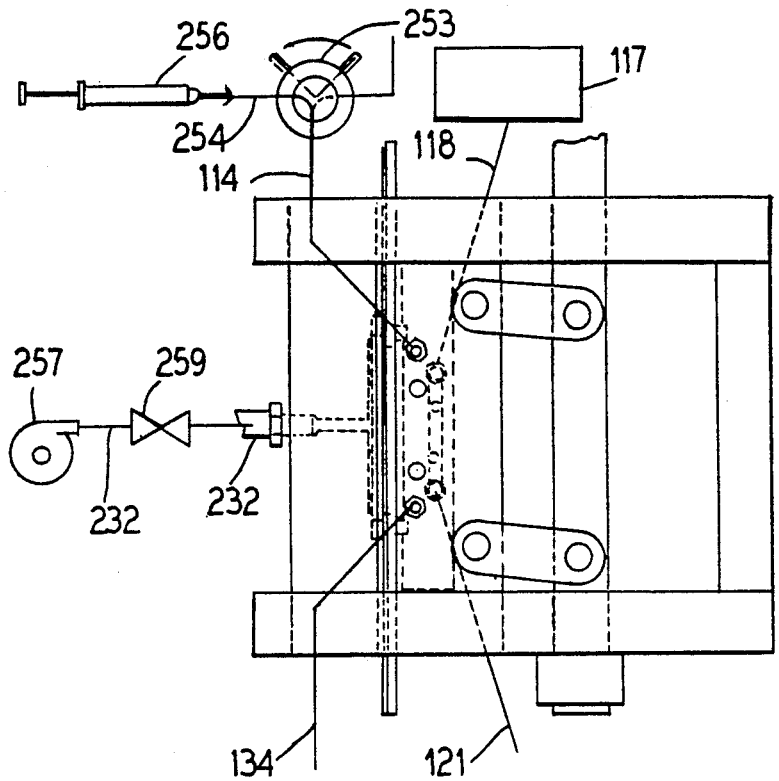
FIG. 16 is side elevational view showing an alternative embodiment of a slide processing chamber block assembly which is adapted for utilization of a slide structure of the type shown in FIGS. 14 and 15, such view including schematic representations of cooperation apparatus for slide pressurizing and for liquid injection means.
Figure 17:
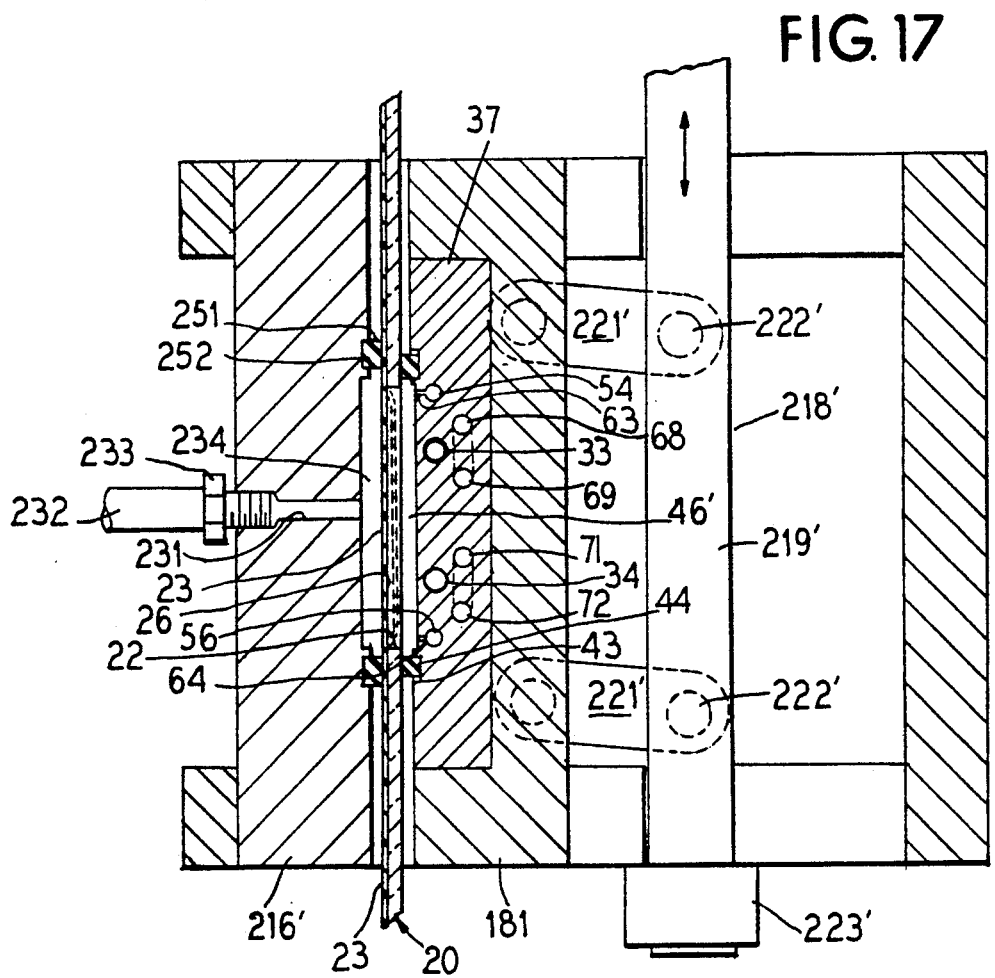
FIG. 17 is a vertical-sectional view taken along the line XVII—XVII of the station shown in FIG. 16.

The limit of movement of block 212 against the slide 217 is provided by frame 213 when the upper pair of links 221 abut into it. Members 213 and 223 have slotted guides for the legs of frame member 219. However, the links 221 are arranged to have traveled over center when the links 221 abut against the frame 213 so that toggle locking action is thereby achieved. Referring to FIGS. 16 and 17, there is seen another embodiment 229 of a slide processing station which is provided by the present invention and which is useful in sequential multi-step processing apparatus of the present invention as described herein. Station embodiment 229 is particularly adapted for use with a slide structure 20 such as hereinabove described. Station embodiment 229 incorporates a block member and container-like housing which are each comparable to block member 37 and housing 151. A accordingly, for convenience, each is similarly numbered, and similar respective components thereof are identically numbered for present identification purposes.

Station embodiment 229 incorporates a frame structure and a toggle mechanism which can each be structurally and functionally similar to those incorporated into slide processing station 211, and, accordingly, such components are similarly numbered, but with the addition of prime marks thereto for present identification purposes. Operation of the toggle mechanism 218' is comparable to that of toggle mechanism 218 in station embodiment 211.

The transparent block 216' at a central location thereof is provided with a channel 231 which normally extends therethrough and which is engaged with a fluid transfer line or conduit 232 by means of a threaded coupling 233 engaged therewith. Block 216' may also be provided with a shallow recess or cavity 234 in the interior face thereof. In adjacent outwardly spaced relationship to the perimeter of cavity 234 a channel 251 continuously extends; and seated in channel 251 is a fluidic sealing gasket 252. Gasket 252 is conveniently comprised of a suitable elastomer and can have a durometer value in the range of about 20 to about 50 although larger and smaller values can be used if desired.

Between block 216' and block 37 is mounted a slide 20 which has a specimen material coating (not shown) on the inside surface 26 of its layer 23 in the region of aperture 22. The outside surface portions of such layer 23 can be, if desired, in adjacent contacting relationship to surface portions of block 216' except in the region of the cavity 234. Thus, when the toggle mechanism 218' is in its closed position, a chamber 46' exists between slide layer 23, gasket 43 and block member 37, and a chamber exists between slide layer 23, gasket 252 and block 216' in the region of cavity 234. The perimeter dimensions of the aperture 22 are preferably smaller than or equal to the perimeter dimensions of the cavity 46' and also are preferably smaller than the perimeter dimensions of the cavity 234. Cavity 234 is generally preferably aligned with the chamber 46'.

Fluids for processing purposes are passed through chamber 46' in a manner comparable to chamber 46 of station embodiment 36 utilizing channels 54 and 63 and channels 56 and 64. If and when it is desired to treat the inside surface 26 of layer 23 with a small amount of a liquid, such as an aqueous composition of a probe, or the like, then, after a predetermined preliminary processing (which can be multi-step sequence) wherein fluids are moved through chamber 46' with the chamber 46' having the configuration shown generally in FIG. 17, for example, the 3-position valve 253 is switched in conduit 114. Thus, conduit 114 is closed and a conduit 254 is opened. The conduit 254 is in functional association with a hypodermic type syringe 256. A desired small volume of liquid is injected into conduit 254 from syringe 256 and passes successively through conduits 254 and 114 into chamber 46'. Then a pressurized substantially inert fluid, preferably a gas, such as air, nitrogen, or the like, is charged to conduit 232 from compressor 257 upon the opening of a valve 259 (which can be a solenoid actuated open/close valve), and such pressurized fluid passes into cavity 234. The pressure of the fluid so admitted into cavity 234 is selected to be sufficient to move the layer 23 of slide 20 towards the block 37, thereby increasing the volume of cavity 234 and decreasing the volume of chamber 46'. The amount of movement so achieved is selected to be sufficient to result in a final volume for chamber 46' which is about equal to the volume of liquid input into chamber 46' from syringe 256. Preferably, this reduced final volume for chamber 46' is less than about 20 microliters, although larger and smaller volumes can be used, if desired. As chamber 46' is reduced in size, the displaced gas in chamber 46' moves into channels 63 and 64 and out of block 37 through channels 54 and 56.

The temperature of block 37 can be regulated before, during, and after the residency of such injected liquid in the thus size reduced chamber 46', as above described in relation to station embodiment 36.

After such so injected liquid is redistributed by a change in volume of chamber 46' which is preferably sufficient to achieve liquid spreading which is preferably sufficient to substantially cover the inside surface 26 of layer 23 in the region of aperture 22, such so injected liquid can be maintained in such reduced size chamber for a desired time period, such as is accomplished during incubation in situ hybridization.

Thereafter, the fluid pressure in cavity 234 can be reduced so as to allow the layer 23 to return to its starting configuration in slide 20, and then fluid flow through the now enlarged chamber 46' can commence, allowing carrying out a washing step sequence or the like as desired.

Figure 18:
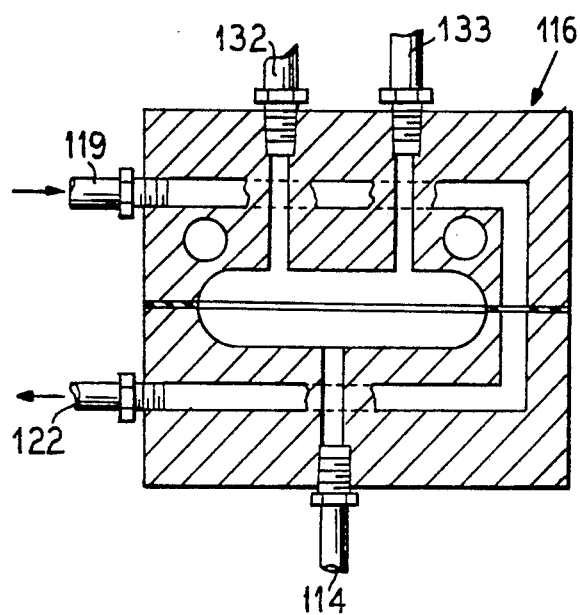
FIG. 18 is a cross-sectional view taken through one embodiment of a slide processing chamber delivery reservoir employable in combination with a slide processing station in apparatus such as shown in FIG. 1.

Shown in FIG. 18 is a cross-sectional view through one embodiment of a slide processing chamber delivery reservoir 116. While the components and operation of such reservoir 116 are hereinbelow described in reference to FIGS. 19-22, it will be appreciated that it is presently preferred to form the reservoir 116 of heat conducting metal, aluminum being presently preferred. Conveniently, the reservoir 116 is machined in two halves which are then clamped together. The halves can be formed lengthwise or crosswise. A gasket (not shown) can be positioned between the halves during assembly for reservoir cavity fluid sealing purposes.

Referring to FIG. 19, there is seen schematically the structure of a single processing station module 141 that is suitable for use in sequential multi-step processing apparatus such as is provided by this invention. The station 112 can be in any convenient form for providing a chamber within which specimen material can be held during processing in the apparatus. In the present illustrative embodiments, station 112 is adapted for processing of slide surface portions. Since the station module 141 is readily understood when placed in the context of the processing apparatus embodiment 111 shown in FIG. 20, the description of module 141 is combined with the description of apparatus 111 that is provided below.

From the foregoing description, it is seen that various embodiments of slide surface processing station apparatus are provided. Such apparatus characteristically incorporate block means for accommodating adjacently thereto one surface of a slide. Gasket means circumscribes a region between the slide and the block means to sealingly engage one with the other. By controlling the gasket size, the block structure, and/or the slide structure, the chamber volume of the chamber defined by the block, the gasket and the slide is controllable and can be variable if desired for a single combination of such members. Such apparatus includes releasable holding means that is adapted to hold and position a slide relative to the block means. Such apparatus further preferably includes temperature regulating means. Although the herein provided processing station structures are illustratively described as being used with slides which are generally elongated with a rectangular perimeter and are relatively thin in thickness, those skilled in the art will appreciate that other slide configurations can be employed and the processing station structures herein provided can be reconfigured for utilization therewith, if desired.

The slide surface processing station block assembly of this invention is readily adapted for use in combination with a processing station delivery reservoir which is adapted to deliver processing liquids thereto, and/or with a metering valve or pump means which is adapted to produce a controlled rate transfer and input of processing liquids thereto. A combination of such a slide surface processing station block assembly, a processing station delivery reservoir and a metering valve can coact together with functionally interconnecting elements and control means to comprise a basic unit or individual processing station module that is suitable for use as a subassembly in apparatus for the sequential step-wise processing of slide surface portions.

Apparatus: Sequential Multi-Step Processing

The present invention additionally provides apparatus suitable for carrying out sequentially a plurality (that is, at least two) process steps sequentially at one or more processing stations, and preferably at a plurality of processing stations. Each processing station preferably incorporates means for slide surface processing. Each such individual processing station can receive fluid selected from among any one of a predetermined plurality of fluid reservoirs. Such a selected fluid can be passed through the processing chamber at each individual processing station at a particular flow rate which is preferably predetermined and regulated. Optionally, but preferably, the temperature of each processing station and of process fluids input thereinto is individually controlled. Operations of such sequential processing apparatus relative to each such reservoir and to each such processing station thereof can be regulated by control means which can be computer driven.

Figure 20:
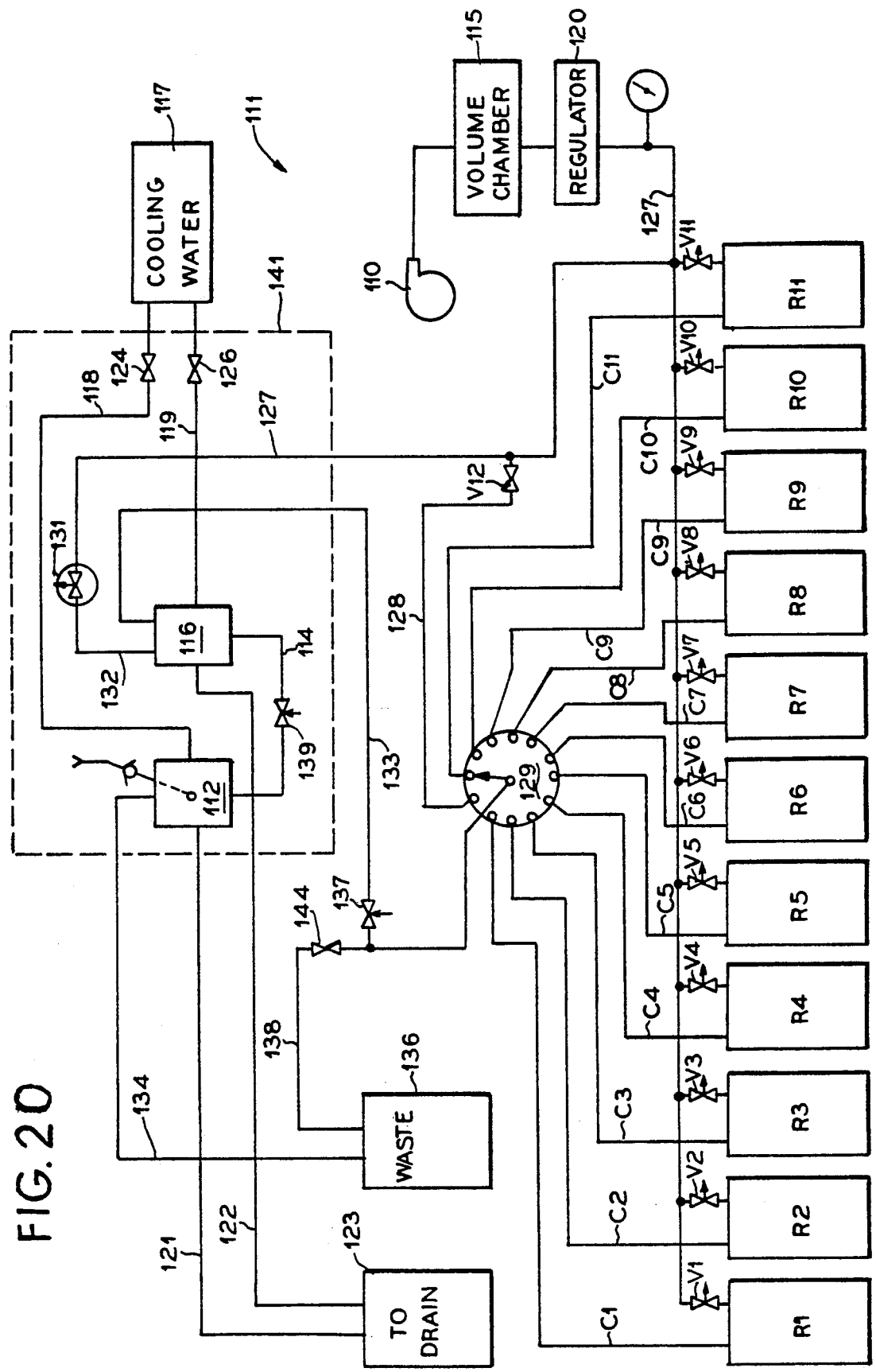
FIG. 20 is a schematic-type flow chart of one embodiment of a sequential multi-step processing apparatus which includes a plurality of supply reservoirs which incorporates a single processing station module, such diagram showing fluid transport only.

Referring to FIG. 20, there is seen an embodiment 111 of a multi-step sequential processing apparatus of the present invention that incorporates a single processing station 112 which is capable of having a fluid passed therethrough from any one of 11 supply reservoirs, each one thereof being designated for convenience as R 1 through R 11, respectively. Also, fluid from a common pressuring conduit or bus line 127 can be passed therethrough. The processing station 112 can have any desired or suitable structure or configuration, as those skilled in the art will appreciate. However, for purposes of practicing the presently preferred operational mode of slide surface processing, the apparatus 111 is preferably equipped with a slide processing station, such as one of the slide processing station embodiments hereinabove described or otherwise, if desired. A present preference is to employ the slide processing station embodiment 36.

FIG. 20 illustrates only the basic transport system for fluid movement to and through processing station 112 from reservoirs R 1 through R 11 and from common pressurizing conduit or bus line 127. Thus, FIG. 20 does not show details of electrical circuitry, such as is employed for operation, regulation and control of apparatus 111, and also FIG. 20 does not show structural details or operational features such as may be associated with any one or more of the individual subcomponents incorporated with apparatus 111. Also, modifications for apparatus 111 are not shown.

In apparatus 111, all processing fluids entering processing station 112 are charged thereto through a station supply conduit 114 which extends between and functionally interconnects the processing station 112 with a station input reservoir 116.

For reasons with achieving temperature control of reservoir 116 and of station 112, a temperature regulating fluid, preferably a liquid, such as water (presently preferred), a hydrocarbon, a glycol, or the like, is optionally but preferably independently circulated through each of station 112 and reservoir 116. Thus, in apparatus 111, coolant fluid from a pressurized coolant fluid reservoir 117 is charged through line 118 to station 112 and through line 119 to reservoir 116. A presently convenient and preferred pressurized coolant reservoir 117 comprises local tap water. Coolant fluid is discharged from each of station 112 and reservoir 116 through respective lines 121 and 122 which can both lead, as desired, to, for example, a collection reservoir 123 for recycle, a drain (sewer), a waste receptable, or otherwise.

Because apparatus 111 is intended for use in carrying out multi-step fluidic processing sequences in station 112, and because of the present preference to have both station 112 and reservoir 116 be temperature responsive, station 112 and reservoir 116 are each also preferably equipped with electric heating means (not shown in FIG. 20). The combination of such an electric heating means with a fluid coolant means enables an operator to produce relatively rapid increases or decreases in the temperature of station 112 and of reservoir 116. When, for example, the temperature of the coolant fluid being input into station 112 and reservoir 116 is substantially fixed (that is, regulated at a value within a preset range, or the like), then flow of coolant fluid to each of station 112 and reservoir 116 through respective lines 118 and 119 is regulatable by variable fluid flow control valves 124 and 126, respectively, in lines 118 and 119 using, for example, conventional process control feedback loops and remotely adjustable temperature sensors in station 112 and reservoir 116 (not shown in FIG. 17), or the like, as desired.

The reservoir 116 permits temperature regulation of all fluids, especially liquids, being input into station 112. Also, the reservoir 116 permits regulation of flow rate of all fluid dispensed from reservoir 116 into station 112 through line 114, using valve 139 as is explained hereinbelow.

In apparatus 111, each of the reservoirs R 1 through R 11 is selected for use in holding a different process liquid to be used in multi-step sequential processing while the pressurizing fluid employed in bus line 127 is selected to be a gas which is preferably or typically substantially inert as regards both material being processed in station 112, as well as process liquids in the reservoirs R 1 through R 11. Examples of suitable pressurizing gases include air, nitrogen, argon, or the like. Although the pressurizing gas can be a commercially purchased pressurized gas in a cylinder equipped with a pressure reducing valve (not shown)., or the like, it is presently preferred to equip apparatus 111 with a small air compressor 110 which charges compressed air to a volume chamber 115 that is equipped with a pressure reducing and regulating valve 120 from which connection is made to bus line 127.

Gas pressure in bus line 127 is maintained at a desired relatively constant pressure which is relatively low. Pressures in the range of about 3 to about 9 psi (pounds per square inch) are presently preferred for bus line 127. Compressed gas is thus charged through the common interconnecting pressurizing conduct or bus 127 to each of thirteen valves provided in embodiment 111 comprising one on-off valve, each being designated for convenience as V 1 through V 11, associated with each respective reservoir R 1 through R 11, one further on-off valve V 12, and a variable valve 131. Each valve V 1 through V 11 communicates directly with its associated reservoir R 1 through R 11 while valve V 12 communicates through a valve conduit 128 with an input position of a 12-position conduit switching valve 129.

In embodiment 111, valve 129 functions as a fluid distribution valve enabling one to join each one of the reservoirs R 1 through R 11 with the reservoir 116. Valve 129 is preferably a rotary-type as is now further explained. Valve 129 is a multiple position valve structure having a plurality of input ports which individually and separately interiorly connect with a single output port. Valve 129 thus incorporates means for remotely adjustably interconnecting individual valve input ports with such valve output port.

In particular apparatus 111 for valve 129 employs a twelve-position valve of the rotary type which has a step solenoid actuated core and control means (not shown in FIG. 20). Valves V 1 through V 12 in apparatus 111 are each preferably solenoid actuated and adapted to be either in the open or the closed position (means not shown in FIG. 20). Valves V 1 through V 12 are each preferably biased in a normally closed position.

Preferably, each of the valves V 1 through V 11 is of the three way type, so that when such a valve is closed after being opened to bus line 127, it vents to the atmosphere on the side thereof which is associated with its respective reservoir R 1 through R 11. Thus, the interior of the respective associated reservoir R 1 through R 11 that is associated therewith is vented to the atmosphere when the associated respective valve V 1 through V 11 is closed. Atmospheric venting can be adjusted to occur at a desired rate; however, it is preferred that each reservoir R 1 through R 11 vent rapidly and as soon as possible after its associated respective valve V 1 through V 11 is closed. Valve V 12, however, is of the two way type and does not similarly vent when closed after being opened.

The thirteenth valve that is connected to bus 127 in apparatus 111 is a pressurizing gas flow rate regulating pumping valve 131 that is directly associated with the reservoir 116 by a conduit 132. Those skilled in the art will appreciate that in place of the 12-position valve 129, valves of higher and lower conduit input position and switching capacity may be employed, if desired, so that the apparatus 111 would then be capable of operating with more or less than eleven storage reservoirs and one pressurizing fluid source. However, the apparatus 111 employs a single valve 131 for the combination of the station 112 and the reservoir 116. Pressurized gas flow through regulating valve 131 is electrically controllable (means not shown in FIG. 20) when valve 131 is opened to bus line 127. Valve 131 is also of the three way type so that when valve 131 is closed to bus line 127, it is open to the atmosphere on the side thereof which is connected with conduit 132.

The center or common output port of valve 129 is interconnected by delivery conduit 133 to reservoir 116. Supply conduits, each one designated for convenience as C 1 through C 11, respectively, interconnect each one of the reservoirs R 1 through R 11 with a different input feed position of valve 129. A feed conduit 128 interconnects valve V 12 with the twelfth and last input feed position of valve 129.

Thus, whenever, whether by operator actuation or by computer actuation in accordance with a program, as hereinbelow described, a given reservoir valve, such as, for example, valve V 1 of reservoir R 1, is actuated to an open position (from a preferably normally closed position), and also, the 12-position valve 129 is configured so that the liquid pathway therein from the conduit C 1 is opened, to delivery conduit 133, then liquid can flow successfully from such associated reservoir (in the present example, reservoir R 1) through valve 129 and conduit 133 into reservoir 116. The fluid flow thus produced is directly proportional to the gas pressure associated with bus line 127.

To regulate fluid flow in conduit 114, and to retard or prevent fluid charged from valve 129 into reservoir 116 from passing directly through reservoir 116 and on into and through station 112, line 114 is provided with a needle valve 139 which is conveniently manually adjustable or setable. Also, delivery conduit 133 is provided with a needle valve 137 which regulates fluid flow therethrough.

The valves V 1 through V 12 are necessary in the present combination with valve 129 for purposes of achieving operation of apparatus 111 as can be seen by the following operational description. For example, valves V 1 through V 12 are useful in avoiding fluid spurts or discharges in the apparatus 111 valve and conduit system, such as would tend to occur when the valve 129 is being positioned from one interconnection to another, if fluid communication between each of the individual reservoirs R 1 through R 11 with the valve 129 were not controllable by means of such valves V 1 through V 12. Such spurts are undesirable because they could contaminate a fluid in a supply reservoir R 1 through R 11 or they could contaminate the fluid contents in reservoir 116 resulting in the passage of an undesired fluid through station 112.

From station 112, fluid exits through conduit 134 into a waste receiver 136 or otherwise, as desired.

Valve 144 is a two position valve located in conduit 138. Conduit 138 interconnects with conduit 133 before check valve 137, and conduit 138 feeds into waste receiver 136. Valve 144 is preferably solenoid actuated and is normally closed. When open, valve 144 delivers fluid which passes through conduit 138 into waste receiver 136. Valve 144 is particularly useful in start up conduit purging, as hereinafter described.

After a desired multi-step sequence of processing steps has been carried out at the station 112, the apparatus 111 can be employed for accomplishing another replication of the same step sequence or a different sequence. For such another sequence, the material undergoing multi-step processing in station 112 can be replaced with a new or different material, such replacement being accomplished in station 112 manually or automatically (means not shown in FIG. 20).

In its operation, apparatus 111 can be considered to be characterized by the occurrence of three different operational apparatus step sequences, as follows: (a) a reservoir 116 liquid charging sequence for each station 112; (b) a reservoir 116 liquid discharging sequence for each station 112; and (c) a valve 131 gas input sequence through reservoir 116 for each station 112. These apparatus sequences are now described.

The operational sequence preferably employed in apparatus 111 for executing a particular reservoir 116 charging during a multi-step processing sequence is as follows (referring to FIG. 20):

Step 1. With valve 131 opened to its atmospheric vent position for conduit 132 and simultaneously closed for bus line 127, position (rotate) valve 129 so that interconnection therethrough is achieved between conduit 133 and one conduit selected from among the conduit group consisting of liquid supply conduits C 1 through C 11.

For example, conduit C 5 is interconnected with conduit 133 through valve 129.

Step 2. Since each respective one of the supply conduits C 1 through C 11 is associated with a different reservoir R 1 through R 11 that has its own respective pressurizing valve V 1 through V 11, the pressurizing valve of the reservoir which is associated with the supply conduit that was interconnected in Step 1 with valve 129 is now opened from its normally closed position to bus line 127. The opening of such one of the valves V 1 through V 11 results in the pressurizing of the process liquid in the affected respective associated reservoir R 1 through R 11 by the pressurizing gas applied thereto from the now connected bus line 17. The result is that the pressurized process liquid in the pressurized reservoir is effectively pumped into the associated interconnected conduit and passes through valve 129 into conduit 133.

Continuing the example, valve V 5 is opened so that pressurizing gas from bus line 127 enters reservoir R 5, pressurizes the gas space over the level of the process liquid therein sufficiently to cause the process liquid to leave its reservoir R 5 and to enter conduit C 5 and travel through valve 129 into conduit 133.

Step 3. Reservoir 116 receives a measured charge of process liquid from the thus selected one of the reservoirs R 1 through R 11. Immediately after such a progressive opening of valve 129 and one of the valves V 1 through V 11, a time interval transpires during which (a) the connected one reservoir of the reservoirs R 1 through R 11 becomes pressurized, and (b) process liquid from the reservoir fills the activated supply conduit (one of C 1 through C 11) and the delivery conduit 133 before process liquid begins to charge (enter) into the reservoir 116. This time interval is measurable (estimatable), and can be likened to a system constant. Thereafter, the total quantity of such a selected process liquid from such a given reservoir is charged to the reservoir 116. The charging is metered by elapsed time (preferred), by a conventional valved sample loop, or by some sensing means (such as a weight sensing transducer, a level controller, or the like, all not shown).

During the charging of reservoir 116, the pulse width modulated variable flow rate pumping valve 131 is in its normally closed or inoperative configuration and also such valve 131 is vented to the atmosphere so that conduit 132 and reservoir 116 are maintained at atmospheric pressure. Thus, as reservoir 116 fills with process liquid, air (gas) in reservoir 116 is displaced and exits mainly through valve 131. During this step, valve 131 is receiving no energizing pulse width modulation control signal Also, during this step, the needle valve 139 in conduit 114 remains open, but the flow therethrough of fluid from reservoir 116 to station 112 is regarded as negligible owing to the set point of valve 139 and the total time duration used for the charging of the reservoir 116.

As a present operational preference, it is preferred that the maximum amount of process liquid charged to reservoir 116 in any given charging be less than about 50 percent of the total reservoir 116 volume. If the amount of such process liquid called for is less than about 50 percent of the total reservoir 116 volume, then only such lesser amount is transferred in the reservoir 116.

Continuing the example, a metered quantity of process liquid in the reservoir R 5 is transferred into the reservoir 116. When, for example, the chamber in the processing station 112 has an operating volume of about 200 $\mu$l, and the reservoir 116 has an operating volume of about 2 ml, the reservoir 116 is preferably charged with not more than about 1 ml of process liquid.

Step 4. When such a metered transfer of process liquid into reservoir 116 from a given reservoir R 1 through R 11 is completed, then the open one of the valves V 1 through V 11 is closed. When such valve is closed relative to bus line 127, then that valve opens (vents) to the atmosphere, thereby promptly depressurizing both the pressurized reservoir and the interconnected supply conduit (one of C 1 through C 11, as explained). However, the supply conduit remains charged with the process liquid.

Continuing the example, valve V 5 is closed, and reservoir R 5 and conduit C 5 are depressurized.

Step 5. Valve 129 is repositioned so that interconnection is achieved therein between delivery conduit 133 and pressurized gas supply conduit 128.

Step 6. Valve V 12 is opened, thereby admitting pressurizing gas from bus line 127 into conduit 128. Such gas passes through valve 129 and through conduit 133. The result is that valve 129 and conduit are purged of process liquid which is moved into reservoir 116. Such a conduit purge is completed in a relatively short time interval. Flow of pressurizing gas from reservoir 116 through conduit 114 and valve 114 is negligible.

Continuing the example, a purge time of about 2 seconds is presently preferred.

Step 7. Valve V 12 is closed, thereby stopping gas flow in conduit 128.

The reservoir 116 charging cycle is now completed and can now be newly commenced by repeating Steps 1 through 7 (above). In the case of the apparatus 111, wherein a single processing station 112 is employed, such a charging cycle is commenced after the reservoir 116 has been emptied (pumped out or nearly so) through the operation of valve 131.

In a situation where as here only one processing station 112 is employed, and where, after one charging cycle, the same charging cycle is to be repeated using the same process liquid, the purge operation can be eliminated, if desired, as when such an elimination will not adversely affect further metering of process liquid into the reservoir 116. In such an elimination, Steps 5, 6, and 7 can be bypassed (not performed), and Step 1 can be initiated following Step 5 after the reservoir 116 has been emptied to a predetermined extent. A purge is preferred when a succeeding charging cycle uses a different process liquid from the proceeding charging cycle to avoid potential contamination problems.

Two or more process fluids can be transferred to the same reservoir 116 of a module 141 before valve 131 is actuated and conduit 132 is closed to the atmosphere. The splashing action of successively introduced liquids is believed to be sufficient for purposes of achieving liquid mixing.

The operational sequence preferably employed in apparatus 111 for executing a particular reservoir 116 pump down or discharging through a station 112 in a multi-step processing sequence is as follows (referring to FIG. 20):

Step 1. After Step 7 of the above described reservoir 116 charging sequence is completed, then valve 131 is closed to atmospheric pressure and conduit 132 can then communicate through valve 131 with pressurizing gas bus line 127.

Step 2. Variable flow rate pumping valve 131 is modulated with a predetermined pulse width modulated electrical signal so that pressurized gas from bus line 127 is discharged therethrough into conduit 132 and reservoir 116 at a desired pulsed rate which produces a desired pumping rate of process liquid from reservoir 116 through conduit 114 through valve 137 into and through station 112. As liquid is discharged from reservoir 116, the quantity of liquid remaining in reservoir 116 declines. The quantity of liquid remaining in reservoir 116 can be metered by elapsed time (preferred), by a conventional valved sample loop, or by some sensing means (such as a weight sensing transducer, a level controller, or the like, all not shown). After the quantity of liquid has declined to a predetermined level (including the empty level), or when the reservoir 116 is not only emptied of liquid but also the line 114 likewise, so that the reservoir 116 and the line 14 are, in effect, purged, the reservoir 116 and the line 114 are ready for a new and perhaps different process liquid (as part of some chosen multi-step processing sequence for station 112). The effective pumping rate produced by the operation of valve 131 is independent of, and not related to, the rate at which the charging Step sequence (above described) is carried out.

Step 3. Valve 131 is shut off (i.e., the actuating pulse width modulation thereof is terminated) and valve 131 is vented to the atmosphere. Thus, gas flow therethrough from bus line 127 is terminated, and reservoir 116 is depressurized via conduit 132 through valve 131 to the atmosphere, thereby making reservoir 116 available for receiving a new charge of process liquid such as is accomplished by the practice of Steps 1–7 of a charging sequence for reservoir 116 as above described.

The operational sequence preferably employed in apparatus 111 for executing a pressurizing gas flow from bus line 127 through reservoir 116 and station 112 is as follows (referring to FIG. 20):

Step 1. After Step 2 of the above described reservoir 116 discharging sequence is completed and the reservoir 116 and the line 114 are emptied of process liquid by the pumping action of valve 131, then valve 131 is further operated using a predetermined pulse width modulation so that pressurizing gas from bus line 127 continues to flow through line 132, reservoir 116, line 114 (and valve 139), and station 112. Maximum pressurizing gas flow rate is achieved maintaining valve 131 in a wide open configuration (i.e., the actuating electric signal is continuously applied to valve 131 without effective pulse width modulation). Alternatively, if valve 131 has previously been shut off and vented to the atmosphere after execution of Step 3 of the above described reservoir 116 discharging sequence then valve 131 is opened to bus line 127 and either (a) modulated with a pulse width energizing signal or (b) maintained in a continuous wide open setting.

Step 2. Valve 131 is shut off and vented to the atmosphere, thereby making reservoir 116 available for receiving a new charge of process liquid such as is accomplished by the practice of Steps 1–7 of a charging sequence for reservoir 116 as above described.

Opening of valve Y 12 with conduits 133 and 128 interconnected through valve 129 with valve 131 closed causes some pressurizing gas to enter the delivery conduit 133 and move successively into reservoir 116, conduit 114, station 112 and exit conduit 134 into waste receiver 136. However, the gas flow is lower than when the foregoing preferred procedure is used.

Particularly when the pressurizing gas is relatively dry or relatively free from liquid, moisture and other condensable volatiles, a flow of pressurizing gas to and through reservoir 116 and station 112 can serve to dry surface portions of material being processed in station 112, as desired in certain multi-step processing procedures.

Operation of the reservoir 116 and of the reservoirs R 1 through R 11 apparently do not require maintenance of a specific liquid level therein even though reservoir 116 preferably has at least about 100 times less volume (as a present operating preference) than the individual reservoirs R 1 through R 11. There appears to be little difference in the pumping rate between a nearly full and a nearly empty reservoir. Flow rate from reservoir 116 through conduit 114, for example, is limited by the pressurizing gas pressure in bus line 127, the inside diameter of the tubing employed for the various conduit 114, the orifice size of the connections for conduit 114, and the needle valve settings on needle valves 139. In the apparatus generally, liquid flow is proportional to the applied gas pressure.

In the apparatus 111, the combination of the processing station 112, the station input reservoir 116, the needle valve 139, and the flow rate regulating valve 131, together with temperature regulating means for each of the station 112 and the reservoir 116, fluidic conduits, electrical control lines, and suitable quick connect/disconnect terminal connection means (not detailed) can be considered to be a subassembly which is enclosed generally by the dotted line enclosing box 141 as marked, for example, in FIG. 20, and which for convenience is shown in a separated form in FIG. 20.

As indicated above, the subassembly 141 can, if desired, be regarded as a modular unit for use in apparatus of this invention. A present preference, however, is to utilize the station 112, the reservoir 116, the needle valve 139, and the conduit 114 as a replaceable module which is marked and identified by the dotted line enclosing box 141 in FIG. 19 or 20. Such a modular subunit has a separate housing and quick connect/disconnect fluidic and electrical line means (not shown). As those skilled in the art will readily appreciate, the structure of a given replaceable module 141 can vary. It is presently preferred that a module 141 be adapted for slide surface processing and that such unit employ a station corresponding to embodiment 36 and a reservoir corresponding to embodiment 116 (see especially FIG. 18).

Figure 21:
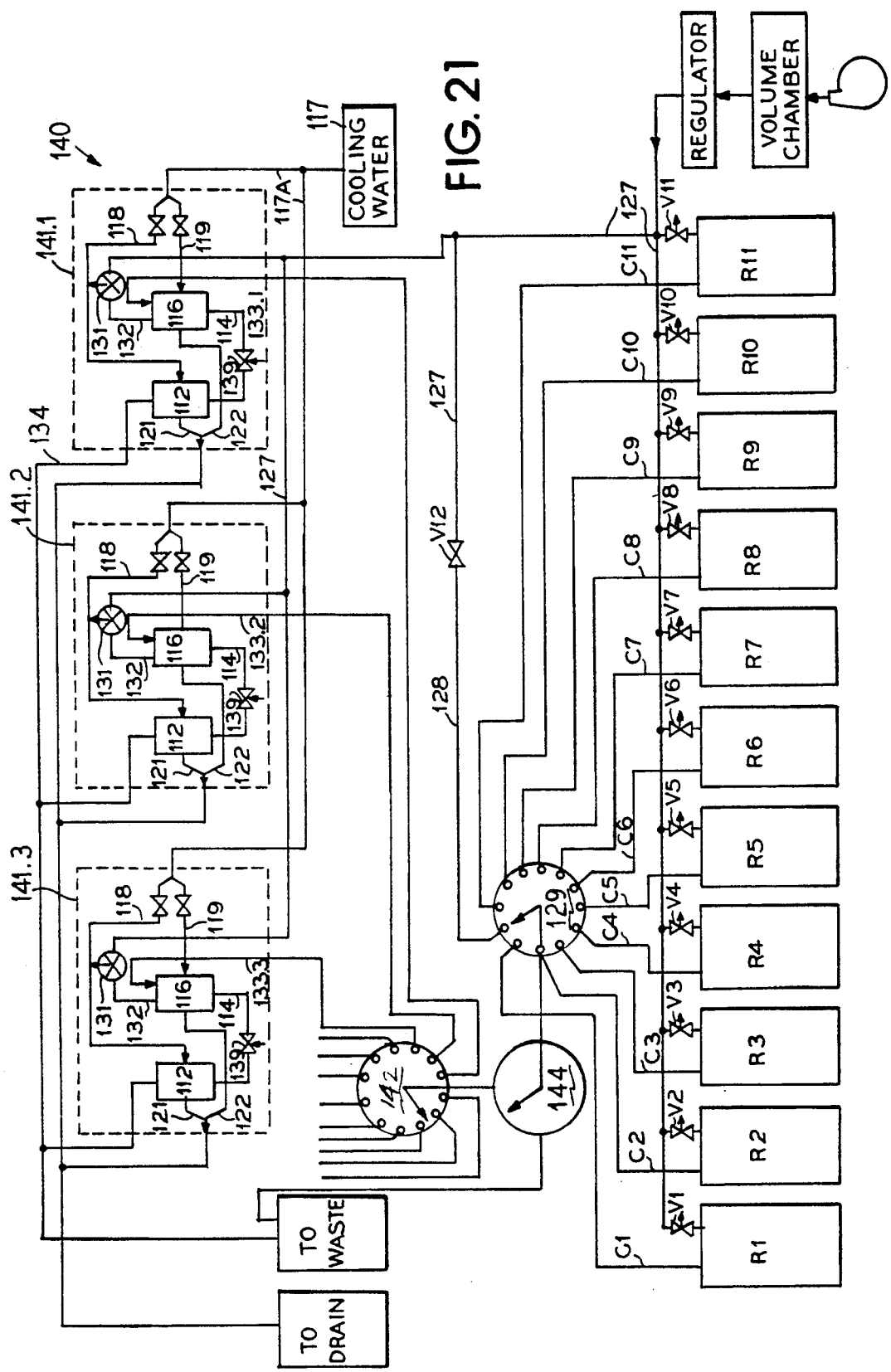
FIG. 21 is a schematic type flow chart which is similar to FIG. 20, but showing another such apparatus embodiment which incorporates a plurality of supply reservoirs and a plurality of processing station modules.

The type of apparatus illustrated by embodiment 111 is readily adapted for use with a plurality of such processing station subassemblies 141. An embodiment 140 of such multiple station apparatus is shown in FIG. 21. The apparatus 140 shown in FIG. 21 can be regarded as being similar to that apparatus 111 shown in FIG. 20. Similar components are similarly numbered for convenience and simplicity in understanding.

The embodiment 140 incorporates a plurality of 12 station subassembly modules each generally identified as 141, three of which are shown in FIG. 21 and which are individually designated as subassemblies 141.1 through 141.3 herein for convenience (subassemblies 141.4 through 141.12 not being shown). Also, each module 141 is provided with input coolant conduits 118 and 119, respectively, which independently supply coolant liquid to each of the station 112 and the reservoirs 116 thereof, and with output conduits 121 and 122, respectively. Both such input conduits 118 and 119 are branched from a common coolant delivery bus conduit 117A extending from coolant source 117 (such as tap water).

The reservoirs R 1 through R 11 in embodiment 140 are each connected as in embodiment 111 to a 12 position valve 129 via respective conduits C 1 through C 11, and pressurizing gas is chargeable to each reservoir R 1 through R 11 through a valve V 1 through V 11, respectively, that is associated therewith. Each valve V 1 through V 11 connects with pressurizing bus line 127. Valve 129 can receive pressurized gas through conduit 128 and valve V 12. Each subassembly module 141 is provided with its own flow rate regulating valve 131 which is individually interconnected with bus line 127 so that each valve 131 is maintained at the same static bus line pressure.

Each subassembly module 141 has its respective reservoir 116 delivery conduits 133 connected to a different feed position of a 12-position valve 142. While valve 142 is conveniently and preferably similar in structure and operation to valve 129, the operation thereof is reversed. Thus, the valve 142 is arranged to have a single input port and a plurality (twelve) of output ports with the rotary core thereof being solenoid actuated (means not shown in FIG. 21). The center or input port of the valve 142 is interconnected by intervalve conduit 143 to the center or output port of the valve 129 with a bleed valve 144 being functionally associated with conduit 143. Thus, in effect, a fluid distribution valve 129 is interconnected with a station distribution valve 142.

As a consequence, any one of the supply reservoirs R 1 through R 11, and also the bus line 127, can be individually interconnected with any one of the subassembly modules 141.1 through 141.12 via valves 129 and 142.

In its operation, apparatus 140 is characterized by the occurrence of three different operational step sequences, as follows: (a) a reservoir 116 liquid charging sequence for each station 112; (b) a reservoir 116 liquid discharging sequence for each station 112; and (c) a valve 131 gas input sequence through reservoir 116 for each station 112. The sequences are now described.

A perspective view of one embodiment of apparatus 140 is illustrated in FIG. 1. Each removable module 113 includes quick connect/disconnect line means, as above described. The operational status of each station module 141 is shown by status lights 245 on a review panel 246 located behind the row of station module 141. Individual pneumatic cylinders (not detailed) can be provided to operate a slide holder at each station block thereby to position a slide and also to change the volume of the individual block chambers 46. Illustrative computer access ports 247 are provided in one end of the apparatus housing 248. Bat handle type toggle switches 250 can be provided to control localized functions desired at each individual station 141.

The operational sequence preferably employed in apparatus embodiment 140 for executing at a particular station of the stations 141.1 through 141.12 a particular reservoir 116 charging a multi-step processing sequence is as follows (referring to FIG. 21):

Step 1. With valve 131 opened to its atmospheric vent position for conduit 132 and simultaneously closed for bus line 127, position (rotate) valve 129 so that interconnection therethrough is achieved between conduit 143 and one conduit selected from among the conduit group consisting of liquid supply conduits C 1 through C 11. Position (rotate) valve 142 so that interconnection therethrough is achieved between conduit 143 and one conduit selected from among the conduit group consisting of liquid delivery conduits 133.1 through 133.12 so that a conduit pathway is provided. It does not matter if valve 129 is so opened before valve 142; however, it is presently preferred to place valve 142 in position first. Valves V 1 through V 12 should not be opened until after valves 129 and 142 are set.

For example, with valve 131 venting to the atmosphere, supply conduit C 5 is interconnected with conduit 143 through valve 129 and conduit 133.2 is interconnected with conduit 143 through valve 142.

Step 2. Valve 144 is switched so that a through connection in conduit 143 results. Also since each respective one of the supply conduits C 1 through C 11 is associated with a different reservoir R 1 through R 11 that has its own respective pressurizing valve V 1 through V 11, the pressurizing valve of the reservoir which is associated with the supply conduit that was interconnected in Step 1 with valve 129 is now opened from its normally closed position to bus line 127. The opening of one of the valves V 1 through V 11 results in the pressurizing of the process liquid in the affected respective associated reservoir R 1 through R 11 by the pressurizing gas applied thereto from the now connected bus line 127. The result is that the so pressurized process liquid in the pressurized reservoir is effectively pumped into the associated interconnected conduits and passes through valve 129 into conduit 143 and through valve 142 into the delivery conduit selected.

Continuing the example, valve V 5 is opened so that pressurizing gas from bus line 127 enters reservoir R 5, pressurizes the gas space over the level of the process liquid therein sufficiently to cause such process liquid to leave its reservoir R 5 and to enter conduit C 5 and travel through valve 129 into conduit 143. Such pressurized process liquid then passes through valve 142 and into delivery conduit 133.2.

Step 3. The reservoir 116 of the thus selected stations 141.1–141.12 receives a measured charge of process liquid from the thus selected one of the reservoirs R 1 through R 11. Immediately after the opening of valves 129 and 142, and the subsequent opening of one of the valves V 1 through V 11, a time interval transpires during which (a) the connected one reservoir of the reservoirs R 1 through R 11 becomes pressurized, and (b) process liquid from the one reservoir fills the activated pathway comprised of the supply conduit (one of C 1 through C 11) and the delivery conduit one of 133.1 through 133.12 before process liquid begins to charge (enter) into the reservoir 116. This time interval is measurable (estimatable), and can be likened to a system constant. Thereafter, the total quantity of the selected process liquid from the given reservoir is charged to the reservoir 116. The charging is metered by elapsed time (preferred), by a conventional valved sample loop, or by some sensing means (such as a weight sensing transducer, a level controller, or the like, all not shown). During such a charging of reservoir 116, the pulse width modulated variable flow rate pumping valve 131 of the selected station is in its normally closed or inoperative configuration. Also valve 131 is vented to the atmosphere so that both the conduit 132 of this selected station and the associated such selected station reservoir 116 are maintained at atmospheric pressure. Thus, as reservoir 116 fills with process liquid, air (gas) in reservoir 116 is displaced and exits mainly through valve 131. During this step, the selected station valve 131 is receiving no energizing pulse width modulation control signal. Also, during this step, reservoir 116 and the needle valve 139 in conduit 114 remain open, but the flow therethrough of fluid from selected station reservoir 116 to selected processing station block 112 is regarded as negligible owing to the set point of the selected station valve 139 and the total time duration used for the charging of the selected station reservoir 116. As a present operational preference, it is preferred that the maximum amount of process liquid charged to selected station reservoir 116 in any given charging be less than about 50 percent of the total selected station reservoir 116 volume. If the amount of the process liquid called for is less than about 50 percent of the total selected station reservoir 116 volume, then only the lesser amount is transferred in the selected station reservoir 116.

Continuing the example, a metered quantity of process liquid in the reservoir R 5 is transferred into the reservoir 116 of station 141.2. When, for example, the chamber in the processing station block 112 of station 141.2 has an operating volume of about 200 μl, and the reservoir 116 has an operating volume of about 2 ml, then the reservoir 116 is preferably charged with not more than about 1 ml of process liquid.

Step 4. When the metered transfer of process liquid into reservoir 116 from a given reservoir R 1 through R 11 is completed, then the open one of the valves V 1 through V 11 is closed. When the valve is closed relative to bus line 127, then that valve opens (vents) to the atmosphere, thereby promptly depressurizing both the pressurized reservoir and the interconnected supply conduit (one of C 1 through C 11, as explained). However, the supply conduit remains charged with the process liquid.

Continuing the example, valve V 5 is closed, and reservoir R 5 and conduit C 5 are depressurized.

Step 5. Valve 129 is repositioned so that interconnection is achieved therein between delivery conduit 143 and pressurized gas supply conduit 128.

Step 6. Valve V 12 is opened, thereby admitting pressurizing gas from bus line 127 into conduit 128. The gas passes through valve 129, through conduit 143, through valve 142, through the connected delivery conduit 133, and into the selected station reservoir 116. The result is that valves 129 and 142 and conduits 143 and 133 are purged of process liquid which is moved into selected station reservoir 116. The conduit purge is completed in a relatively short time interval. Flow of pressurizing gas from selected station reservoir 116 through conduit 114 and valve 139 is negligible.

Continuing the example, a purge time of about 2 seconds is presently preferred.

Step 7. Valve V 12 is closed, thereby stopping gas flow in conduit 128 through valve 142 and selected conduit 133.

The selected station reservoir 116 charging cycle is now completed and another charging cycle for another selected one station reservoir can now be newly commenced by repeating Steps 1 through 7 (above). In the case of the apparatus 140, wherein a plurality of processing station 141 are employed, a repeat charging cycle for a given selected station reservoir is commenceable after that station's reservoir 116 has been emptied (pumped out or nearly so) through the operation of the selected station valve 131.

Two or more process fluids can be transferred to a given selected station reservoir 116 before the selected station valve 131 is actuated and the selected station conduit 132 is closed to the atmosphere. The splashing action of successively introduced liquids into a given reservoir is believed to be sufficient for purposes of achieving liquid mixing.

The operational sequence preferably employed in apparatus 140 for executing a particular selected station reservoir 116 pump down or discharging in a multi-step processing sequence is as follows (referring to FIG. 21):

Step 1. After Step 7 of the above described reservoir 116 charging sequence is completed, then selected station valve 131 is closed to atmospheric pressure and conduit 132 then communicates through valve 131 with pressurizing gas bus line 127.

Step 2. The selected stations variable flow rate pumping valve 131 is modulated with a predetermined pulse width modulated electrical signal so that pressurized gas from bus line 127 is discharged therethrough into the selected station conduit 132 and reservoir 116 at a desired pulsed rate which produces a desired pumping rate of process liquid from reservoir 116 through conduit 114 through valve 139 into and through station block 112. As liquid is discharged from reservoir 116, the quantity of liquid remaining in reservoir 116 declines. The quantity of liquid remaining in reservoir 116 can be metered by elapsed time (preferred), by a conventional valved sample loop, or by some sensing means (such as a weight sensing transducer, a level controller, or the like, all not shown). After the quantity of liquid has declined to a predetermined level (including the empty level), or when the reservoir 116 is not only emptied of liquid but also the line 114 likewise, so that the selected station reservoir 116 and the line 114 are, in effect, purged, the selected station reservoir 116 and the line 114 are ready for a new and perhaps different process liquid (as part of some chosen multi-step processing sequence for station 112). The effective pumping rate produced by the operation of valve 131 is independent of, and not related to, the rate at which the charging step sequence (Steps 1–7 above described) is carried out.

Step 3. Selected station valve 131 is shut off (i.e., the actuating pulse width modulation thereof is terminated) and valve 131 is vented to the atmosphere. Thus, gas flow therethrough from bus line 127 is terminated, and selected station reservoir 116 is depressurized via the associated conduit 132 through selected station valve 131 to the atmosphere, thereby making selected station reservoir 116 available for receiving a new charge of process liquid, such as is accomplished by the practice of Steps 1–7 of a charging sequence for reservoir 116 as above described.

The operational sequence preferably employed in apparatus 140 for executing a pressurizing gas flow from bus line 127 through reservoir 116 and station 112 is as follows (referring to FIG. 21):

Step 1. After Step 2 of the above described selected station reservoir 116 discharging sequence is completed and the reservoir 116 and line 114 are emptied of process liquid by the pumping action of valve 131, then valve 131 is further operated using a predetermined pulse width modulation so that pressurizing gas from bus line 127 continues to flow through line 132, reservoir 116, line 114 (and valve 139), and station 112. Maximum pressurizing gas flow rate is achieved to maintain valve 131 in a wide open configuration (i.e., the actuating electric signal is continuously applied to valve 131 without effective pulse width modulation). Alternatively, if valve 131 has previously been shut off and vented to the atmosphere after execution of Step 3 of the above described reservoir 116 discharging sequence then valve 131 is opened to bus line 127 and either (a) modulated with a pulse width energizing signal or (b) maintained in a continuous wide open setting.

Step 2. Valve 131 is shut off and vented to the atmosphere, thereby making selected station reservoir 116 available for receiving a new charge of process liquid such as is accomplished by the practice of Steps 1–7 of a charging sequence for reservoir 116 as above described.

Opening of valve V 12 with conduits 143 and 133 interconnected through valves 129 and 142 with valve 131 closed causes some pressurizing gas to enter the delivery conduit 133 and move successively into reservoir 116, conduit 114, station block 112 and exit conduit 134 into waste receiver 136. However, the gas flow is lower than when the foregoing preferred procedure is used.

Particularly when the pressurizing gas is relatively dry or relatively free from moisture and other condensable volatiles, a flow of pressurizing gas to and through reservoir 116 and station 112 can serve to dry surface portions of material being processing in station 112, as desired in certain multi-step processing procedures.

The pumping rate from a reservoir R 1 through R 11 does not appreciably vary with the level of solution in the reservoir bottles R 1 through R 11, as indicated. There is, however, a time delay difference that is involved which is related to the reservoir fill level. For example, in pump tests each extending over a time interval of about 20 seconds, relatively standard reservoir output volumes were observed. However, when the tests each extended over a time interval of only about 4 seconds so that only about 1 ml of liquid was pumped, it was found that some variation in the volume of liquid so pumped resulted. This variation is apparently related to the reservoir fill level. To overcome such variations, a sample loop can be incorporated, if desired into an apparatus embodiment 140, or the like, as now described:

Referring first to FIG. 20, there is seen in apparatus embodiment 111 in the region of valve 129 a sample loop that is designated by an enclosed dotted line and that is herein designated in its entirety by the number 261 for convenience. Sample loop 261 employs in place of needle valve 137 in conduit 133, a two way openable/closable solenoid actuated valve 262, thereby breaking conduit 133 into two different sections which are identified for convenience as section 133A and section 133B. Section 133B extends between valve 262 and reservoir 116, and section 133A extends between valve 129 and valve 262 with the junction 263 of conduit 133A with waste conduit 138 just preceding valve 262. The volume of the interior passageway of conduit 133A is selected so as to have a predetermined value, such as, for example, one milliliter, between valve 129 and about junction 263. Observe that this apparatus configuration still permits the apparatus embodiment 111 to operate on a timed basis independently of use of the sample loop 261 for delivering a given a supply reservoir liquid to delivery reservoir 116, as above described; however, with needle valve 137 removed, the flow rate of liquids through conduit 133A and 133B with valve 262 open is more rapid than with needle valve 137 in place.

To operate the sample loop 261, the valve 262 is closed, and the solenoid actuated, openable/closable waste valve 144 is opened, thereby permitting liquid from a predetermined one of the reservoirs R 1 through R 11 to be pumped (charged or transferred) by opening its associated one respective valve V 1 through V 11 in the manner above described. Thus, liquid flows successively through one respective associated conduit C 1 through C 11, to valve 129, and then into conduit 133A. Such pumping is conveniently regulated by utilizing a pumping time interval which is sufficient for such liquid to pass through the one conduit C 1–C 11, the valve 129, fill conduit 133A, and travel past junction 263 into waste delivery conduit 138, and perhaps even past valve 144 in conduit 138. Then, such transfer from the chosen source reservoir is stopped (in the manner above described) by closing the open valve from among V 1 through V 11 that is associated with one source reservoir R 1 through R 11 from which the liquid has been pumped. At this operational point, one milliliter of liquid fills the measured volume of conduit 133A. Next, valve 262 is opened, valve 144 is closed, and valve 129 is switched (stepped) around to a position where the output conduit 133A is connected therethrough to pressurizing gas line 128. Valve V 12 is then opened causing pressurized gas in line 127 to enter line 128, pass through valve 129, and push the measured liquid volume in conduit 133A forwardly through conduit 133B and into reservoir 116.

Referring next to FIG. 21, there is seen of apparatus 140 in the region of valves 129 and 142 a sample loop that is designated by an enclosed dotted line and that is herein designated in its entirety by the number 266 for convenience. Sample loop 266 does not need valve 144 in conduit 143, so, in sample loop 266, this valve 144 is either eliminated or left in an open configuration in conduit 143 when the sample loop 266 is being used. Sample loop 266 uses one of the 12 output conduits coming from valve 142, and, for such purposes, one station of the 12 stations 141, for example, station 141.12, is eliminated (disconnected), and the conduit that was connected thereto from valve 142 is now reconnected to waste delivery reservoir 136 and is redesignated herein for convenience as waste delivery conduit 267. The internal volume of conduit 143 is sized so that it has a predetermined value, such as, for example, one milliliter, between valve 129 and valve 142. Observe that the apparatus configuration still permits the apparatus embodiment 140 to operate as above described on a timed basis for delivery of a given supply of reservoir liquid to a given station 141 delivery reservoir 116 independently of the use of the sample loop 266.

In apparatus 140, each one of the conduits 133.1 through 133.12 for each one of the twelve respective stations 141 incorporates its own needle valve 137.1 through 137.12, respectively.

To operate the sample loop 266, the valve 142 is indexed (stepped) around to a position where it interconnects conduit 267 with the waste receiver 136. Then, liquid from a selected and duly pressurized (in the manner above described) one of the reservoirs R 1 through R 11 is pumped (charged or transferred) through the appropriately set valve 129 and into and through the conduit 143. Some of this liquid is allowed to pass on through valve 142 from conduit 143 and enter into conduit 267. Such pumping is conveniently regulated by choosing a time interval which is sufficient for such liquid transfer to achieve not only a filling of conduit 143, but also at least a partial fillage of conduit 267. Then, such transfer from such chosen reservoir is stopped (in the manner above described). At this operational point, one milliliter of liquid fills the measured volume of conduit 143. Next, valve 142 is switched (stepped) around to a position where it is connected with a reservoir 116 delivery conduit 133 for a selected one of the stations 141.1 through 141.11. Also, valve 129 is switched (stepped) around to a position where it is connected with pressurizing gas line 127. The result is that the measured volume of liquid in conduit 143 is blown through valve 142, through the selected delivery conduit 133, and into the selected one station reservoir 116.

Thus, usage of either sample loop 261 or 266, as a particular apparatus configuration may indicate, permits one, if desired, to meter accurately controlled quantities of processing liquid into the reservoir 116 of a processing station module 141.

The type of apparatus illustrated by the embodiments 111 and 140 is also readily adapted for recycle of process fluids, if desired. Thus, as shown, for example, in FIG. 22, an embodiment 236 of multiple station, multiple reservoir apparatus is provided which has been modified (relative to apparatus 140) to include process liquid recycle capability. Like apparatus 140, apparatus 236 includes a plurality of 12 station subassemblies that are identified as 241.1 through 241.3 in FIG. 22 (assemblies 241.4 through 241.12 not being shown). For reasons of convenience, simplicity and ready comprehension, components in apparatus 236 which are similar in structure and function to corresponding components in apparatus 111 and 140 are similarly numbered.

Figure 22:
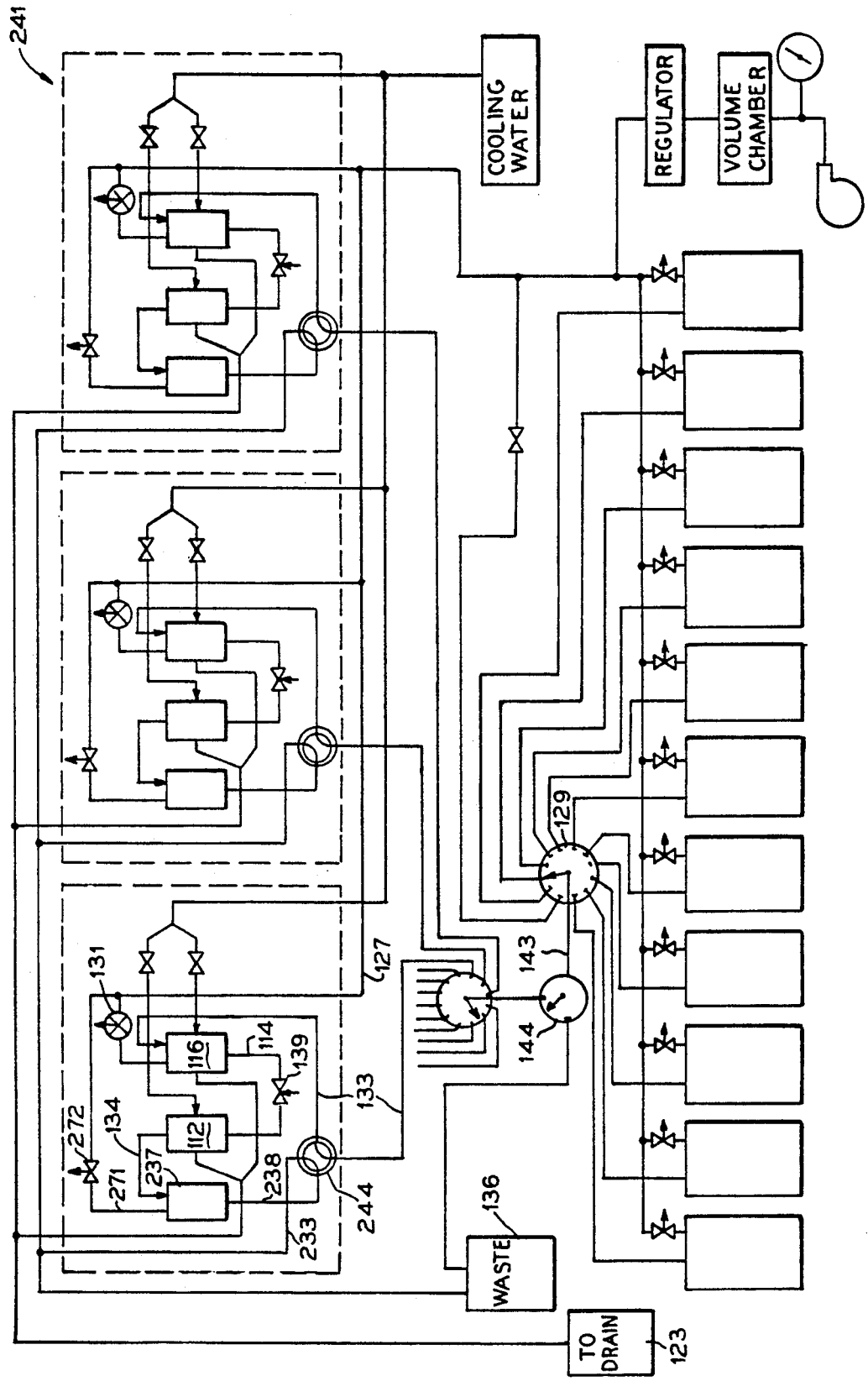
FIG. 22 is a schematic type of flow chart similar to FIG. 21, but showing another such apparatus embodiment which incorporates a plurality of supply reservoirs and a plurality of processing station modules which modules each incorporate additionally a recycle reservoir.

As in the case of the previous station modules or subassemblies 141, each of the present station modules or subassemblies 241 incorporates a processing block 112, a station input reservoir 116, and an interconnecting conduit 114 therebetween that is equipped with a needle valve 139. Also, the inputted processing liquid is charged into the reservoir 116 of each station 241 through a delivery conduit 133, there being, as in apparatus embodiment 140, a single such delivery conduit for each station 241, such delivery conduits being identified as 133.1 through 133.12, respectively, but only delivery conduits 133.1 through 133.3 are shown in FIG. 22. In each station 241, a charge of processing fluid is pumped from reservoir 116 to and through block 112 via conduit 114 by means of variable rate gas pulses input into reservoir 116 from a pulse width modulated valve 131 and associated pressurizing bus line 127. A pulse width modulated signal is applied to the solenoid of each valve 131. Cooling water (or other coolant liquid) circulates, as before, through conduit sets 118/121 and 119/122 and associated valves 124 and 126.

However, each station 241 is further equipped with a recycle receiver tank (or reservoir) 237 (identified individually as 237.1 through 237.12, respectively, for convenience). Each such reservoir 237 interconnects with the process liquid discharge conduit 134 from station block 112. Collected process liquid received in a recycle reservoir 237 can be returned to the originating one of the reservoirs R 1 through R 11 during a time interval when valves 129 and 142 in apparatus 236 are not involved with charging liquid from selected ones of reservoirs R 1 through R 11 to individual ones of the reservoirs 116 of individual stations 241.1 through 241.2, as now described below.

Each recycle reservoir 237 is connected with an output conduit 238 which interconnects with one input port of a two-position, four-port diverter valve 244 in each station 244. One output port of such valve 244 is connected to a waste delivery conduit 233 which connects with waste receiver 136. The delivery conduit 133 for each station 241 is connected across the second input port and the second output port of such valve 244. During operational charging and discharging of a reservoir 116, when recycle of process fluid is not contemplated, the valve 244 is in the configuration illustrated in FIG. 22 where input liquid travels successively through conduit 133 and through valve 244 into reservoir 116, and where fluid discharged from block 112 travels successively through conduit 134, recycle reservoir 237, conduit 238, valve 244, and conduit 233 on its way to waste receiver 136. However, when recycle of process liquid is contemplated, the reservoir 116 can be first charged with a predetermined quantity of process liquid, and then, at the time, for example, when valves 142 and 129 are being switched, valve 244 can be switched into its second position where conduit 133 is closed, conduit 233 is closed, and conduit 238 is connected with the input side of conduit 133. In this configuration, liquid in reservoir 237 can be pumped (discharge) successively through conduit 238, valve 244, and into conduit 133, as desired for recycle purposes.

Suitable diverter valves 244 are solenoid actuated and are adapted for computerized control in accord with the teachings of this invention. A suitable such valve 244, for example, is available commercially, from various manufacturers. Such valve is conveniently actuated by a 12 volt associated solenoid which steps the valve from one position to another.

Recycle reservoir 237 is connected via a conduit 271 to a two-position, three-way valve 272 which valve can be similar in structure and function to one of the valves V 1 through V 11. Valve 272, in turn, is connected on its input side to the pressurized gas bus line 127. When recycle is not being practiced, valve 272 is closed relative to bus line 127 and is vented to the atmosphere relative to line 271. When recycle is being practiced, valve 273 to open relative to bus line 127 and to conduit 271 (and thus is not vented); hence, recycle reservoir 237 is pressurized and liquid therein can be effectively pumped from recycle reservoir 237 into conduit 238.

When valve 142 is stepped (indexed) and set in a configuration where the particular conduit 133 (which is connected through valve 244 to conduit 238 and through which liquid is to be recycled from a given station 141) is interconnected with conduit 143, and also when valve 129 is stepped (indexed) and set in a configuration where conduit 143 is interconnected with a particular line from among conduits C 1 through C 11 which communicates with the originating (relative to the liquid being recycled) one of the reservoirs R 1 through R 11, then, with valve 272 open as described and line 271 pressurized, liquid in recycle reservoir 237 is transferred back to the starting one of the reservoirs R 1 through R 11.

Using the sample loop 266 with the recycle reservoir equipped apparatus 236 can aid in providing additional or longer time periods for using valves 142 and 129 for such recycle. Sufficient liquid from a given one of supply reservoirs R 1 through R 11 can be charged sequentially to the stations 141 to permit each such station to run for awhile. Also, with such sample loop, the restriction in the delivery conduit 133 for each station 141 induced by a needle valve, such as valve 137 in the embodiment 111, is removed, so liquid in the sample loop conduit 143 will move rapidly when pressurized through valve 142 into the selected station reservoir 116. Also, larger diameter conduits can be used which will result in accelerated flow rates of liquid therethrough. Even if a brief time delay is experienced in the execution of a given station's process step sequence, caused by, for example, recycling time, such delay apparently will not significantly interfere with the step processing, or the specimen material being processed in a given station, because the step sequence is part of a generally wet system which is not affected by a brief period of stand-by between or even during individual steps of a multi-step sequence, such as, for example, successive washing steps, or the like.

The computer-regulated operating sequence of the hereinbelow described control system provided by this invention is adjusted to provide and select suitable time intervals when rotatable, switching, step advanced, solenoid actuated valves 142 and 129 are not in service for process liquid charging purposes, and it is during these time intervals (as above indicated) that liquid in any one of the recycle reservoirs 237 of stations 141 is transferred back to the originating one of the liquid reservoirs R 1 through R 11. Optionally, and alternatively, liquid in a recycle reservoir 237 can be discharged into a designated receiving reservoir other than the originating reservoir (details not shown), if desired.

The operational step sequences for the apparatus 236 are similar to those for apparatus 140, but with the above indicated modifications being utilized when recycle equipment and operating conditions are employed.

Because the effective aperture size in the needle valves employed in an apparatus embodiment, such as apparatus 140, is small, it is presently preferred to use processing liquids and compressed gas which are substantially free from particulates. Such particulates can effectively result in plugging of the needle valve apertures. Filtering of processing liquids and compressed gas is desirable before such are introduced into apparatus of this invention. In addition, it is preferred to filter such liquids as they leave a respective reservoir R 1 through R 12.

In one convenient and exemplary embodiment, each one of the reservoirs R 1 through R 1 comprises a plastic or glass bottle which is fitted with a screw-on plastic cap. Each cap has circumferential internal threads which preferably matingly engage circumferential external threads formed in the bottle neck region adjacent the mouth thereof. Conventional container structures are conveniently employed for the bottle and cap. Each cap is provided with apertures therein, one for association with one of the valves V 1 through V 11 and the other for association with a dip tube which extends into the interior of each bottle when the cap is engaged therewith. A filter is conveniently provided at the exterior mouth of each dip tube in the region of the associated cap so that liquids exiting through the dip tube under the influence of pressurized gas being input into the reservoir through such valve are filtered before they enter one of the conduits C 1 through C 11. An air filter is conveniently located before or after valve V 12 in the direction of gas flow. A filter can be located in each conduit 114 preferably before valve 139 if such is employed on conduit 114. Additional conduit filters can be used if desired. Conventional fluid filters can be used for such purposes having pore sizes preferably below about 10 microns.

Although the filters act as conduit restrictions, they are helpful additionally in generally permitting each needle valve to be set at a larger aperture setting. Thus, the needle valve can handle larger particulates without line plugging. Loss of flow is thus minimized.

It is also possible to eliminate the valve 139 and to replace such with a restriction. For example, valve 139 can be replaced by a filter which acts like a restriction. Such a filter can be comprised of stainless steel frit-like particles which have been compacted and heated and as a result has a pore size, for example, under about 5 microns, or, more preferably, not more than about 2 microns or even smaller, but larger pore sizes can be used. The filter pore size, thickness, and cross-sectional area, are all significant factors when using such a filter as a restriction. Such a filter can be located in the conduit 134 leading fluid away from a process block 112. This location produces a longer time interval for block 112 fillage with process liquid which can be a desirable delay time. Gas which breaks through the liquid, however, passes on through the restriction rapidly at a rate which is much faster than is achieved by the liquid. In this operational mode, the filter is not primarily being used to filter particulates but rather for purposes of flow control.

In place of the pulse width modulated valve 131, one can employ a peristaltic pump, a piston pump, or some other type of positive displacement pump. With such a pump means, the gas pressurized pumping system hereinabove discussed can be replaced. Thus, a process liquid can be taken from each reservoir 116 and mechanically pumped though the station block 112.

Figure 33:
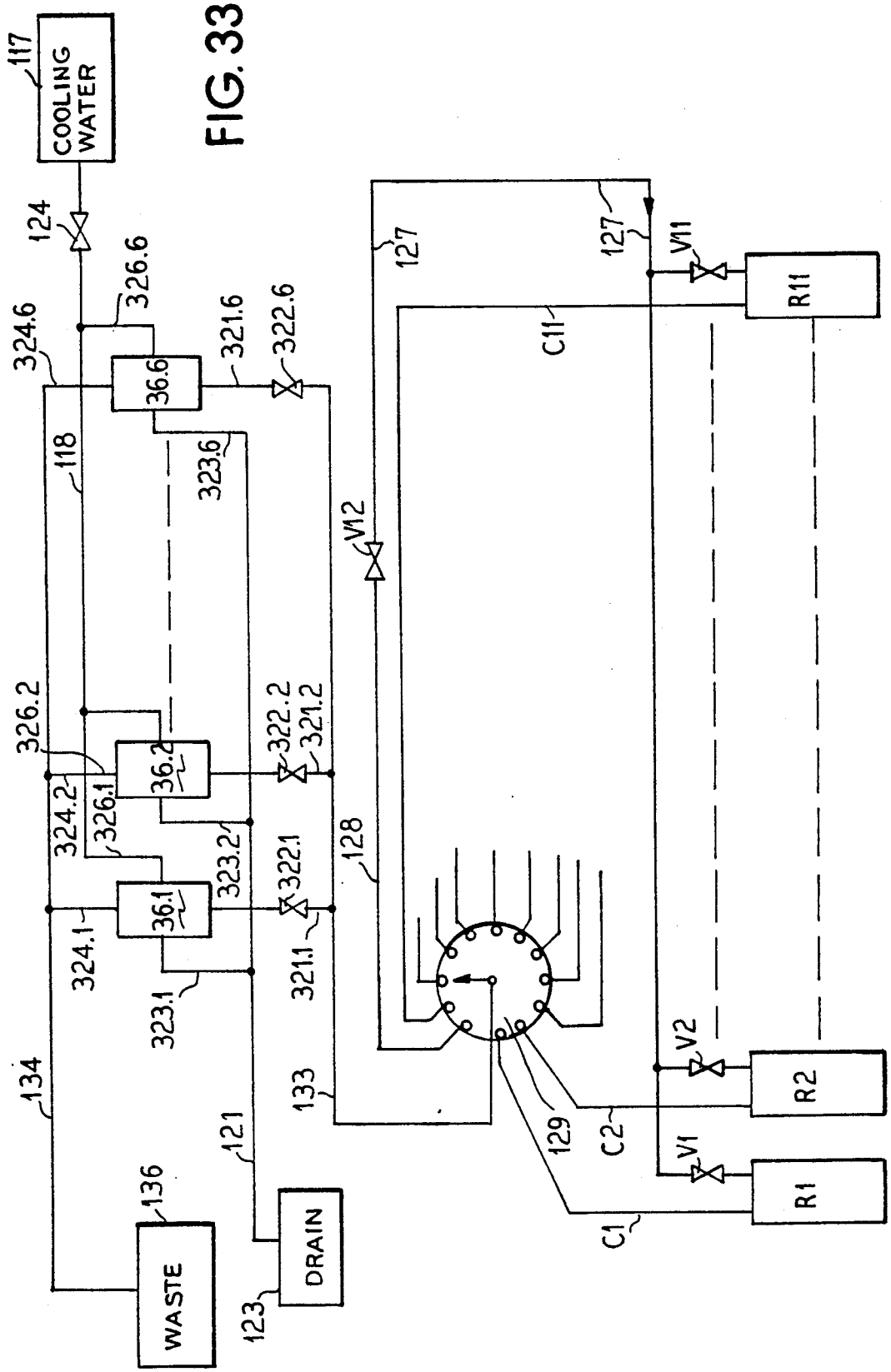
FIG. 33 is a schematic type of flow chart which is similar to FIG. 20, but showing another such apparatus embodiment which incorporates a plurality of supply reservoirs and plurality of station processing blocks.

Referring to FIG. 33, there is seen an embodiment 319 of a multi-step sequential processing apparatus of the present invention which incorporates a plurality of processing stations 36, or the like, herein illustratively six individual stations designated as 36.1 through 36.6 as well as a plurality of processing liquid supply reservoirs designated as R 1 through R 11, respectively. Pressurized gas from a common pressurizing conduit or bus line 127 can be charged to each reservoir R 1 through R 12 through a valve V 1 through V 11 that is adjacent each such respective reservoir. Each of the reservoirs R 1 through R 12 is interconnected with a different port of a rotary 12 input port, single outlet port valve 129. Also, pressurized gas from line 127 is chargeable through a conduit 128 to valve 129 through a valve V 12 that interconnects with bus line 127. Thus, in the operational manner of apparatus 111 or 140, processing liquid from one of the reservoirs R 1 through R 11, or gas from bus line 127 can be fed through valve 129 and into a delivery conduit 133 associated with the output port of valve 129.

The conduit 133 delivers fluid from valve 129 to individual feeder conduits that delivers fluid to each one of stations 36, each respective such feeder conduit being identified by the successive numerals 321.1 through 321.6. Each such feeder conduit 321 is provided with a needle valve 322.1 through 322.6, respectively, to provide a line restriction and flow control means. In place of needle valve 322, a filter, such as a filter that is able to trap particles below about 5 microns in size, can be used, if desired, which filter then functions both in its capacity to filter particulates and also as a line restriction. Alternatively, a combination of such a needle valve and such a filter may be employed in each such feeder conduit 321. Such devices are used to make fluid flow to each station 36 uniform.

Thus, processing fluid input into each station 36 flows therethrough and exits therefrom through a departure conduit 323.1 through 323.6, respectively. Each of the departure conduits 323 joins with waste conduit 134 which delivers effluents from each station 36 to waste receiver 136.

Hence, at each station 36, material being sequentially processed, such as a coating on a slide (not shown in FIG. 33), is subjected to the same processing procedure. If desired, a pause in the flow sequence can be produced, and during this pause, if desired, a probe containing liquid composition can be injected into the chamber of each station 36, followed by the resetting of the slide clamping mechanism to achieve a reduced chamber 46 volume, as hereinabove described, with the final position of the holder assembly being as illustrated, for example, in FIG. 4C. After a suitable or desired incubation period, the holder assembly can be reset, the chamber 46 enlarged, and a further or subsequent processing step sequence undertaken, as hereinabove described.

Temperature of each station 36 can be regulated with cooling water from a source 117 through a valve 124, or the like, that is input to each station 36 through input conduits 326.1 through 326.6 feeding from conduit 118. Electric heating means can be used, if desired. A temperature controller whose set point is manually adjustable can be employed at each station 36 to control the applied electric current, if desired. Output waste water from each station 36 can be channeled through collector conduits 324.1 through 324.6 and into drain conduit 121.

Because of the simple structure of apparatus 319, manual control of the valves can be used.

Figure 34:
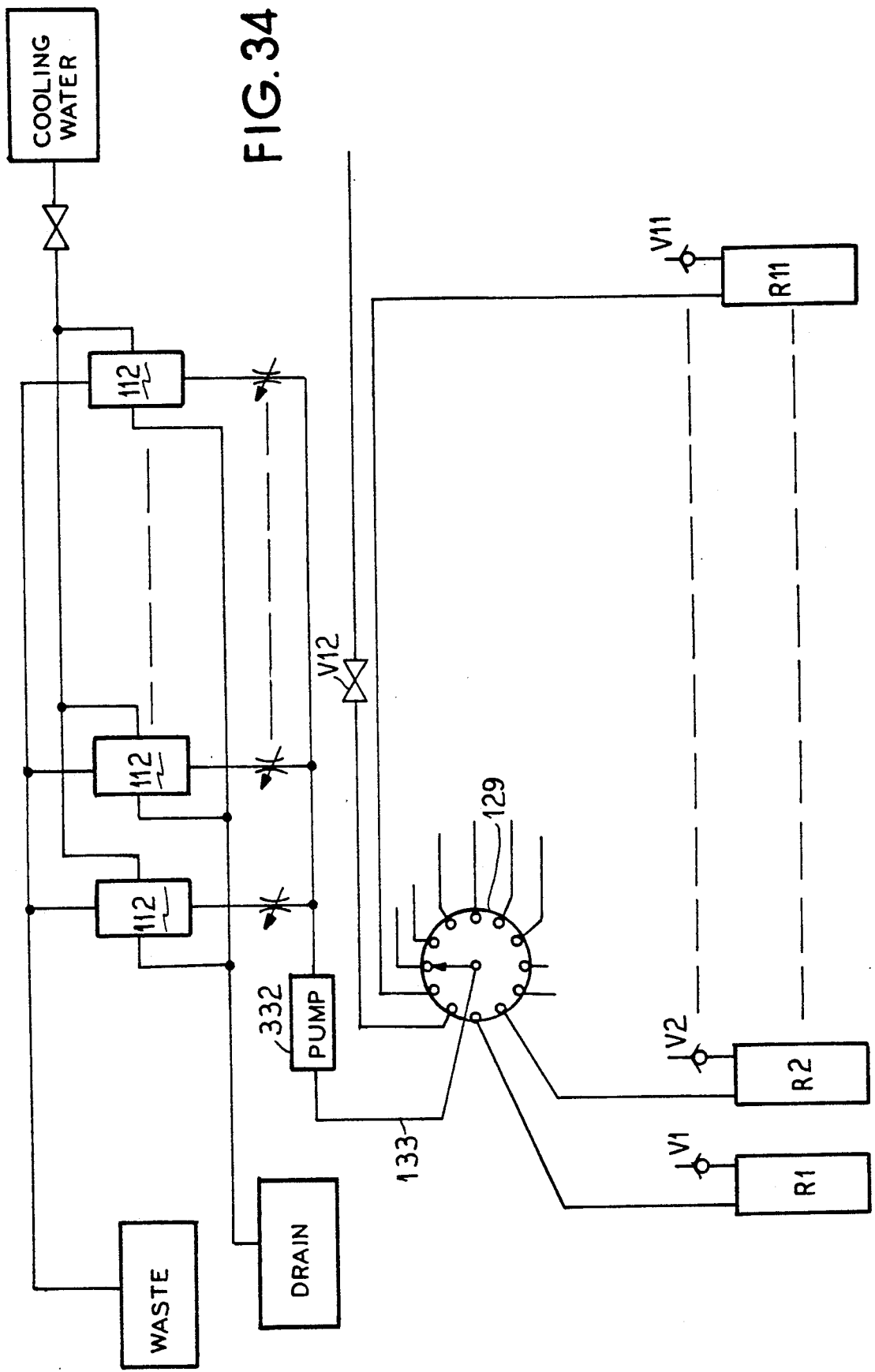
FIG. 34 is a schematic type of flow chart which is similar to FIG. 20, but showing another such apparatus embodiment which incorporates a plurality of supply reservoirs and a plurality of station processing blocks.

Referring to FIG. 34, there is seen an embodiment 329 of another multi-step sequential processing apparatus of the present invention that incorporates a plurality of processing stations 36, or the like, herein illustratively six, individually designated as 36.1 through 36.6, as well as a plurality of processing liquid supply reservoirs designated as R 1 through R 11, respectively.

Each of the reservoirs R 1 through R 11 is provided with a check valve 331.1 through 331.11, respectively, by which atmospheric air can enter into the associated reservoir, but not leave. Also, each of the reservoirs R 1 through R 11 is provided with an output conduit identified as C 1 through C 11 which interconnects with a 12 input port, single outlet port valve 129.

A conduit 133 is associated with the output port of valve 129 and conveys liquid from valve 129 to individual feeder conduits that delivery fluid to each one of the stations 36, each respective feeder conduit being identified by the successive numerals 321.1 through 321.6. Each such feeder conduit 321 is provided with a needle valve 322.1 through 322.6, respectively. As in the case of apparatus 319, the valves 322 may be replaced with a filter or other restrictions, or may be used in combination with such.

Fluid separation and removal from each station 36 is accomplished similarly to the manner used in apparatus 319. Temperature regulation can likewise be similarly accomplished. A given process liquid can be manually charged and removed from the stations, if desired.

To transfer liquid from a reservoir R 1 through R 11 through valve 129 and then to and through each station 36, a positive displacement pump 332, such as a piston pump, a peristaltic pump, or the like is installed in line 133 between valve 129 and the start of the feeder conduits 321.1 through 321.6. When the valve 129 is interconnected with a selected one reservoir R 1 through R 11, liquid from such reservoir is drawn successively through the associated one of conduits C 1 through C 11, and valve 129, and into conduit 133. After passing through pump 332, the liquid is input into and passes through each station 36.

If an input of compressed gas into the station 36 is desired, then such can be input through line 128 from pressurized line 127 by opening valve V 12.

While a twelfth reservoir R 12 can be employed for interconnection with valve 129 through a conduit C 12, it is now preferred to reserve the twelfth port of the 12 position valve 129 for use in purging and bleeding of conduits connecting with valve 129 by connections not shown in FIG. 34 as will be appreciated from other teachings of this invention.

Because of the simple structure of apparatus 329, manual control of the valves can be used.

Thus, the present invention provides various apparatus embodiments for accomplishing sequential multi-step processing of slide mounted or other material in processing stations using a plurality of fluid reservoirs.

Apparatus: Control Systems

Figure 25:
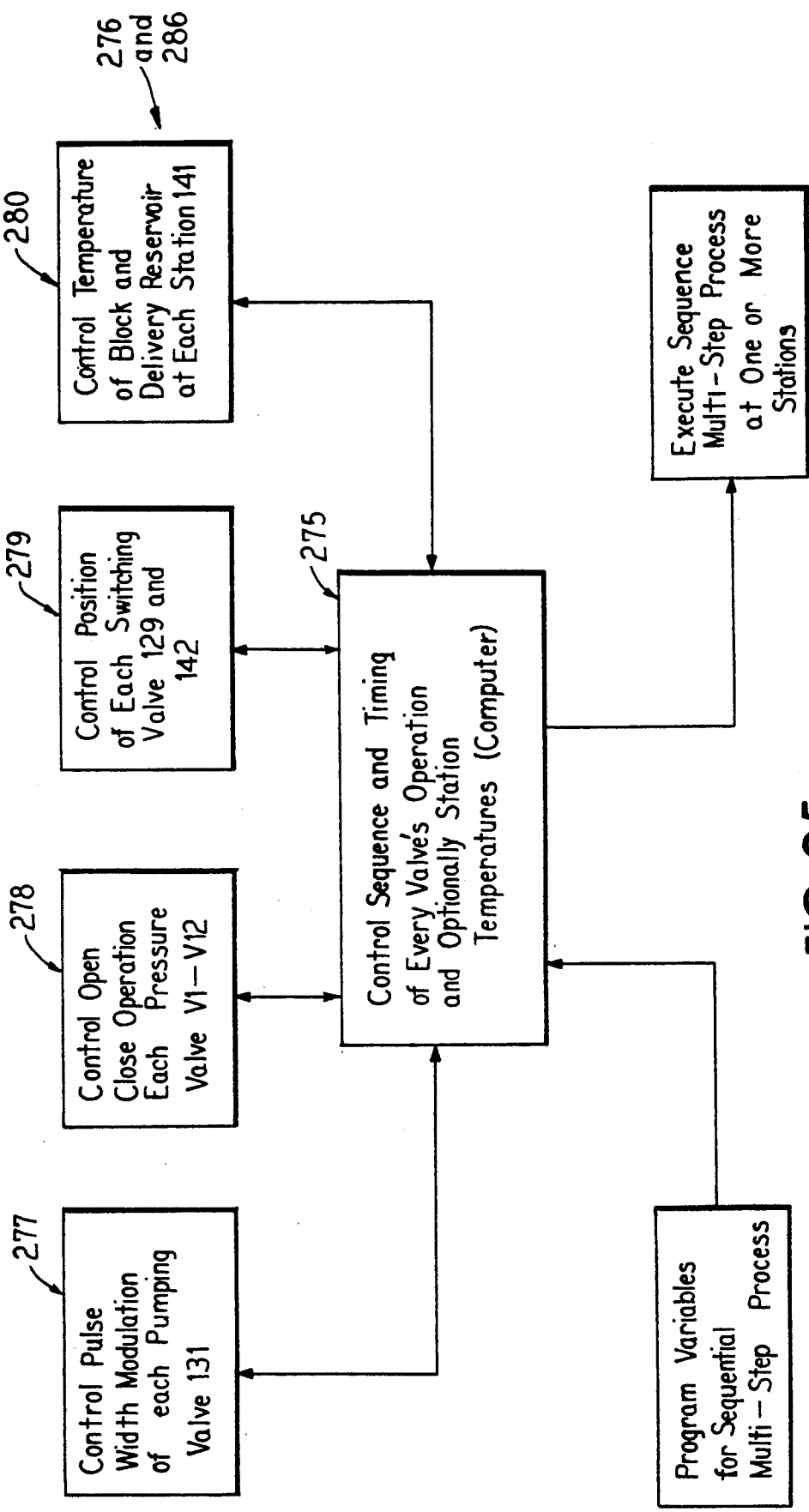
FIG. 25 is a block diagram illustrating one embodiment of a control system for sequential multi-step processing apparatus of this invention.
Figure 26:
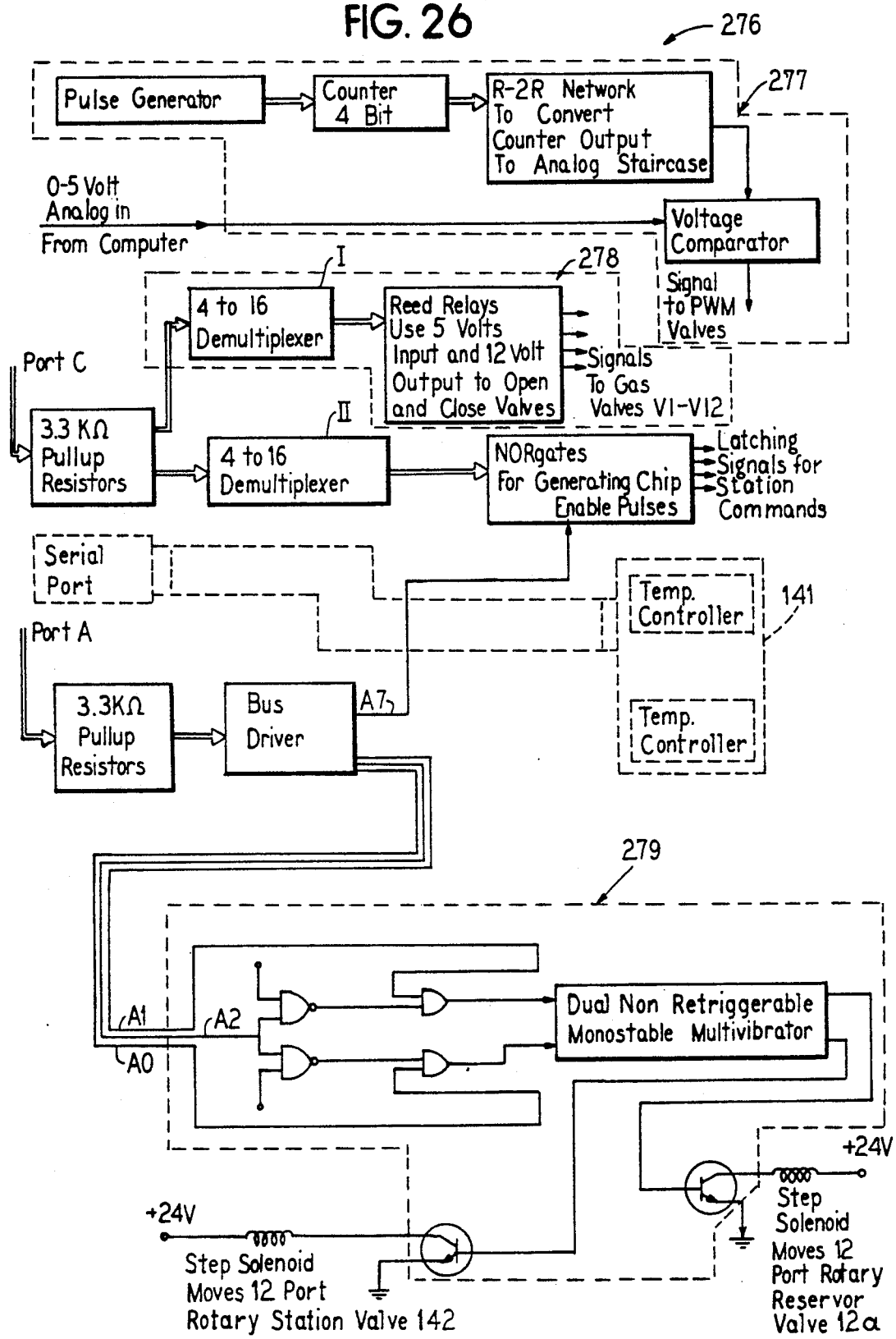
FIG. 26 is a logic diagram for electric circuits employed in a basic embodiment of a computer driven control system of this invention.
Figure 27:
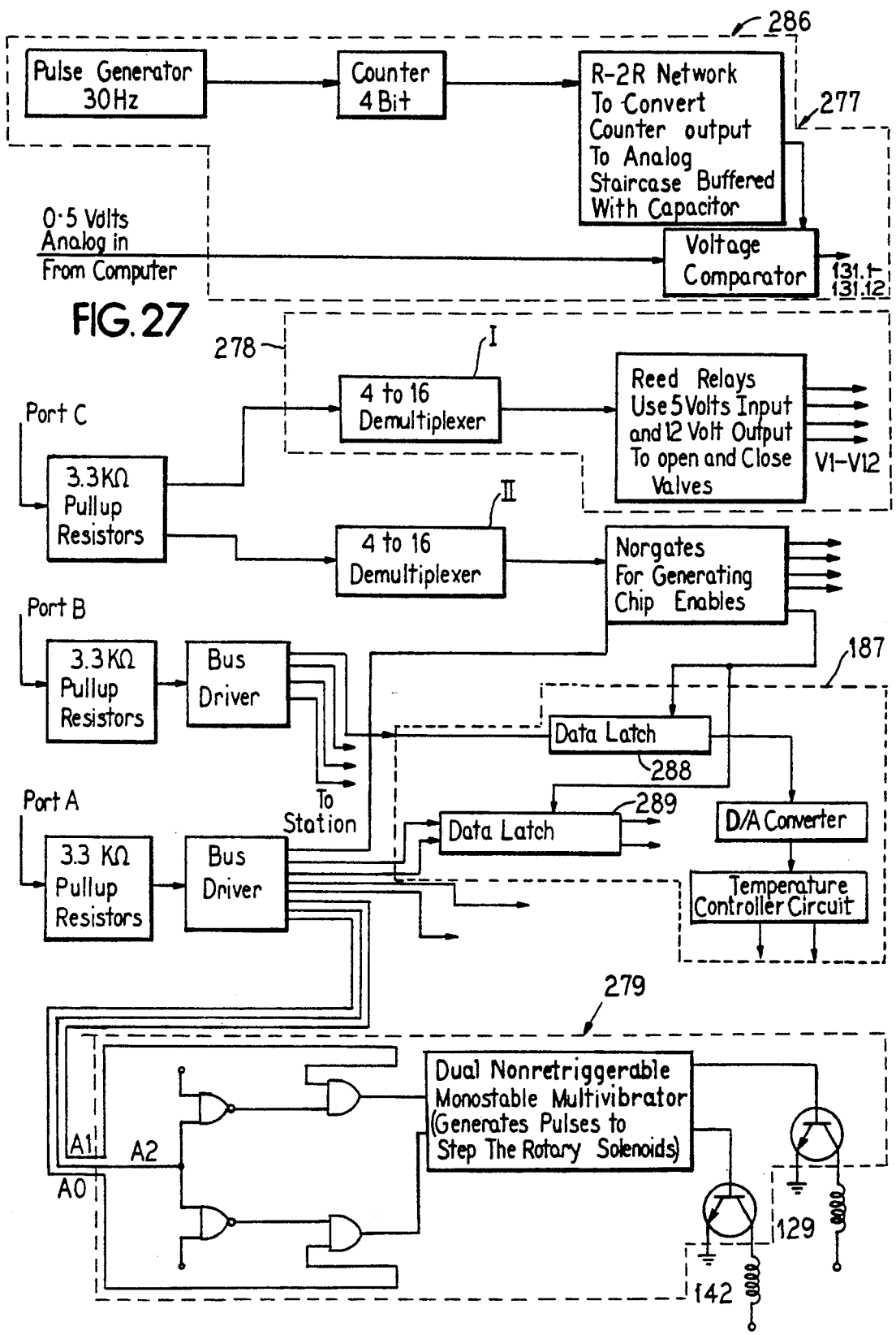
FIG. 27 is a logic diagram for electric circuits employed another embodiment of a computer driven control system of this invention.
Figure 28:
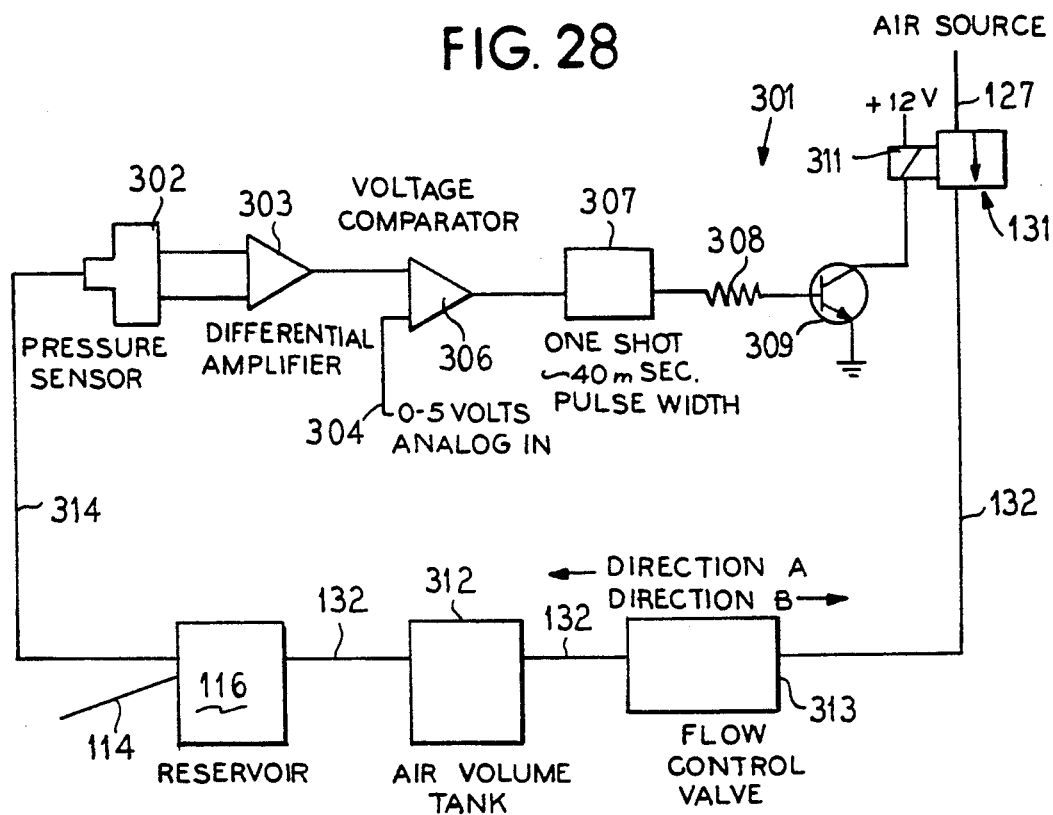
FIG. 28 is a diagram illustrating a modified combination of fluidic and electrical elements for use at each processing station module of the type used in FIGS. 20 and 21.

The valved apparatus of this invention, such as apparatus embodiment 140, can be computer controlled and driven, as illustrated in the diagrams shown in FIGS. 25, 26 and 27, with a single digital control computer, or the like, as now described.

The term "port" as used herein has conventional reference to a place of access to a computer where electrical energy may be supplied or withdrawn, or where the computer or computer generated variables may be observed and measured.

The term "gate" as used herein has reference to a device which has one output channel and one or more input channels, such that the output channel state is completely determined by the contemporaneous input channel states except during switching transients.

AND is a logic operator having the property that if P is a statement, Q is a statement, R is a statement, then the AND of P,Q,R, .... is true if all statements are true, false if any statement is false.

OR is a logic operator having the property that if P is a statement, Q is a statement, R is a statement, ..., then the OR of P, Q, R, ... is true if at least one statement is true, false if all statements are false.

NOR is a logic operator having the property that if P is a statement, Q is a statement, R is a statement, ... then the NOR of P, Q, R, ... is true if all statements are false, false if at least one statement is true.

NAND is a logic operator having the property that if P is a statement, Q is a statement, R is a statement ... then the NAND of P,Q,R, ... is true if at least one statement is false, false if all statements are true.

A gate can be an AND gate, an OR gate, a NOR gate, or a NAND gate.

The term "bus" as used herein in reference to a computer has reference to one or more conductors used for transmitting signals or power from one or more sources to one or more destinations.

A control computer 275 is conveniently provided with suitable circuitry, such as one or more so-called dadio boards. A present preference is to employ such a digital input/output board that outputs digital signals to parallel ports A and C, and also, if employed as described below in control system, an additional parallel port B. In addition, such a single dadio board can also output the desired 0 to 5 volt analog signals. Alternatively, and for another example, one can use one board with a 24 digital bit capacity which can be used 8 bits each for the ports A, B and C, and at least one other board which provide a plurality of independently controllable analog signal outputs, such as 12 such outputs or the like, which are sufficient to take care of producing the desired pulse signals for use by the respective pulse width modulated valves 131, as herein described. Such boards are available commercially from various suppliers.

Digital signals output from ports A and C are used to control the switching valves 129 and 142 and the pressurizing valves 131. Each analog output voltage signal is employed to control the individual station pumping valves 131 by pulse width modulation of that valve's solenoid current. A third port, identified as port B, is optionally but preferably included for temperature control purposes at each station.

One basic embodiment of a computer-based control system 276 which is provided by the present invention and which is suitable for controlling sequential multi-step processing apparatus of the present invention, such as exemplified by the foregoing apparatus 140, is shown in FIGS. 25 and 26. Another embodiment of a control means is shown in FIG. 27 and identified as system 286. System 276 is first generally described.

With the control system 276, the positioning and mounting of prepared slides at each individual processing station is manually carried out on each individual slide. Also, with such system 276, changes in the volume of the slide processing chamber, such as chamber 46 in a station block assembly 36, are accomplished manually, as is the use of the small channel 91 (along with actuation of its associated check valve assembly 94). However, temperature regulation of station 141 block member 37 and delivery reservoir 116 can be accomplished, if desired, before, during, and after such manually executed operations, if desired.

Control system 276 provides a relatively simple and reliable means for operating such processing apparatus to accomplish execution of a sequential multi-step processing procedure wherein fluid is passed (flowed) through each slide processing chamber in use using fluids selected from among the liquids in each supply reservoir R 1–R 11 and also the pressurizing gas in bus line 127. Further control features, and also further automation, such as to replace the above indicated manual operations, can be added, if desired, without departing from the present inventive control system 276. Also, and similarly, various optional features, such as various apparatus tests for operability, condition or readiness, inventory, verification, and the like, can be added, if desired. The usefulness and versatility of the control system 276 will be appreciated by those skilled in the art.

Control system 276 incorporate the following items, as shown in FIGS. 25 and 26:

(a) Means 277 for operating each of the variable output, pulse width modulated valves, such as valves 131.1 through 131.12 in each station modules 141.1–141.12;

(b) Means 278 for operating individual ones of the openable and closable pressurizing gas delivery valves, such as valves V 1 through V 12;

(c) Means 279 for operating each one of the two multiport conduit switching valve means, such as valves 129 and 142; and (d) Programmed means 280 for controlling the operation, sequencing, and timing of items (a), (b), and (c).

Optionally but preferably, control system 276 further incorporates:

(e) Means 281 for regulating the temperature at the block member 112 and also the delivery reservoir 116 in each one of the station modules 141.

Control system 276 utilizes preferably a single digital computer. Suitable computers include analog signal generating capacity such as is conventionally associatable with micro and mini-type computers, including those of the so-called personal computer (PC) type, for example. Suitable analog generating signal capacity can be achieved by equipping such a computer with one or more suitable circuits each in the form of a commercially available so-called "card", or circuit board, which provides the capacity in the so-equipped computer to produce on user command suitable such analog voltage signals. For example, the microcomputer used can be one of the so-called IBM compatible types which are available commercially from various manufacturers.

Above indicated item (a) or means 277 in such control systems 276 and 286 is achieved for each valve 131 by a combination of computer generated analog voltage with a sawtooth voltage as shown in FIGS. 25, 26, and 27.

Above indicated item (b) or means 278 in such control systems 276 and 286 is achieved for such pressurizing valves V 1 through V 12 by decoded multiplexed binary signals output from a port C of a control computer as shown in FIGS. 25, 26, and 27.

Above indicated item (c) or means 279 in such control systems 276 and 286 is achieved for such multiport valves 127, and 142 by processed binary signals output from a port A of such control computer as shown in FIG. 25, 26 and 27.

Above indicated item (e) or means 281 in such control systems 276 and 286 is achieved for block 112 and delivery reservoir 116 in each station module 141 by temperature controller means as shown in FIGS. 25 and 26.

Above indicated item (d) in such control systems 276 and 286 is utilized for control of such items (a), (b), (c), and (e) by a supervisory program which is designated for convenience as 280 and which is shown in FIGS. 29 through 32.

Such various items (a), (b), (c), and (e) are now described:

Each valve 131 is, as explained above, a two-position, three-way valve which in the present invention is solenoid actuated and spring biased to be in a normally closed position relative to bus line 127, and, while in such closed position, is vented to the atmosphere as respects the conduit 132. When closed, valve 131 cannot deliver pressurized gas from a source (the bus line 127) to the receiving conduit 132. When closed, the valve 131 solenoid is not actuated. Such a valve 131 is available commercially; for example, a so-called "ET-3M" valve made and sold by the Clifford Company can be used, and the solenoid of such valve is actuated by a 12 volt voltage. Each such valve 131 at each station 141 in apparatus of the present invention is operated by a control signal whose voltage varies from and including 0 to about 5 volts.

In the present invention, the valve 131 of each individual station module 141 is operated by a pulse width modulated voltage signal applied to the valve 131 solenoid. Such a voltage signal applied to such solenoid causes the flow of pressurized gas from bus line 127 through a valve 131 to be discontinuous (when the valve 131 is open to bus line 127). A rapid opening and closing of the valve 131 is achieved through corresponding actuation of the valve 131 solenoid using such applied modulated voltage pulses which have a pseudo-square wave form, such as are illustrated, for example, in plots A and B of FIG. 24.

Actually, when valve 131 is thus so opened and closed, the gas pressure that flows or ceases to flow therethrough (according to actuations of the solenoid) does not respond instantaneously. The gas pressure wave itself as produced is not a true square wave. On valve 131 opening, there is an initial gas pressure rise, and on valve 131 closing, there is a terminal delay, so that each actual gas pressure wave that occurs from a valve 131 open configuration is slightly rounded, as those skilled in the art will appreciate.

FIG. 26 illustrates one manner of producing the voltage waveform that is applied to each individual solenoid of a gas pressurized valve 131. For each station module 141, an analog (i.e. direct) voltage is computer developed, the value thereof being in accord with a user's selection of the pumping rate desired for transfer of process liquid from delivery reservoir 116 to block 112. The controlling computer voltage in the present illustrative embodiment has a value ranging from 0 to about 5 volts. This voltage is proportional (preferably linearly related) to the gas throughput or pumping rate desired for a given valve 131; for example, setting this analog voltage to be about 2.5 volts is equivalent to setting the valve 131 for operating at about one-half of its total gas throughput capacity.

Externally to the computer (or internally in a special or custom computer), a second circuit is provided which is generating a so-called sawtooth wave. In this embodiment, this second circuit is provided with a conventional pulse generator, such as a converted so-called "555 timer", or the like, available from Texas Instruments which produces a selected number of voltage pulses per unit of time. A present preference, for example, is to utilize a pulse generator producing pulses at a rate of about 30 Hz. Such resulting voltage signal is input to a conventional counter which by present preference has a 4-bit capacity. The voltage signal is conveniently smoothed out by a capacitor to produce a more defined sawtooth form without appreciable roughness (for good control achievement). The counter is capable of changing from one to the next of a sequence of distinguishable states upon each receipt of an input signal. For example, the counter can be a circuit that produces one output pulse each time it receives some predetermined number of input pulses. Alternatively, for example, the counter can be comprised of several such circuits that are connected in cascade to provide digital counting. The pulse generator and the counter need have no special structure, as those skilled in the art will appreciate.

The output from the counter is fed to a conventional conversion network, such as a so-called R-2R network, or the like. Such a conversion network preferably functions to convert the counter output to an analog sawtooth wave form comprised of staircase voltages.

A sawtooth waveform contains a ramp portion and a return to initial value portion, the two portions usually being of unequal duration.

A staircase in pulse terms is a periodic and finite sequence of steps of equal magnitude and of the same polarity.

A present preference is to produce using such a conversion network a reference sawtooth voltage waveform which varies from 0 to about 5 volts in amplitude and whose frequency is about two complete waveforms (cycles) per second; however, other arrangements can be employed. An illustration of a presently preferred form of such a sawtooth wave is shown in FIG. 24 and here each sawtooth wave is comprised of a 30 step per second staircase voltage. A condenser can be used to smooth out the waveform.

As illustrated in FIG. 24, an analog sawtooth voltage wave form $V_s$ is continuously compared in a "comparator" circuit with a steady analog voltage signal $V_I$, ranging from about 0 to about 5 volts, which is output from the control computer. The $V_I$ voltage magnitude is set to be approximately proportional to the valve 131 pumping rate setting desired. During the periods of time that $V_I$ is less than $V_s$ in magnitude, the output analog voltage of the comparator $V_C$ is negligible, or about 0 volts. During the periods of time that $V_I$ is greater than $V_s$ in magnitude, the analog output voltage $V_c$ of the comparator is an analog voltage signal of about five volts maximum having a rectangular waveform. Two exemplary such input analog voltages are illustratively shown by dotted lines superimposed on the sawtooth waveform S shown in FIG. 24. In effect, portions of the $V_s$ voltage are clipped and remaining portions thereof are rearranged to produce a voltage output wherein the pulse widths are proportional to the value of the $V_I$ voltage. Thus, a valve 131 is off (and venting) unless the $V_I$ is greater than $V_s$, but, when $V_s$ is greater than $V_I$, the output voltage up to the level where $V_s$ equals $V_I$ is pulsed. Above the value where $V_s$ equals $V_I$, a valve 131 is in an open configuration with pressurized gas passing therethrough at the line pressure existing in bus 127.

The illustrative pulse width modulated voltage wave forms A and B shown in FIG. 24 are each derived from the sawtooth waveform shown uppermost in such FIG. 24. The location along the rising portion of the sawtooth waveform where each of the respective illustrative analog voltages A and B first impact upon such sawtooth waveforms initiates the start of an output square wave pulse voltage waveform, while the location along the declining portion of the sawtooth waveform where each of the respective illustrative analog voltages A and B next or secondly impact upon such sawtooth waveform initiates the end of an output square wave pulse voltage waveform.

The output of the voltage comparator is typically not capable of delivering current levels to a valve 131 which are sufficient to directly actuate the solenoid of valve 131. For example, such output can be of the order of about 5 volts, while the solenoid of each valve 131 requires an actuating voltage of about 12 volts. Therefore, an appropriate intermediate circuit or device is interveningly positioned between each valve 131 and the voltage comparator, there being preferably one such device for each valve 131. Such circuit can be located adjacent the valve 131 in each individual station 141, for example. Such circuit is, in effect, an analog power amplifier which is (a) capable of delivering sufficient current to activate the solenoid of valve 131, (b) responsive to the voltage of the pulse width modulated waveform output from the voltage comparator, and (c) adapted to reproduce in a proportional and enlarged manner the pulse width modulated valve 131 solenoid controlling waveform. Suitable such circuits or operational analog amplifying devices are known to the prior art.

Thus, in effect, input compressed gas leaving valve 131 is pulse width modulated to produce pulses of gas pressure that are in effect applied to liquid in reservoir 116, thereby pumping such liquid into block station 112 through line (or conduit) 114 at a rate corresponding to the pulse-width modulation of the valve solenoid current. Such so-modulated current causes pulse-width modulation of the pressurizing gas (i.e., air) which, in turn, results in a pumping action causing liquid flow from reservoir 116 at a rate which is approximately proportional to the integrated (averaged) value of the pulse-width modulated gas pressure. The ratio of air pressure on-time to off-time determines the pumping rate of such liquid.

As those skilled in the art will appreciate, a sawtooth voltage for use in the practice of this invention can be generated either by generating a staircase voltage waveform digitally, and optionally smoothing it with a capacitor, or by using an integration circuit. For each of the station modules 141, a separate analog voltage generator and also a separate sawtooth voltage generator is utilized.

Thus, as can be seen from the preceding description, each of the variable output pumping valves 131 are operated and controlled by using a computer generated analog voltage signal whose strength (amplitude) is proportional to a predetermined pumping rate desired for such valve. A signal generating means for producing a reference analog sawtooth voltage signal of predetermined constant frequency is provided. A voltage comparator compares such analog voltage signal to such sawtooth voltage signal and a pulsed output voltage is produced whose pulse widths are proportional to such analog voltage signal. Circuit means functionally interconnects the voltage comparator means and the variable output valve means. Thus, the solenoid of each such variable output valve 131 is modulated and operated with such pulse width modulated voltage.

Referring to FIG. 25, and such there shown functional, logic-type diagram for control system 276, it is seen that each of the two ports A and C has its respective output signals preferably fed through pull-up resistors, as shown. Each such resistor here preferably has a value of about 3300 ohms, although larger and smaller resistance values could be used, depending upon circumstances, as those skilled in the art will appreciate. The pull-up resister is used because the computer board that sends the digital signal typically can "sync a lot more current than it can source" which means that the load resistance must be high enough to limit output current in the digital high state and thereby maintain a square (rapid rise-time) waveform, as desired.

Port C has, for example, an 8-bit digital output which is divided into two 4-bit channels. One such four bit channel is conducted, after passage through pull-up resistors, to a demultiplexer I which, as hereinabove explained, is functionally associated with the pressurizing valves identified as V 1 through V 12 in the present apparatus 140 embodiment. The demultiplexer I functions to decode the multiplexed binary digital control signals received by it, and then relays the individual valve control signals to each of the receiving valves V 1 through V 12.

The other four bit channel from port C, after passing through pull-up resistors, is conducted to a demultiplexer II.

The operation of demultiplexer I is first described:

Each of the gas valves V 1 through V 12 is, as above explained, a two position (open or closed) valve which in the present invention is solenoid actuated and preferably spring biased to be in a normally closed position. Each of the valves V 1 through V 11 when in such normally closed position relative to bus line 127 is vented to the atmosphere (as in hereinabove explained), relative to its associated respective reservoir R 1 through R 11, and valve V 12 when in such normally closed position relative to bus line 127 is not so vented relative to its associated conduit 128 (as hereinabove explained). A present preference is to employ valves V 1 through V 12 which each have an associated solenoid that is operated by a 12 volt electric current signal, but other suitable solenoid actuated valves can be employed whose solenoids are actuated by other voltage levels, if desired.

Such valves V 1 through V 12 are available commercially. For example, 12-volt solenoid on/off gas valves of the V 1 through V 11 type are available as "ET-3M" from the Clippard Company of Cincinnati, Ohio, and a suitable 12-volt solenoid on/off valves of the V 12 type is available as "ET-2M" from the same Clippard Company.

Since (a) a voltage signal is used to operate each of the valves V 1 through V 12, (b) such voltage signal is low (typically in the 5 volt range), and (c) each of the valves V 1 through V 12 is physically actuated by a current actuated solenoid that is driven, for example, by a 12-volt source, a high impedance (nearly constant voltage) source is used to control a low impedance (nearly constant current) source. Thus, a relay, such as a conventional reed relay, which itself is actuated by voltage signals in the 5 volt range, is interposed between each such solenoid and the demultiplexer. Suitable reed relays are available commercially from various manufacturers.

While, as those skilled in the art will appreciate, it is possible to operate such valves V 1 through V 12 by any convenient actuation means, it is presently greatly preferred, owing particularly to the number of discrete operational steps involved with a plurality of supply reservoirs, such as reservoirs R 1 through R 11, and also a plurality of station modules, such as modules 141.1 through 141.12, to employ computer means for operation of the valves V 1 through V 11 and V 12. When such a computer operating means is employed, it is presently preferred to employ a digital computer which generates for transfer at a suitable port or ports a binary multiplex-coded output which can be used to control the state of a number of controllable devices through a suitable demultiplexer.

A demultiplexer is a digital device which operates on binary coded input and produces a binary output signal on any one of N lines (circuits) which correspond, in the case of demultiplexer I, to each of the valves V 1-V 12 that are being controlled. In the present illustrative system, 4 binary channels from port C are input and are converted by the demultiplexer I into 16 binary individual output channels (based on powers of two). Of these 16 channels, 12 are used here, one for each valve V 1-V 12. All such outputs are relatively high (either positive or negative depending upon type of demultiplexer device being used) except for one thereof which is relatively low and which is the particular channel that corresponds to the valve being actuated or deactuated. That one low output channel is the numeral equivalent of the address to be controlled by the binary input.

Demultiplexer I is used here for controlling each of the valves V 1 through V 11 of respective reservoirs R 1 through R 11 and also valve V 12 of conduit 127. Demultiplexer II is used here for controlling each of the station modules 141.1 through 141.12.

Suitable demultiplexers are available as chip-type devices from various companies. One presently preferred demultiplexer is identified by the trade designation "74 LS 154". The demultiplexers can be regarded as being separate from the control computer.

In operation, there either is, or is not, a signal issuing from the demultiplexer I which is specifically addressed to individual ones of the valves V 1 through V 12. In a presently preferred mode of operation, the demultiplexer I utilizes 4 binary channels to define the status of the 16 output channels; however, other such combinations could be used, if desired, as those skilled in the art will appreciate. Such a system, in general, produces at least a sufficient number of different signal combinations or variations, so that each individual valve of the particular valve plurality employed (here valves V 1 through V 12) is assigned its own unique and discrete binary address signal so that the open and close positions of each such individual valve of such plurality can be separately controlled using such system.

Each individual one of the valves V 1 through V 12 is electrically connected to the demultiplexer I by wire means. Thus, when the demultiplexer I logic recognizes that a particular signal input thereinto is the unique actuation signal for closing the solenoid of one valve of such valve plurality, then the demultiplexer I releases a signal through the appropriate wire to that one valve of V 1 through V 12 which actuates the associated reed relay associated with that particular one valve. Once so engaged or actuated, such relay immediately closes the circuit which energizes the solenoid associated with the particular one valve, thereby closing that valve from its normally open position.

An electric control circuit suitable for each valve V 1 through V 12 is illustrated in FIG. 23 where the demultiplexer I component of the present computer/demultiplexer control sub-system is shown engaged with individual ones of the valves V 1 through V 12. Here, a five-volt source analog signal output by the demultiplexer causes the closing of each actuated reed relay. Only a small amount of energy is needed to actuate the reed relay which in turn causes the closing of the higher energy 12 volt solenoid circuit of the associated valve to achieve operation of a particular such valve V 1 through V 12.

When an actuation signal to a particular reed relay is terminated (through the demodulator I on binary coded command instructions from the computer), the reed relay promptly opens, the current is lost to the solenoid of the actuated one valve of V 1 through V 12, and that valve opens so that pressurized gas can no longer be input therethrough. De-energization of the valve solenoid approximately corresponds to termination of gas flow through such valve.

Thus, as can be seen from the preceding description, individual ones of such openable and closable valve means V 1 through V 12 are operated and controlled by using computer generated multiplexed digital signals which incorporate an address code for each of such valves and which can incorporate an order code directing a particular one of such valves to open or close. Demultiplexer means for receiving decoding, and producing an output signal for each such valve is provided. Circuit means functionally interconnects such demultiplexer means with each one of such valves for making each such valve responsive to correctly corresponding ones of such output signals.

In the basic control system 276, the demultiplexer II is an optional, but preferred component. Decoded multiplexed binary digital control signals output from demultiplexer II are used as input signals for each respective one of a series of individual NOR gates. Each such NOR gates can be of this conventional two input, one output type. The second input to each respective such NOR gate receives signals from another source. For example, in the present illustrative system 276 embodiment, a signal from channel 7 of port A is input into each such NOR gate. Channel A 7 can, for example, carry information signals showing that charging of a given reservoir 116 in a station 141 through valves 129 and 142 is not occurring (or has terminated). Also, for example, signals fed to demultiplexer II from port C can constitute command signals for individual stations 141 or individual regulatable components thereof.

Such command signals can be used to initiate a function, or terminate a function in a multi-step operational sequence. Operation of the valves 131.1 through 131.12 is controlled by pulse width modulation independently of such command signals. Operation of the valves V 1 through V 12, and also, operation of valves 129 and 142, is independent of such command signals. Such command signals are set up in accord with a predetermined set of definitions or variables created for a given multi-step processing sequence. Examples of possible such events include:

(1) The station 141 delivery reservoir 116 must contain a predetermined quantity of a liquid which is to be pumped from reservoir 116 through the station block 112 before pumping by associated valve 131 begins.

(2) The delivery reservoir 116 must be emptied of a preceding processing liquid before a given pumping by associated valve 131 ceases.

(3) If temperature is a critical process variable, then the set temperature of either the station block 112 or the delivery reservoir 116, or both, must be reached before a given pumping by associated valve 131 begins.

Apart from process parameters, various equipment conditions or states can be selected as limitations upon the start of processing or the continuation of processing at each station 141. Examples of such events or situations include:

(1) Have the conduits C 1 through C 11 from each respective reservoir R 1 through R 11 to valve 129 been bled?

(2) Is the chamber 46 of block 112 closed (i.e., is the slide being processed in place as shown by a signal switch)?

For present illustration purposes, command signals regarding such events, conditions, or states are generated and input to demultiplexer II. After decoding, such signals are received as inputs in individual NOR gates along with inputs received from channel A 7.

In normal individual NOR gate operation, the internal switches thereof are normally closed. When such switches are both opened by appropriate input signals at each input line, there is an output. This output constitutes a chip enable pulse which can be used as a latching signal for operating a latch device. Output signals from the latch device can be used for effecting station operational commands.

Suitable data latch devices are commercially available in chip form from various commercial sources. It is presently convenient and preferred to employ a data latch device of the type which has an input bus, an output bus, and at least one enable input line. For present illustrative purposes, only one enable line per latch is utilized. If no latching signal is input through the enable line, then whatever is stored in the latch is put out on the output bus. For example, when the input enable signal pulse is low, then the latch ignores the signals on the input bus, and it keeps on outputting whatever is already being output on the output bus. If, on the other hand, a latching signal is input through the enable line, then the latch takes whatever is on the input bus, and in effect remembers such, and then immediately outputs such on the output bus. For example, when the input enable signal pulse is high, then the latch takes the input bus signals and places same on the output bus line. Here, each data latch has a digital output that serves to accomplish a command function.

In control system 276, the valve 131 of a given station 141 is actuated into its pumping operational mode after transfer of liquid from a given one of reservoirs R 1 through R 11 into the delivery reservoir 116 of such station has been completed and after the multiport valves 129 and 141 have been switched away from the particular delivery conduit 131 of such station 141, as in the operating step sequence described hereinabove, for example, in relation to apparatus 140 (when temperature regulation is not involved).

Upon the completion of a liquid transfer operation from one reservoir R 1 through R 11 to one delivery reservoir 116, the binary command signals output by port C to demultiplexer I for the activated associated one valve of V 1 through V 12 cease, causing deactivation of the reed relay and solenoid that are associated with such one valve.

Upon completion of a reservoir 116 pump down by valve 131, the computer software (conveniently based on elapsed time) instructs the valve 131 to stop operating. Once valve 131 operation is initiated, a latch device in the computer maintains the 0 to 5 volt analog output voltage at a preset value, and the pulse generator operates continuously, thus both signals continuously interact in the voltage comparator and produce an output signal that maintains a valve 131 in an "on" operating mode. When the analog voltage output stops, valve 131 operation stops.

To make sure that a valve 131 does not start operating at about a zero analog voltage output, it is presently preferred to adjust the system so that the operable range extends from a value slightly below zero volts; for example, from about 0.005 volts to about 4.995 volts, as those skilled in the art will appreciate.

Each of the switching valves 129 and 142 is provided with a solenoid which, when actuated, steps (advances) the rotary valve core member thereof from one fluid flow complete valve pathway to a next succeeding such complete valve pathway. Each such pathway extends in the valve body and core from a single core port and pathway to and through one of the plurality of valve internal pathways to terminate at a particular valve body port, as those skilled in the art will appreciate.

To accomplish the step-wise, rotational, successive advance of the rotary valve core to each predetermined pathway position using, incremental step-type movements of the associated solenoid, the following arrangement is employed:

Port A of the control computer, which preferably has an 8-bit digital output and 8 output channels, outputs on three channels thereof digital signals which, after passing through the pullup resistors, are used for solenoid activation and switching of valves 129 and 142 solenoid advancing. In FIG. 26, these channels are identified as channels (or circuits) A 0, A 1, and A 2.

A reference or "home" location for each one of the valves 129 and 142 is provided since otherwise there is no way for the control system 276 to identify what position the rotor of such a switching valve is in. Thus: Each of the switching valves 129 and 142 has a rotary switch associated with the solenoid and the solenoid is provided with a pair of opposed, co-axially located stub shafts that extend therefrom. The forward one of such shafts is used to turn the valve rotor and the rearward one of such shafts is used to turn the switch. One electric line is connected to the center of the switch and another such line is connected to one of the 12 switch position contacts so that when the switch is in such #1 position a short occurs between these lines. Thus, a "home" position on each such valve is identified which is readily detectable and usable as a detection signal for feeding to pulse circuitry.

Before such a switching valve's solenoid is stepped in response to digital command pulses issued by the control computer through port A, but after the termination of a previous switching valve setting, or at start up, as the case may be, the valve receives signals through circuit A 2 which are adapted to cause the solenoid thereof to step 13 times. Thus, the rotary core of such valve, regardless of its initial position, is stepped around until it reaches the home position. When the valve is in the home position, it generates an output signal (as above explained) which is fed to one input port of a conventional two input port, one output NAND gate. The second input port of the NAND gate is fed an input signal from one output circuit of the port A (here, illustratively, channel A 2) which identifies the switching valve home position. A logic level one is characteristically output from the NAND gate for all input states except for the condition where both input signals are at logic level one which only occurs when the associated switching valve is in its home or #1 position. In effect, the feedback signal from the valve in its home position switches the NAND gate to a closed position where further pulses on the A 2 line have no result since they do not pass the NAND gate.

Thus, for example, when pulses are sent along channel A 1 for switching valve 129, that valve's solenoid steps around until it is in the "home" position, and then it stops stepping. When, for example, the A 1 line is alternatively pulsed high and then low, and the A 2 line is high, then, when no signal is coming back from the valve 129, that valve's solenoid is continuously stepped. However, when the A-2 line is high, and the valve 129 reaches the "home" position, then the peripheral circuitry ignores any further pulse commands to pulse.

Next, command digital signals are input, for example, into the switching valve 129 from line A 1 which cause the valve solenoid to step, starting in its home position and thereby move the valve rotor to its desired position for a succeeding fluid transfer. Thus, the output line from the NAND gate is delivered as an input line into a succeeding conventional AND gate which is of the two input, single output type. The second input line of such AND gate receives line A 1. In effect, only when both inputs are at logic level 1 is an output signal possible from such AND gate. Thus, for example, high signals from the NAND gate and from line A 1 can result in signal passage through the AND gate so that the desired pulse switching command signals can proceed forward to valve 129, as desired. A separate such combination of NAND gate and AND gate is provided for each switching valve, as shown in FIG. 26.

Since the pulse signals forwarded as an output from the AND gate (whether originating from the A 1 line or the A 2 line) are not suitable for operating the 24 volt solenoid associated with each switching valve 129 and 142, the following arrangement is employed in the illustrative embodiment: The output signals from the AND gate are input into a non-retriggerable monostable multivibrator. Although multivibrators are analog rather than digital devices, they are readily capable of working as pulse generators. A monostable multivibrator has one stable state and one quasi-stable state. Starting in its stable state, a triggering signal transforms it into its quasi-stable state. After a certain period of time, the circuit returns to its stable state. Thus, the output is in the form of a pulse width which is equal to the circuit delay time. Each pulse width here produced is suitable for accomplishing a one step advance of the valve solenoid. A further triggering signal is necessary to generate another pulse, and so on. Because of this, such device is known as a non-retriggerable, or one-shot, multivibrator. The total number of pulses produced in any one switching operation is equal to the number of pulses needed to switch the valve to any one of the 11 positions desired beyond the "home" position (no pulses are produced if the "home" position is the desired position).

Because the pulse signals output from such multivibrator are only about 5 volts, they are not large enough to operate the 24 volt valve solenoids. Accordingly, in the present illustrative embodiment, a MOSFET (metal oxide semiconductor field effect transistor) is interposed between the 5 volt output of such multivibrator and the 24 volt solenoid current source. The MOSFET here functions as a solid state relay such that the solenoid current through the MOSFET is controlled by the voltage applied to its base.

Each switching valve is provided with such a combination of multivibrator and MOSFET. Both such devices are available commercially in suitable forms. For convenience, a present preference is to employ a single chip which incorporates dual non-retriggerable, monostable multivibrators, such as one which is available commercially under the trade designation "74LS221" from various suppliers. Various suitable MOSFETS are available commercially.

Those skilled in the art will appreciate that other arrangements are suitable. For example, selection of a 12 position rotary valve with a 24 volt solenoid is relatively arbitrary since any rotary valve with suitable operating and performance characteristics could be used here if, for example, the valve mechanical torque is sufficient. The voltage requirement is determined by the particular mechanical design selected.

Thus, as can be seen from the preceding description, the switching valves 129 and 142 are each operated (switched) by employing a computer to generate a digital signal which includes information identifying a particular position desired. Gate means is employed to receive such digital signals and pass same based on a prechosen switch home position. A non-retriggerable monostable multivibrator receives such so passed digital signals and converts same into output voltage pulses of suitable duration for valve solenoid stepping. Appropriate circuit means functionally interconnects such multivibrator output with each switching valve's solenoid.

Preferably, a control system of the present invention incorporates means for maintaining the temperature of each of the block member 112 and the delivery reservoir 116 of each individual station module 141 at respective approximately predetermined values or set points.

A convenient and presently preferred temperature regulation arrangement is to circulate the coolant liquid as above explained through the passageways provided in each of the block members 112 and the delivery reservoirs 116 of the various station modules 141.1 through 141.12 with the input temperature of the coolant liquid being at ambient values. Concurrently, the respective electric heating elements in each of the various block members 112 and delivery reservoirs 116 individual heat these respective components to a desired set point. The circulating coolant permits an elevated temperature to be rapidly reduced or increased for purposes of a succeeding process sequence, or the like.

Each individual one of the blocks 112 and the delivery reservoirs 116 can be provided with a temperature sensor and a conventional temperature controller, such as a temperature controller of the types available commercially from the Omega company under the trade designation "CN2012". The temperature controller includes a control loop which regulates the amount of current fed to the electrical heating element. A present preference is to use an alternating current power source having a voltage of about 110 volts alternating current for the energizing of series connected individual heating elements. The amount of current so fed corresponds to the amount needed for achieving the set temperature.

The temperature set point of each temperature controller is itself set (adjusted) in accordance with the present invention by digital control signals generated by the controlling computer and conveyed to each temperature controller. To accomplish this result using the control system 276 it is presently preferred to employ at least one serial port on the same controlling computer that is used for accomplishing control and switching of the apparatus valves, as above explained.

Thus, in system 276 of FIG. 26, such a serial port and pair of temperature controllers for one station 141 is shown in phantom (dotted) lines for illustration. The various temperature controllers of all stations 141 of apparatus 149 are effectively connected together in parallel with a common bus line that connects with a single serial port. Dip switches in the individual temperature controllers, which are each preliminarily assigned an appropriate identification number, recognize individual temperature controller signals so that set point regulation is accomplished.

Another embodiment of a computer-based control system 286 is shown in FIG. 27. Control system 286 incorporates various aspects and features that are associated with the control system 276, so corresponding components are similarly identified for convenience in control system 286.

In addition to the parallel 8 bit ports C and A, the system 286 utilizes an 8 bit parallel port B whose output digital signals are coded for temperature control. Ports B, C, and A can be of the RS232 type. Signals from port B are fed serially through 3300 ohm pullup resistors and then through a bus driver before being delivered to individual control boards 187 incorporated into each individual station 141. Only a single board 187 is shown for simplicity in FIG. 27.

Each control board 187 in the embodiment shown in FIG. 27 incorporates two latches identified as 288 and 289 whose operation is as hereinabove indicated and which can be similar in constructions to the latch devices incorporated into control system 276. Such latches can be of the 74LS373 type, for example.

Output from latch 288 is fed to a digital to analog converter, and the output from such converter is fed to a temperature control circuit which generates an output signal for temperature set point regulation of a temperature control device associated with the station 141 block member 112 or delivery reservoir 166. Another such combination (not shown in FIG. 27) of latch, digital to analog converter, and temperature control circuit can be employed in the control board 187 for the other station temperature control device. Conventional serial 1200 baud data or the like can be sent out of port B to the station 141 temperature controllers and each control board 187 decodes the data which it recognizes as being directed to it, and adjusts the set points responsively. The use of a station chip to convert digital signals relating to temperature control issuing from a parallel port B into analog output signals usable by a temperature controller can effect constructional cost savings over the use of a serial port to input digital signals directly into individual temperature controllers each adapted to directly utilize such inputs for set point regulation (as above described herein).

Binary circuits associated with port A that are not used for control of rotary switching valves 127 and 142 can be employed for various additional control purposes, such as, for example:

(a) commanding a station block 37 to open or to close its associated slide holding apparatus;

(b) commanding a block 37 to change the volume of its chamber 46 from one size to a second smaller size, and the reverse, through operation of its associated slide holding apparatus; and (c) commanding the execution of a bleeding of all conduits C 1 through C 11 while maintaining all the stations inoperative and also the valve 142 in a specific configuration.

Such control commands are readily effected with the control system 286 where each individual station 141 is provided with its own individual circuit board 287. The latch circuit 289 in board 287 is employed in executing commands such as above exemplified. The latch circuits for each station can effectively be in a sort of parallel relationship to each other. A bus can be used to interconnect all stations with the relevant output circuits of each of port B and port A, for example.

For illustration, the recycle reservoirs 237 can be operated by using one latch circuit to control the gas valve 272 and another latch circuit to control the valve 244.

Under certain operating conditions, the process liquids input into a station block 112 with the pulse width modulated valve 131 at each station operating as above described in apparatus 111 or 140, for example, may be observed to fluctuate in flow rate. One possible cause is theorized (and there is no intent herein to be bound by theory) to be gas pressure expansion and compression effects exerted upon the conduit flexibility characteristics inherently associated with conduits comprised of thermoplastic polymers. Locating the station needle valve 139 in close proximity to station 112 in conduit 114 helps to alleviate such fluctuations.

However, a presently preferred system for alleviating such fluctuations is to equip each station 141 with a control loop 301 such as shown in FIG. 30. Control loop 301 uses a solid state silicon pressure sensor 302 to sense the instantaneous (or on line) pressurizing gas pressure that is effectively being applied to the delivery reservoir 116. Suitable silicon pressure sensors are available commercially. Such a sensor has an analog signal output and operates analogously to a Wheatstone bridge.

The electrical/electronic operation of loop 301 is as follows: The electric signal output from the sensor 302 is linearly related to the sensed pressure and directly correlates to pressure. The millivolt output from sensor 302 is amplified on the order of about 100 times in the differential solid state amplifier 303 to produce a voltage level signal which can be compared to the analog signal. The analog signal output from the amplifier 303 is input to a voltage comparator 306 which also concurrently receives a controlled computer generated 0 to 5 volt analog signal 304 that is output by the control computer (not shown in FIG. 30) for the particular valve 131 of a given station 141 (not shown completely in FIG. 30). This analog signal 304 is proportional to the pumping rate desired for the valve 131. The output analog signal from the voltage comparator 306 is then input into a one shot multivibrator 307 which can be a so called 555 timer appropriately connected. The output from such multivibrator 307 is in the form of a pulse whose width is suitable for actuating the solenoid 311 of the valve 131. Such pulse width is equal to the circuit delay time. A further triggering signal is necessary to generate another pulse from the multivibrator 307, and so on successively. The frequency of the output pulses from the multivibrator 307 is determined by the interaction between the 0-5 volt analog voltage and the amplified pressure sensor signal that are fed into the voltage comparator 306. This output pulse frequency in effect chosen by the circuit to be at a value which is needed to produce a pumping rate for valve 131 that is necessary to keep a steady pressure at the pressure sensor. The pressure desired is set by the level of the 0 to 5 volt analog signal which results in a direct pressure conversion.

The pulsed output from the multivibrator 307 is fed through an appropriate biasing resistor 308 to a transistor 309 which interfaces between the multivibrator 307 and the solenoid 311 of valve 131. Specifically, the output from the multivibrator 307 is fed to the base of transistor 309 through an appropriate resistor 308 (to avoid grounding the output from the multivibrator 307), and the collector of transistor 309 is attached to the solenoid 311. The emitter of transistor 309 is grounded. To one end of solenoid 311, a solenoid activating voltage, such as 12 volts, is applied while the other end thereof is connected to the collector. Since there is thus, in effect, zero volts applied to the transistor base, there is no conduction therebetween and the solenoid effectively floats at 12 volts. When the transistor base receives a pulse from the multivibrator 307, the collector and the emitter and the Collector effectively come together and the solenoid 311 is actuated resultingly.

Thus, for example, an output pulse of about 5 volts from the multivibrator 307 can be used to drive a 12 volt solenoid 311 and accomplish pulse width modulation of such solenoid to achieve the desired variably controllable throughput of compressed gas through valve 131. The valve 131 is, in effect, turned on and off at a rate sufficient to maintain a specified pressure in reservoir 116 through association with a selected one of the 0 to 5 volt analog controlled input signals (hereinabove described). A present preference is to employ a compressed gas pressure in the range of about 4 to about 10 psi with a range of about 5 to about 7.5 psi being more preferred. The pressure sensor 302 can have a response characteristic in the range of 0 to about 15 psi.

The mechanical arrangements in the loop 301 are as follows: Between the reservoir 116 and valve 131 in pressurized delivery gas conduit 132, a gas volume tank 312 and a flow control valve 313 are connected with the tank 312 being adjacent the reservoir 116 and the valve 313 being adjacent the tank 312. The pressure sensor 302 preferably monitors pressure reservoir 116, but a present preference is to monitor the gas pressure either in the conduit 114 or in the reservoir 116 with the pressure sensor 302. In the presently preferred operational mode, the sensor 302 is functionally associated with the reservoir 116 through an interconnecting sensory conduit 314.

The gas tank 312 exerts some smoothing effect upon gas pressure variations in conduit 132 and acts as a gas volume storage chamber between valve 131 and delivery reservoir 116. Characteristically, the combination of the valve 313 and the tank 312 causes discharge of compressed gas from tank 312 more quickly than it charges.

Tanks suitable for this purpose are available commercially from various sources. While there need not be a relationship between the volume of the reservoir 116 and the volume of the tank 312, a present preference to employ a volume ratio of reservoir 116 to tank 312 that is in the range of about 5:1 to about 20:1, although larger and smaller such ratios can be employed, if desired. Conveniently, the tank 312 can have a volume in the range of about 10 to about 50 cubic centimeters, although larger and smaller volumes can be used.

The flow control valve 312 offers little resistance to gas flow in direction A but conduit 132 offers adjustably variable resistance to gas flow in the opposed direction B (as shown in FIG. 30). Since the valve 131 vents to the atmosphere when it is not on or operating, and since the gas volume tank 312 empties more rapidly than it fills, the flow control valve 313 acts to smooth out the pressure variations in pressurized gas flowing into reservoir 116 by choking the vent-to-atmosphere portion of the operating cycle.

Particularly when a control loop 301 is utilized, it is now much preferred to remove valve 139 from its location in conduit 114 and to insert this valve 139 in conduit 134 adjacent station block 112 (the location being illustrated by the phantom box 141? in apparatus 111 in FIG. 20). Such alternative location can improve pressure control. Thus, when a charge of process liquid, such as 1 milliliter, for example, in delivery reservoir 116 is being pumped by valve 131 through conduit 114 into and through block 112, it is sometimes observed that near the end of such a pump down, when the process liquid "heel" in the delivery reservoir 116 is relatively small, the compressed gas pressure applied thereagainst from the interior of such reservoir 116 can induce a "slugging" effect by which the "heel" residue is charged at a rapid and irregular rate. Characteristically, compressed gas flow occurs relatively rapidly through needle valve 137 and liquid flow through valve 137 occurs relatively slowly. The result is that the desired full extent of surface treatment or contacting between the material being processed in a chamber 46 of block 37 (such as the coating on a slide surface) at station 112 and the process liquid moved thereover is not achieved. For example, in the case of a wash cycle or step in a multi-step process sequence, the desired full wash is not achieved. By relocating valve 139 as described, a more rapid initial fill of chamber 46 of block 112 is achieved, as when the chamber 46 is initially gas filled, which is believed to be desirable. Also, the above-indicated terminal slugging effect at the end portion of a delivery reservoir 116 pump down is avoided, which is desirable.

Particularly when the control loop 301 is utilized, the needle valves 137 through 137.12 are removed from their respective associated conduits 133.1 through 133.12.

To implement this present control system, fundamental type software codes are used for computer generation of the outputs required at each of the ports A, B and C, the analog voltage levels, and, if employed, the social port(s). Such codes are board specific and determined by the circuitry therein. Thus, the components commercially purchased are associated with individual codes, so generalizations are not possible. Those skilled in the art who are familiar with the use and operation of such boards, codes, and computer interfacing understand the use and operation of such codes.

Computer Control: Supervisory Program

To, in effect, organize and control the operation of apparatus such as 111, 140, or 211 using the above described means for operating each of the individual station variable output valve means 131, the individual ones of the openable and closable pressurizing valve means V 1–V 12 and the multi-port switching valve means, 127 and 142 a supervisory computer control program is employed.

An exemplary supervisory computer control program 280 for use in manipulating the fundamental codes and in achieving programmed operation of apparatus of this invention is shown in logic diagrammatic form in FIGS. 26, 27, 28 and 29.

Referring to FIGS. 28–32, there is seen one embodiment of an exemplary supervisory computer program 280 that is suitable for operating the apparatus of this invention such as apparatus 140 using a control system 276 or 286. At start up, the program is initialized, preferably automatically, to ensure that all indicators and constants are set to prescribed conditions and values before the program routine is obeyed. Then, lines are serially read from a command file and executed. System parameters are entered at the first decision point 291 (see FIG. 29) by the operator. Such parameters can include temperatures of the station block 112 and the delivery reservoir 116 at each station 141 during each process step, the quantity of each process liquid to be put through each station block 112 during a given step, the pumping (flow) rate of each process liquid through each station block, time delays for such purposes as execution of manual input and manual removal of liquid probe composition at each station for temperature stepping, or the like, such as when the systems go into a pause mode, and the like.

Because of the potentially large number of individual operational parameters which would have to be selected and entered by an operator to set up a supervisory control program for operator running, it is now preferred, as in the program 280, to have some step sequences take place automatically, thereby to simplify the demands upon the operator. For example, when the total amount of a process liquid to be used at a given station during one process step exceeds capacity of the delivery reservoir 116, the supervisory program accepts the operator selected total amount and then proceeds, during that one process step to shut down the delivery reservoir 116 pump down by valve 131 for that cell at a predetermined point and to initiate a delivery reservoir 116 refill after which the pump down restarts by activation of the valve 131. Such an automatic cycling is repeated until the operator specified amount of a given process liquid has been put through the particular cell blocks 112 from the particular delivery reservoir 116.

For another example, for reasons of accurate quantity transfer of a given process liquid from a given supply reservoir R 1 through R 11 to a given station 141 delivery reservoir 116, it is much preferred to bleed all the conduits C 1 through C 11 before a given sequential multi-step process is commenced, and/or after any major shut down (wherein such a conduit could drain).

Thus, after system parameters are duly entered at the first decision point 191, the computer processes to the next decision point 292. Here observations, comments, and the like (not commands) are displayed for operator review and decision. Such remarks can be ignored, or responded to, by the operator.

Figure 29:
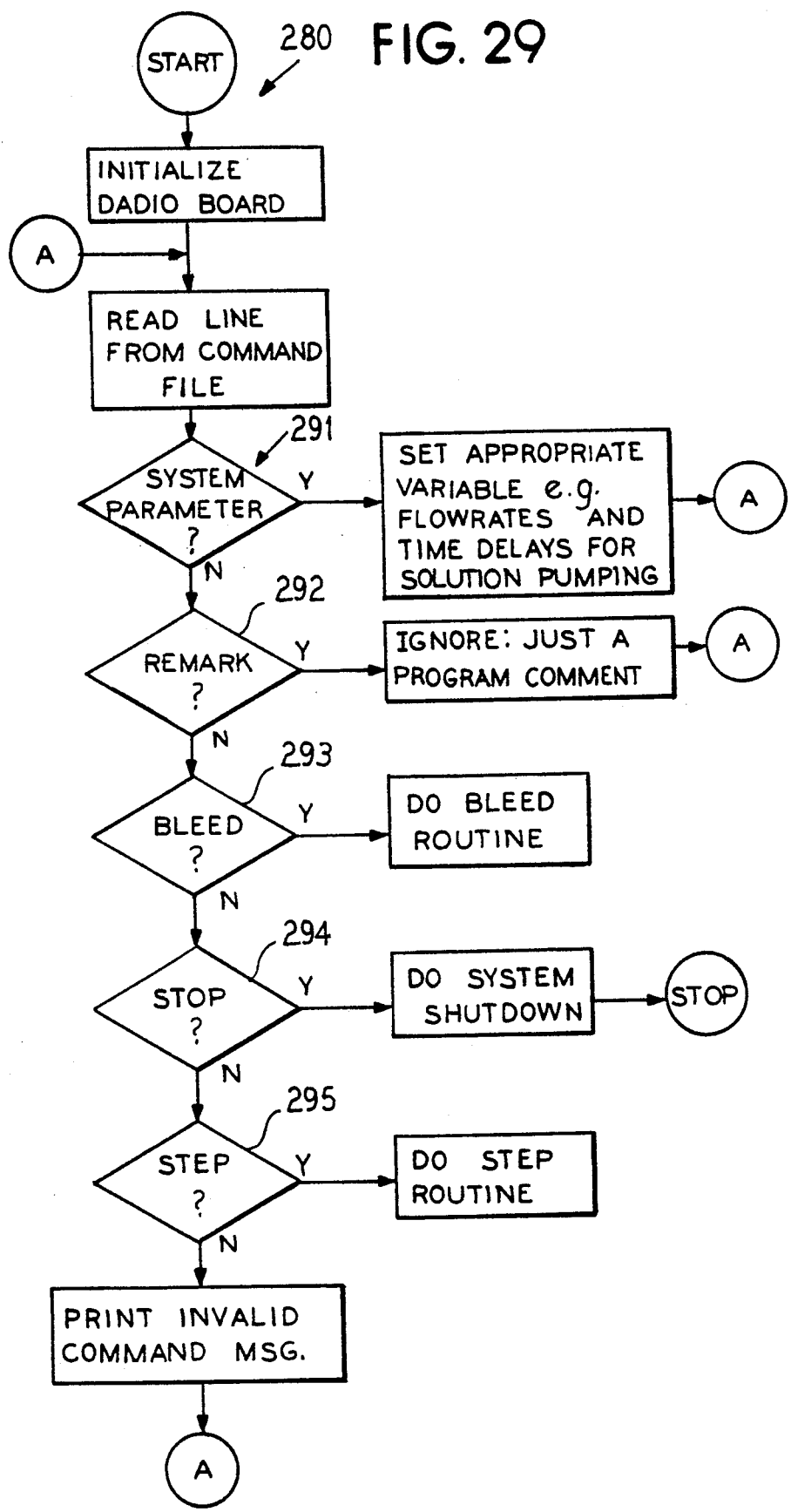
FIG. 29 is a flow diagram of one embodiment of a supervisory-type computer program suitable for operating apparatus such as shown in FIG. 21, using a control system such as shown in FIGS. 25-27 wherein, in a sequential multi-step process, the step sequence and the individual step conditions are computer controlled.
Figure 31:
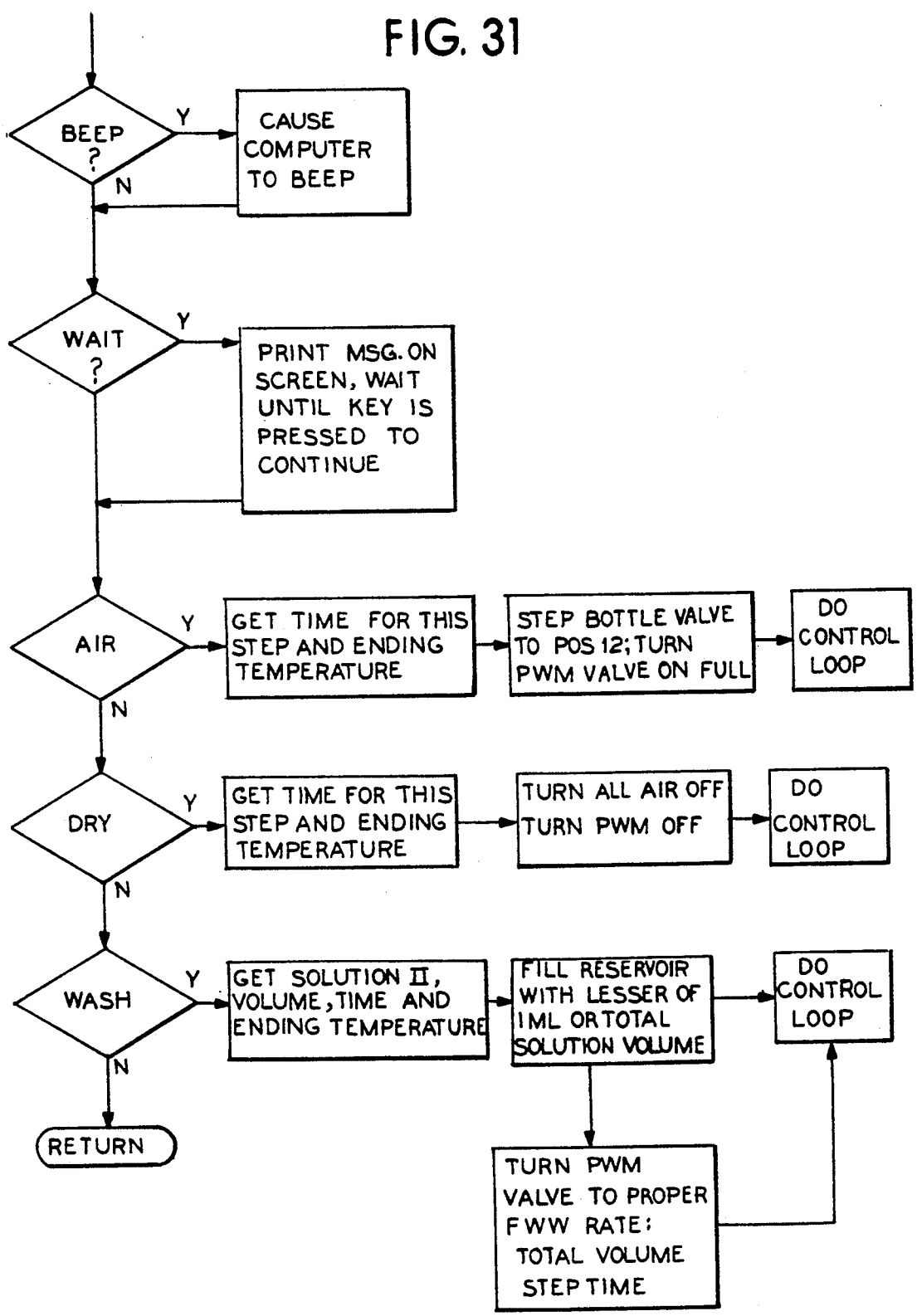
FIG. 31 is a flow diagram of one embodiment of a subcommand program employable in the program of FIG. 29 for operating apparatus such as shown in FIGS. 20-22.

Next, the decision point 293 is reached. If all is in readiness, the operator initiates at point 293 a bleed routine such as shown in FIG. 30 in the course of which that routine is repeated for each conduit C 1 through C 11. In FIG. 29, the letter "i" is employed as an index number and counter, and "i" can be any value of 1 through 12. Valve 142 is not used in the bleeds. The waste valve 124 is opened and valve 129 is cycled. If no valve 144 is employed, then valve 129 is turned to a master delivery position as employed for a sample loop. When compressed gas enters through valves V 1 through V 12, it pumps through the sample loop and into waste. No liquid should pass to a station reservoir 116 until the bleed has been completed, in the preferred utilization of the apparatus of this invention, to avoid aberrations in liquid transfer caused by gas pockets in the conduits. The bleed routine runs in a loop until completed and the bleed valve is closed after which the program leads back to position A (the program start point) at the top of the read command section. The program runs (advances) after it initializes the dadio board. The program is set to read a line, then execute the command in that line. Intervening storage is not used.

After the bleed routine, the option of stopping or proceeding is presented in a next decision point 294. If all is in readiness, then the sequence of a multi-step routine is commenced at subsequent decision point 295 as illustrated by the command "do step routine".

If a syntax error occurs, the program goes off track and begins at the next line, as illustrated.

Figure 32:
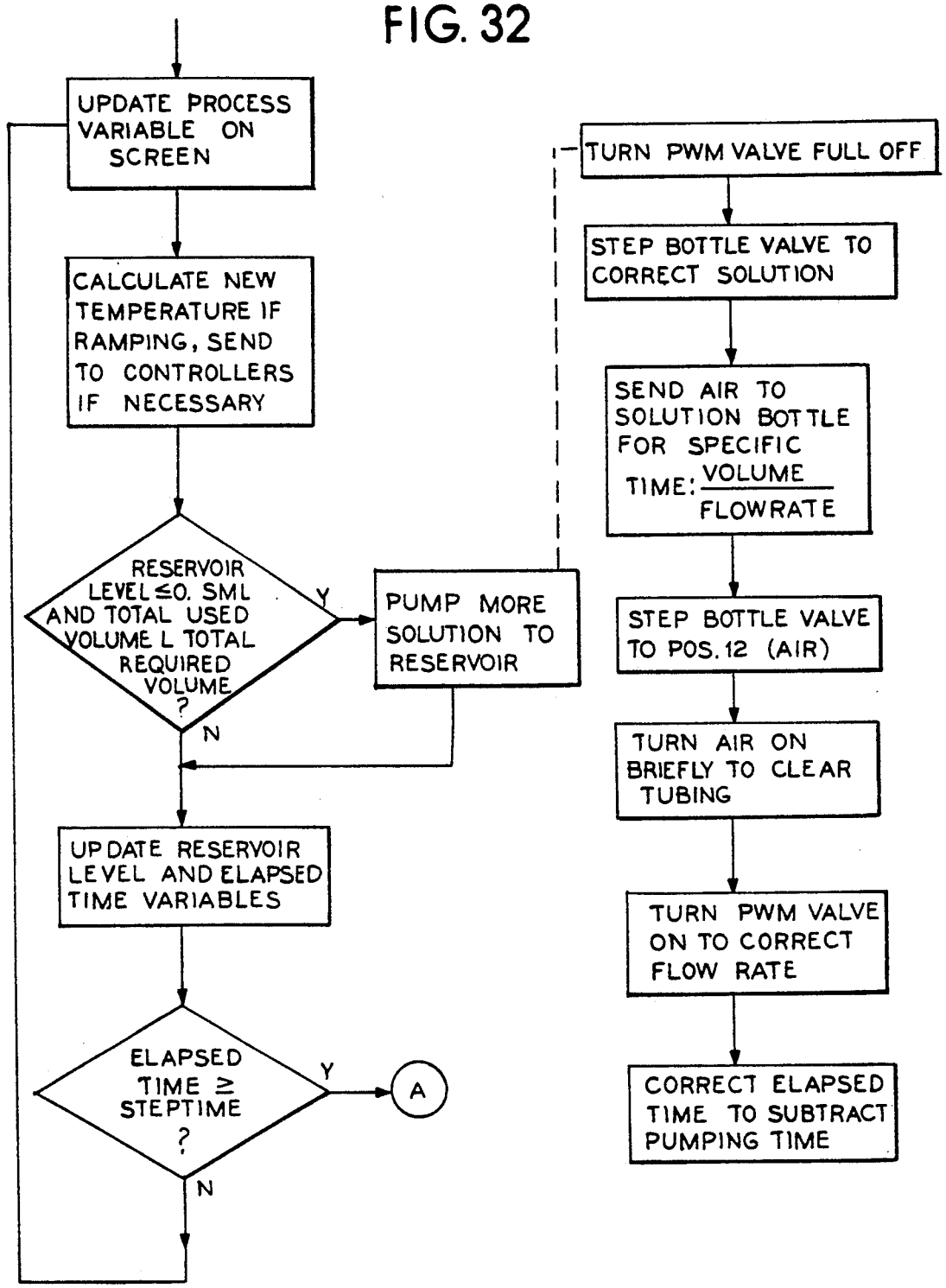
FIG. 32 provides a flow chart of a control loop for operating apparatus such as shown in FIGS. 20-22.

In FIG. 32, a step sequence is shown which is followed for each cell. The sequence updates the process. The sequence is executed for each cell at a time before going on to the next cell. Here, illustratively and representatively, the command language is shown for a single cell operation. In the multi-cell situation, such as exists in apparatus 140, the command language is different and difficult to show on a single paper sheet diagram. The command language for the multi-cell program includes multi-tasking.

When "pump more solution" is called for, then the program expands out to the column shown on the right side of FIG. 32 which can be regarded as covering the charging step. The pumping cycle for a valve 131 moving liquid from reservoir 116 into and through the block 112 is here implicitly shown by the language "turn PMW valve on to correct flow rate."

In the present program, the operator sets operating parameters into the command file. Read out is cumulative. The operator picks a particular predetermined protocol for his use and inputs his selection into the command file.

Applications and Methodology

As shown herein, the present invention provides a process for the sequential multi-step processing of a slide surface portion. The process involves locating a slide surface portion at a station as a wall member of a chamber and then contacting such surface portion in such chamber sequentially with at least two process fluids which are moved into and out of such chamber.

The sequential contacting can be accomplished by flowing each such fluid into, through, and out of such chamber. The flowing takes place in such chamber preferably along a flowpath which tends to be laminar so as to achieve approximately equal treatment of all areas of such surface portion. A present preference is to employ a flowpath that extends substantially across such slide surface portion from one side thereof to an opposing side thereof. During such flowing, the rate of fluid flow is preferably regulated.

The sequential contacting can also be accomplished by a combination of injecting such a fluid into such chamber, followed by removing such so injected fluid from such chamber preferably after a contacting time period. During the contacting time period, the volume of such chamber can be and preferably is reduced relative to the chamber volume prior to such contacting time period or even after such contacting time period.

The fluids employed can each be a liquid (preferred) or a gas.

During such contacting, the temperature of such chamber is preferably regulated. Preferably, each of such process fluids prior to such contacting is temperature regulated.

When a process fluid is so injected and removed, the removal is achievable either by suction, as with a syringe, or the like, or by flowing a washing fluid or the like (preferably liquid) through such chamber. If the chamber has been reduced in volume during a contacting time period, the chamber volume is conveniently and preferably enlarged for such a flowing.

In one presently preferred class of sequential processing, at least two such fluids are each successively so flowed through such chamber, then one such fluid (preferably a liquid) is so injected into said chamber and so removed therefrom after expiration of such a contacting time period, and then at least two of such fluids (preferably liquids) are each so flowed through such chamber.

The apparatus and the associated methodology of use provided by this invention can be used to perform many different kinds of sequential multi-step processing. In the case of slides with surface mounted specimen material, the slide surfaces are sequentially and automatically contacted with selected fluids which are flowed (circulated) through a small chamber formed in the individual slide processing station adjacent selected slide surface portions while maintaining controlled conditions, such as temperature, flow rate, and the like, as indicated herein.

For example, selective hybridization of nucleic acid probes to complimentary nucleic acid targets that are adhered to a slide surface can be carried out. Thus, a prepared slide bearing a conventionally prepared such target-containing coating on selected slide surface portions is located sealingly at a processing chamber in a processing station block. Preferably, the starting chamber volume that is defined between the slide and the block is in the range of about 200 to about 500 microliters, although larger and smaller chamber volumes can be used. Preferably, the chamber is associated with temperature control means. A predetermined succession of processing fluids are moved into and away from the processing chamber of the station. In the case of apparatus 140, these fluids first pass through a station delivery reservoir 116 before entering the processing chamber 112, as explained. A predetermined process step sequence under controlled conditions is thus carried out.

At least one of such steps can involve the contacting of the slide surface with a liquid probe containing composition; another of such steps, the incubation of the probe/target system; and still another of such steps, the washing of the resulting slide surface to separate residual probes therefrom.

In one presently preferred hybridization processing mode the step sequence is as follows:

(a) Prior to contacting the slide surface with the liquid probe containing composition flowing is ceased, and there is introduced (injected) into chamber a volume of the liquid probe-containing composition that is preferably not more than about 100 microliters but not less than about 10 microliters.

(b) The volume of the chamber is reduced to a value which is about equal to the volume of said probe-containing composition so introduced.

(c) The so filled and so reduced chamber is subjected to incubation conditions for a time and at a temperature adapted to cause hybridization between the probes and the nucleic acid targets.

(d) Thereafter the volume of such chamber is increased to a size that is in the range of about 200 to about 500 microliters.

(e) Then at least one predetermined wash liquid is flowed through such chamber so as to wash the resulting so probed treated slide surface.

For example, a multi-step process sequence is interrupted, or put on hold, at a predetermined point thereof, and, during such interruption, the station chamber is directly charged manually or automatically with a small quantity of a liquid probe containing composition (characteristically aqueous) without first charging such probe containing composition into the station delivery reservoir. Apparatus and methodology for manually directly charging such chamber can be employed such as is hereinabove described. The quantity of probe containing composition so charged is typically a fraction of the quantity of any one of the processing liquids that is successively moved (pumped) through the chamber from the station delivery reservoir. For example, this quantity can be in the range of about 100 microliters down to about 10 microliters and a present preference is to employ a quantity in the range of about 10 to about 30 microliters. Promptly after such direct charging, the volume of the chamber is preferably reduced down to a volume which corresponds to the volumetric quantity of the probe containing composition employed.

As the opposing respective surfaces of the coated slide and the chamber 46 of a station 36 bottom wall portion come together, the input probe-containing composition is compressed therebetween and is spread out over the coated slide surface portions in the chamber. Then, after an incubation period, the chamber can be expanded to a larger volume so that the resulting so treated slide surface portions can undergo further sequential multi-step processing. Such further processing typically includes washing to remove residual probes. During such operations and especially during the steps involving probe contacting, the processing chamber (and associated slide) are preferably subject to carefully controlled temperature maintenance.

The apparatus and methods of this invention enable one to carry out a plurality of separate slide surface sequential multi-step processing concurrently. Each such slide surface is positioned at a separate processing station wherein a chamber is provided adjacent the slide surface portions undergoing processing. A plurality of different slides can each be undergoing simultaneously the same sequential multi-step processing sequence. Alternatively, a plurality of different slides can each be undergoing a different sequential multi-step processing sequence.

Advantageously, in using the apparatus and methodology such as provided by this invention for hybridization, immuno-staining, or the like, the prior art techniques for the preparation of starting slides and slide mounted specimen material can be employed. Also, prior art processing fluids can be employed. Although prior art processing steps and conditions can be employed the present invention permits variations in such to be employed if desired. Exemplary such technology has been hereinabove briefly reviewed. The ability to so utilize such prior art technology in operating and practicing the present apparatus and methodology is advantageous because it avoids the necessity and cost of developing new and specialized technology for use with the present invention.

The illustrative embodiments of hybridization hereinbelow provided teach and illustrate utilization of this invention.

Embodiments

The invention is further illustrated and better understood by the following Examples:

Starting Materials

Conventional glass slides having a width of 25 mm, a length of 76 mm and a thickness of 1 mm are each coated on one face thereof with a composition containing as a nucleic acid target human white blood cells. The coating composition is a dried uniform coated layer of about 0.001 inch (about 25 microns) thickness and about 400 mm$^2$ surface area. This coating is prepared utilizing the teachings of D. Pinkel, J. Landegent, C. Collins, J. Fuscoe, R. Segraves, J. Lucas, and J. Gray in "Fluorescence in situ hybridization with human chromosome-specific libraries: Detection of trisomy 21 and translocations of chromosome 4" published in Proc. Natl. Acad. Sci. Usa, Vol. 85, pp. 9138-9142 (1988). This reference gives descriptions for the slide preparation and for various individual reagents.

Salmon sperm DNA is purchased in dry form from Sigma Chemical Co. (P.O. Box 14508 St. Louis, Mo. 63178) and is solubilized in water to obtain a solution of 10 mg/ml.

Formamide is purchased from International Biotechnologies, Inc., New Haven, Conn. 06535.

Fluorescein streptavidin is purchased from Vector Labs (1429 Rollins Road, Burlingame, Calif. 94010) as a 2 mg/ml solution and is diluted with PNM buffer to give a final solution concentration of 5 µl/ml FITC-streptavidin in PNM 20X SSC is prepared as a 3M NaCl and 0.3M Na Citrate solution whose pH is adjusted to 5.3 with HCl.

70% (v/v) Formamide and 2X SSC is prepared by adding 49 ml formamide and 7 mL of 20X SSC at pH 5.3 to 14 mL water to make 70 ml of solution.

50% (v/v) Formamide and 2X SSC is prepared by adding 105 mL of formamide and 21 mL of 20X SSC at pH 5.3 to 84 mL of water to make 210 ml of solution.

To prepare 10 liters of 1X PN buffer, 0.1M sodium phosphate and 0.1% (v/v) NP40 (Calbiochem catalog) are admixed to produce a solution whose pH is about 8.0 to 8.1.

PNM buffer is prepared by supplementing the PN buffer with 5% nonfat dry milk and 0.02% (w/v) sodium azide.

Counterstain-antifade solution is prepared by admixing together:
0.2 ug/mL NaCl
1 mg/ml p-phenylenediamine dihydrochloride
13.7 mM NaCl
0.27 mM KCl
1 mM $KH_2PO_4$ and 90% v/v glycerol.
Solution pH is adjusted to 8.0 with 0.5M carbonate-bicarbonate buffer.

Carbonate-bicarbonate buffer is prepared by dissolving 0.5M $NaHCO_3$ in water and adjusting the pH to 9 with NaOH.

Each probe employs the same DNA sequence. This sequence is complementary to a specific target DNA sequence that, illustratively for these examples, is a specific alpha satellite sequence associated with the centromeric region of human chromosome number 8. This DNA sequence is purified preliminarily using buoyant density centrifugation procedures known to the prior art; see, for example, D. Pinkel et al. (opus cited). One probe is prepared by biotinylating this DNA sequence. A second probe is prepared by fluorophorinating this DNA sequence. A third probe is prepared by binding this DNA sequence with a hapten. Such probe preparations are accomplished using prior art procedures such as shown, for example, by D. Pinkel et al. (opus cited). Each such probe is formulated into an aqueous dispersion which contains 16 nanograms of probe per 10 microliters of liquid. Thus, for use in hybridizing a target DNA mounted on a slide that is positioned in a station having a chamber such as provided by the teachings of this invention where a chamber volume is about 50 microliters, each such chamber (as described hereinbelow) is charged (using a syringe or the like) with about 50 microliters of each such probe composition. Thus, a 50 microliter probe composition contains 80 nanograms of probe.

After hybridization with the biotinylated probe, the probe/target complex is contacted with FITC-streptavidin for color development purposes as a part of the hybridization procedure.

After hybridization with the fluorophor labeled probe, further label development processing is not necessary before post-hybridization examination under a fluorescence microscope or the like.

After hybridization with the hapten labeled probe, the probe/target complex is contacted with a primary antibody (in an aqueous composition) to bind the primary antibody to the hapten. The resulting complex is then contacted with a complex of secondary antibody and enzyme (in an aqueous composition). The secondary antibody in such complex is specifically bondable to the so-called F C fragment in the primary antibody. The resulting complex is then further contacted with a chromophore-containing substrate (in an aqueous composition). Resultingly, chromophoric bodies are released that are detectable by use of a subsequent post-hybridization procedure (microscopic examination, or the like, as desired).

Hybridization

Example 1: Sequential Multi-Step Hybridization of Target DNA mounted on a slide in a Processing Chamber Using a slide processing station block assembly, such as block 191 (FIG. 11), but without the associated delivery reservoir 116, a hybridization procedure is carried out with the temperature of the block being regulated and with process fluids being directly input into and flowed through the block with the slide undergoing hybridization being held in place. Probe introduction and removal are accomplished with a syringe. The parallelogram slide supporting mechanism as shown in FIGS. 4A, B, and C is used.

Using such station block assembly, a slide prepared as described above is positioned and held with the slide coating facing into the processing chamber 46.

Using 500 milliliter—size reservoir bottles:
(a) Reservoir bottle R 1 is charged with 100 ml of the 70% formamide and 2X SSC solution of (above described).
(b) Reservoir Bottle R 2 is charged with 500 ml of 70% ethanol.
(c) Reservoir bottle R 3 is charged with 500 ml of 85% ethanol.
(d) Reservoir bottle R 4 is charged with 500 ml 100% ethanol.
(e) Reservoir bottle R 5 is charged with 500 ml of the 50% formamide and 2X SSC solution (above described).
(f) Reservoir bottle R 6 is charged with 500 ml of the PN buffer solution (above described).
(g) Reservoir bottle R 7 is charged with 70 ml of the FITC-streptavidin solution (above described).

The pressurized gas line 127 is pressurized with air at about 6 psig (41340 Pascals gauge). This line 127 is directly connected with each reservoir which is then directly connected with such station block. The biotinylated probe composition above described is employed and the volume of the slide chamber which is charged therewith is about 50 microliters.

The following multi-step process sequence shown in Table I below is carried out:

11. The pressurized gas line 127 is pressurized with air at about 7.5 psig.

TABLE I

Slide Surface Hybridization with Station Block

| Step No. | Apparatus Action or Function Taken In Step | Estimated Total Step Time (Minutes) | Block[1] Temp. °C. | Reservoir Bottle | Estimated Amount Reagent Used Vol/Slide (ml) |
|---|---|---|---|---|---|
| 1 | Heat slide block | 1 | 75° | | |
| 2 | Wash with SSC-formamide | 8 | 75° | R 1 | 2 |
| 3 | Wash with 75% ethanol | 8 | 25° | R 2 | 2 |
| 4 | Wash with 85% ethanol | 8 | 25° | R 3 | 2 |
| 5 | Wash with 100% ethanol | 8 | 25° | R 4 | 2 |
| 6 | Empty slide block | 1 | 25° | | |
| 7 | Inject probe | 1 | 25° | | |
| 8 | Heat probe | 5 | 75° | | |
| 9 | Hybridization[2] | 60 | 42° | | |
| 10 | Empty block | 1 | 25° | | |
| 11 | Wash with SSC-formamide | 8 | 45° | R 5 | 2 |
| 12 | Wash with PN buffer | 8 | 45° | R 6 | 2 |
| 13 | Wash with FITC-streptavidin | 4 | 37° | R 7 | 1 |
| 14 | Wash with PN buffer | 8 | 37° | R 8 | 2 |
| 15 | Empty slide block | | 25° | | |

Table I footnotes:
[1]Temperature of the delivery reservoir is independent of the temperature of the station block.
[2]During hybridization the temperature of the station block and the delivery reservoir are maintained at the indicated set points, but no fluids are pumped through the station block.

After the completion of step 15 (see Table I), the product slide is removed from the processing station. About 10 microliters of counterstain-antifade solution are applied over the processed surface area of the slide. The counterstain-antifade solution is as above described. Thereafter, the processed surface area of the product slide is covered with a glass coverslip and examined under a fluorescence microscope.

This microscopic examination reveals two dots that confirms the presence of two number 8 chromosomes, as expected for a normal karyotype. Therefore, the hybridization procedure conducted at a single station is successful.

Also, it appears that the station block employed may improve hybridization rates, thus allowing for shorter hybridization times than achievable in the prior art.

Example 2: Automatically Conducted Hybridization

To illustrate the capacity of apparatus of this invention to perform hybridization automatically, the following procedure is carried out:

Apparatus similar to apparatus embodiment 140 is employed Each of the six stations 141.1–141.6 here utilized is equipped with a station block assembly 36, a delivery reservoir 116, a valve 131, and a needle valve 139. Also, each block 37 and each reservoir 116 is equipped with a temperature controller which can accept its own digital data from a serial port on a control computer and convert such to a set point. The control system is similar to the system 276. Each of the reservoirs R 1 through R 11 is a 250 ml plastic bottle with a screw-on cap which is fitted with 91) a dip tube and (2) a valve corresponding to each of valves V 1 through V 11.

Each of six reservoir bottles, identified as R 1 through R 6, is filled with a process liquid as identified in Table II below.

Each station 141.1 through 141.6 has duly mounted thereat a coated slide prepared as above described.

The biotinylated probe composition above described is employed to fill slide chamber volumes of about 50 microliters each.

Into the command file of this supervisory program 280 are input control commands for each process step identified in the sequential multi-step procedure shown in Table III (below) such command file entries being shown in Table IV below.

Before the program for such multi-step procedure is started, the conduits C 1 though C 7 are first bled using computer control and the bleed sequence shown in FIG. 30. Thereafter, using the program sequence illustrated in FIGS. 29 and 31, such multi-step procedure is carried out.

The product slides are found to contain hybridized targets when examined under the fluorescence microscope. The hybridization procedure is successful.

TABLE II

Treating Compositions

| Reservoir Bottle | Reagent Identity | Estimated Amount Reagent Used Vol/Slide (ml) |
|---|---|---|
| R 1 | 70% formamide, 2X SSC[2] | 2 |
| R 2 | 70% ethanol[1] | 3 |
| R 3 | 100% ethanol[1] | 3 |
| R 4 | 50% formamide, 2X SSC[2] | 2 |
| R 5 | PN buffer[2] | 25 |
| R 6 | FITC-streptavidin[2] | 2 |

Table II footnotes:
[1]Stock reagent.
[2]Prepared as above described.

TABLE III

Hybridization Step Sequence with Biotinylated Probe

| Step No. | Process Conducted | Run Time (min.) Cumulated | Individual Step Time (min.) | Hybridization Chamber Temp. °C. | Hybridization Chamber Fluid Source | Flow Rate (ml/min.) | Total Volume (ml) |
|---|---|---|---|---|---|---|---|
| 1 | Place slide into cell | 1 | | ambient | air | | |
| 2 | Heat cell to 75° C. | 3 | 2 | 75° | none | | |
| 3 | Wash with SSC-formamide | 8 | 5 | 75° | R 1 | 0.2 | 1 |
| 4 | Cool cell | 9 | 1 | ambient | R 1 or air | 1 | 1 |

TABLE III-continued

Hybridization Step Sequence with Biotinylated Probe

| Step No. | Process Conducted | Run Time (min.) Cumulated | Individual Step Time (min.) | Hybridization Chamber Temp. °C. | Hybridization Chamber Fluid Source | Flow Rate (ml/min.) | Total Volume (ml) |
|---|---|---|---|---|---|---|---|
| 5 | Wash with 70% ethanol | 12 | 3 | ambient | R 2 | 1 | 3 |
| 6 | Wash with 100% ethanol | 15 | 3 | ambient | R 3 | 1 | 3 |
| 7 | Empty cell | 16 | 1 | ambient | air | | |
| 8 | Inject probe | 17 | 1 | ambient | probe mix | | |
| 9 | Heat probe | 22 | 5 | 75° | probe mix | | |
| 10 | Hybridization | 202 | 180 | 42° | probe mix | | |
| 11 | Flush cell | 203 | 1 | 45° | air | | |
| 12 | Wash with SSC-formamide | 218 | 15 | 45° | R 4 | 0.1 | 1.5 |
| 13 | Wash with PN buffer | 233 | 15 | 37° | R 5 | 1 | 15 |
| 14 | Wash with FITC-streptavidin | 253 | 20 | 37° | R 6 | 0.1 | 2 |
| 15 | Wash with PN buffer | 263 | 10 | 37° | R 5 | 1 | 10 |
| 16 | Empty cell | 263 | | ambient | air | | |

TABLE IV

Command File Entries

| Step Shown in Table IV | Command | Comments |
|---|---|---|
| 1 | None | Done before starting program 2 |
| 2 | Step<br>Dry<br>Time 2 min.<br>Temp 75° C. | Heats slide cell to 75° C. over 2 minutes<br>With neither fluid nor air flowing<br>Across the slide |
| 3 | Step<br>Wash<br>Solution #1<br>Volume 1.0 ml<br>Time 5 min. | Wash with solution #1 (70% formamide, 2X SSC) for 5 minutes<br>Maintain last temperature given<br>Use 1.0 ml, flow rate for 5 min. |
| 4 | Step<br>Air<br>Time 1 min.<br>Temp 25° C. | Flush with air while cooling to 25° C. (assumed to be ambient) |
| 5 | Step<br>Wash<br>Solution #2<br>Volume: 3 ml<br>Time: 3 | |
| 6 | Step<br>Wash<br>Solution #3<br>Volume: 3 ml<br>Time: 3 min. | |
| 7 | Step<br>Air<br>Time: 1 min. | Blow dry for 1 minute. Air turns off at end of time period |
| 8 | Step | Wait inject displays message following "wait" halts execution until a key is pressed (regardless of msg) |
| 9 | Step<br>Dry<br>Time: 5 min.<br>Temp: 75° C. | Heats probe to 75° C. over 5 minutes |
| 10A | Step<br>Dry<br>Time: 2 min.<br>Temp.: 42° C. | Cooling the probe is part of step 10 in Table III |
| 10B | Step<br>Dry<br>Time: 180 | Hybridization: Sit for 3 hours |
| 11 | Step<br>Air<br>Time: 1<br>Temp.: 45° C. | Flushes with air while ramping Temperature to 45° C. |
| 12 | Step<br>Wash<br>Solution #4<br>Volume: 1.5 ml<br>Time: 15 min. | |
| 13 | Step<br>Wash<br>Solution #5<br>Volume: 15 ml<br>Time 15 min<br>Temp.: 37° C. | The temperature is ramped down as part of step 13 in Table III |
| 14 | Step<br>Wash<br>Solution #6<br>Volume: 2 ml | |

TABLE IV-continued

Command File Entries

| Step Shown in Table IV | Command | Comments |
|---|---|---|
| | Time: 20 min. | |
| 15 | Step Wash Solution 5 Volume: 10 ml Time: 10 min. | |
| 16 | Step Air Temp.: 25°C. Stop | This step is needed to flush cell, bring temp down, and stop program |
| 17 | (none - done at end of program) | |

Example 3: Multiple Simultaneously Conducted Hybridizations

To illustrate the capacity of apparatus of this invention to conduct multiple simultaneous hybridizations, the following procedure is carried out:

The apparatus and supervisory computer program employed are as described in Example 2.

The fillage of each of the reservoir bottles is as shown in Table V below.

Each of the 12 stations 141.1 through 141.12 is associated with a glass slide whose size and coating are as above described.

A first set of four slides in stations 141.1 through 141.4 is processed by a multi-step hybridization procedure which uses the above described biotinytated probe composition at the rate of about 50 microliters per 50 microliter slide chamber volume followed by treatment with the fluorophor labeled streptavidin composition above described. A summary of the program steps is provided in Table VI below. Commands are input into the command file of program 280.

A second set of four slides in stations 141.5 through 141.8 is processed by a multi-step hybridization procedure which uses a probe composition as above described wherein the probes are directly labeled with fluorophors above described. A summary of the program steps is provided in Table VII below. Commands are input into the command file of program 280.

A third set of four slides in stations 141.9 through 141.12 is processed by a multi-step hybridization procedure which uses a probe composition containing the hapten labeled probes as described above followed by treatment with the enzyme-anti-hapten antibody conjugate aqueous composition described above. A summary of the program steps is provided in Table VIII below. Commands are
into the command file of program 280.

After apparatus conduit bleeding as described in Example 2, these three programmed sequences are simultaneously executed by the apparatus automatically.

Each of the resulting so processed slides of such first set is viewed under a fluorescent microscope with the appropriate filter sets. Fluorescent spots are observed on the two human chromosomes number 8 directly over the centromeric region, when those chromosomes are in metaphase. Two spots are seen in most interphase nuclei.

The presence of abnormal cells is detected by the presence of more or less spots than expected, either in metaphase spreads or in interphase nuclei.

Each of the so processed slides of such second set is viewed under a fluorescent microscope using the same procedure as employed with the slides of such first set. Comparable observations are made.

Each of the so processed slides of such third set is viewed under a light microscope because, unlike the slides of such first and second sets, detection is based on the generation of chromophores. Thus, under a light microscope, either one colored spot is typically observed over the centromeric region of each metaphase chromosome No. 8, or two colored spots are typically observed generally over the centromeric region of each interphase chromosome No. 8. specimen.

TABLE V

| Reservoir Fillage | |
|---|---|
| Reservoir Bottle | Reservoir Identity |
| R 1 | 70% formamide, 2 X SSC |
| R 2 | 70% ethanol |
| R 3 | 100% ethanol |
| R 4 | 50% formamide, 2 X SSC |
| R 5 | 2 X SSC buffer |
| R 6 | PN buffer |
| R 7 | FITC-streptavidin |
| R 8 | Water (distilled) |
| R 9 | 2 X SSC 0.1% NP40 |
| R 10 | Horse radish peroxidase conjugated anti-hapten |
| R 11 | Color development buffer |
| R 12 | 70% acetic acid |

TABLE VI

Hybridization Procedure: Biotinylated Probes and Fluorophore Labeled Avidin

| Step | Process | Run Time (min.) | Step time (min.) | Hybridization Block Temp. °C. | Fluid Source |
|---|---|---|---|---|---|
| 1 | Place slide into cell | 1 | | ambient | air |
| 2 | Heat cell to 70° C. | 2 | 1 | 70° | none |
| 3 | Wash with SSC-formamide | 7 | 5 | 70° | R 1 |
| 4 | Cool cell | 8 | 1 | ambient | R 1 or air |
| 5 | Wash with 70% ethanol | 11 | 3 | ambient | R 2 |
| 6 | Wash with 100% ethanol | 14 | 3 | ambient | R 3 |

TABLE VI-continued

Hybridization Procedure: Biotinylated Probes and Fluorophore Labeled Avidin

| Step | Process | Run Time (min.) | Step time (min.) | Hybridization Block Temp. °C | Fluid Source |
|---|---|---|---|---|---|
| 7 | Empty cell | 15 | 1 | ambient | air |
| 8 | Inject probe | 16 | 1 | ambient | probe mix |
| 9 | Heat probe | 21 | 5 | 70° | probe mix |
| 10 | Hybridization | 201 | 180 | 37° | probe mix |
| 11 | Flush cell | 202 | 1 | 37° | air |
| 12 | Wash with SSC-formamide | 217 | 15 | 45° | R 4 |
| 13 | Wash with 2X SSC | 232 | 15 | 45° | R 5 |
| 14 | Wash with PN buffer | 232 | 15 | 45° | R 6 |
| 15 | Wash with PN buffer | 247 | 15 | 37° | R 6 |
| 16 | Wash with FITC-streptavidin | 267 | 20 | 37° | R 7 |
| 17 | Wash with PN buffer | 271 | 4 | 37° | R 6 |
| 22 | Empty cell | 271 |  | ambient | air |

TABLE VII

Hybridization Procedure: Probes Directly Labeled With Fluorophors

| Step | Process | Run Time (min.) | Step Time (min.) | Hybridization Block Temp. °C | Fluid Source |
|---|---|---|---|---|---|
| 1 | Place slide into cell | 1 |  | ambient | air |
| 2 | Heat cell to 75° C. | 3 | 2 | 70° | none |
| 3 | Wash with SSC-formamide | 8 | 5 | 70° | R 1 |
| 4 | Cool cell | 9 | 1 | ambient | R 1 or air |
| 5 | Wash with 70% ethanol | 12 | 3 | ambient | R 2 |
| 6 | Wash with 100% ethanol | 15 | 3 | ambient | R 3 |
| 7 | Empty cell | 16 | 1 | ambient | air |
| 8 | Inject probe | 17 | 1 | ambient | probe mix |
| 9 | Heat probe | 22 | 5 | 70° | probe mix |
| 10 | Hybridization | 202 | 180 | 42° | probe mix |
| 11 | Flush cell | 203 | 1 | 45° | air |
| 12 | Wash with SSC-formamide | 206 | 3 | 45° | R 4 |
| 13 | Wash with 2X SSC | 207 | 1 | 45° | R 5 |
| 14 | Wash with 2X SSC-NP40 | 208 | 1 | 45° | R 9 |
| 15 | Empty cell |  |  | ambient | air |

TABLE VIII

Hybridization Procedure: Hapten Labeled Probes and Enzyme Labeled Anti-Hapten Antibody Conjugate

| Step | Process | Run Time (min.) | Step Time (min.) | Hybridization Block Temp. °C | Fluid Source |
|---|---|---|---|---|---|
| 1 | Place slide into cell | 1 |  | ambient | air |
| 2 | Heat cell to 75° C. | 3 | 2 | 70° | none |
| 3 | Wash with SSC-formamide | 8 | 5 | 70° | R 1 |
| 4 | Cool cell | 9 | 1 | ambient | R 1 or air |
| 5 | Wash with 70% ethanol | 12 | 3 | ambient | R 2 |
| 6 | Wash with 100% ethanol | 15 | 3 | ambient | R 3 |
| 7 | Empty cell | 16 | 1 | ambient | air |
| 8 | Inject hapten-labeled probe | 17 | 1 | ambient | probe mix |
| 9 | Heat probe | 22 | 5 | 70° | probe mix |
| 10 | Hybridization | 202 | 180 | 42° | probe mix |
| 11 | Flush cell | 203 | 1 | 45° | air |
| 12 | Wash with SSC formamide | 206 | 3 | 45° | R 4 |
| 13 | Wash with 2X SSC | 207 | 1 | 45° | R 5 |
| 14 | Wash with 2X SSC-NP40 | 208 | 1 | 45° | R 9 |
| 15 | Wash with PN buffer | 210 | 2 | ambient | R 6 |
| 16 | Wash with enzyme conjugating antibody | 230 | 20 | ambient | R 10 |
| 17 | Wash with PN buffer | 236 | 6 | ambient | R 6 |
| 18 | Wash with color development buffer | 241 | 5 | ambient | R 11 |
| 19 | Wash with water | 242 | 1 | ambient | R 8 |
| 20 | Wash with acetic acid | 243 | 1 | ambient | R 12 |
| 21 | Wash with water | 244 | 1 | ambient | R 8 |

Staining

Example 4: Automatically Conducted Immuno-Staining

To illustrate the capacity of apparatus of this method to perform immuno-staining, the following procedure is carried out:

The apparatus and supervisory program employed are as described in Example 2.

The fillage of each of the reservoir bottles is as shown in Table IX below.

Each of processing stations 141.1 through 141.4 is associated with a glass slide whose size is as above described and whose coating is as described in the product like above, obtained with the slides and reagents from DAKO Corporation (Carpinteria, Calif.).

The slides were coated with HPV-virus such as injected tissue sections from bovine tissue. Prepared and ready to use slides can be purchased from DAKO Corporation.

Each of such slides is processed by a multi-step immuno-staining procedure which uses primary and secondary antibodies (linker antibody) and tertiary antibody-enzyme complexes. Color development is achieved using the enzyme antibody complex. A summary of the program steps is provided in Table X below. Commands are input into the command file of program 280.

Slides are evaluated by light microscopy. The areas where the characteristic brown color appears shows the presence of antigen. When the primary antibody is directed against HPV virus, as in this case, the color indicates the presence of such viruses in the tissue sections.

No undue limitations are to be drawn from the foregoing description.

TABLE IX

| Reservoir | Reservoir Fillage Reagent |
|---|---|
| R 1 | 3% hydrogen peroxide[1] |
| R 2 | Water (distilled) |
| R 3 | 0.05M Tris-HCl, pH 7.6[2] |
| R 4 | Primary antibody[1] |
| R 5 | Link antibody[1] |
| R 6 | Antibody-enzyme complex (PAP)[1] |
| R 7 | Color development buffer (substrate mixture)[1] |
| R 8 | Meyers hematoxylin solution[3] |
| R 9 | 34 mM ammonium hydroxide[2] |

Table IX footnotes:
[1] The source of this reagent is the DAKO Corporation, 6392 Via Rea Carpinteria, CA 93013.
[2] Laboratory reagent prepared with distilled water.
[3] The source of this reagent is Sigma Chemical Corporation.

TABLE X

Immuno-Staining Procedure: Primary and Secondary Antibodies and Enzyme Color Development

| Step | Process | Run Time (min.) | Step Time (min.) | Hybridization Block Temp. °C. | Fluid Source |
|---|---|---|---|---|---|
| 1 | Wash with hydrogen peroxide | 5 | 5 | ambient | R 1 |
| 2 | Wash with water | 6 | 1 | ambient | R 2 |
| 3 | Wash with Tris buffer | 11 | 5 | ambient | R 3 |
| 4 | Wash with primary antibody | 31 | 20 | ambient | R 4 |
| 5 | Wash with Tris buffer | 36 | 5 | ambient | R 3 |
| 6 | Wash with link antibody | 56 | 20 | ambient | R 5 |
| 7 | Wash with Tris buffer | 61 | 5 | ambient | R 3 |
| 8 | Wash with PAP | 81 | 20 | ambient | R 6 |
| 9 | Wash with Tris buffer | 86 | 5 | ambient | R 3 |
| 10 | Wash with color development buff | 116 | 30 | ambient | R 7 |
| 11 | Wash with water | 117 | 1 | ambient | R 2 |
| 12 | Wash with hematoxylin solution | 119 | 2 | ambient | R 8 |
| 13 | Wash with water | 120 | 1 | ambient | R 2 |
| 14 | Wash with ammonium hydroxide | 125 | 5 | ambient | R 9 |
| 15 | Wash with water | 130 | 5 | ambient | R 2 |
| 16 | Empty cell | | | ambient | air |

What is claimed is:

1. Apparatus for sequential multi-step processing of biological material mounted on a surface of a slide comprising:
   (a) a plurality of processing stations, each of said processing stations comprising:
      (1) block means defining a cavity and having fluid pathway means for inputting and removing fluid from said cavity, and
      (2) releasable holding means for positioning a slide bearing said biological material adjacent said cavity to define a chamber;
   (b) a plurality of fluid supply reservoir means, each including conduit means for conducting fluid therefrom to said chamber;
   (c) valve means for selectively individually interconnecting each one of said supply reservoir means with each one of said processing stations so that fluid can flow from a selected one of said reservoirs to said pathway means of at least one of said processing stations into said chamber, including associated conduit means; and
   (d) regulatable pump means for pumping fluid from a so interconnected supply reservoir to said so interconnected pathway means; whereby material can be processed at each of said processing stations identically or variously relative to material being processed at other processing stations.

2. The apparatus for sequential, multi-step processing of biological material mounted on a surface of a slide of claim 28 wherein the relationship between said slide and said holding means is such that the initial volume of said chamber is not greater than about 500 microliters.

3. The apparatus of claim 1 wherein each said processing station further includes gasket means for making a fluid tight seal about the perimeter of said chamber.

4. The apparatus of claim 3 wherein each said gasket means is elastomeric and compressible, and the relationship between each said holding means and a slide associated therewith is such that each said chamber has a volume which can be varied by the amount of holding force applied to such slide by said holding means.

5. The apparatus of claim 1 wherein each said processing station further includes temperature regulating means.

6. The apparatus of claim 1 which further includes control means for operational sequencing and regulating.

7. The apparatus of claim 6 wherein said control means is computer driven.

8. The apparatus of claim 7 wherein said computer is programmable so that said apparatus can execute a predetermined sequential multi-step operating procedure.

9. The apparatus of claim 1 wherein said block means of one of said processing station further includes (a) a channel extending vertically therethrough from the block back face to said block interior portion, and (b) check valve means in said channel which limits passage of fluid therethrough to one direction proceeding from said back face to said interior portion.

10. The apparatus of claim 1 wherein each said station further includes:

(a) means for introducing into, and removing from, said chamber a volume of a liquid composition which is not substantially larger than the volume of said chamber, and (b) liquid containment means for retaining such liquid composition so introduced into such a chamber a predeterminable length of time.

11. The apparatus of claim 1 wherein (a) each said station further includes:
delivery reservoir means,
first fluid conduit means interconnecting input portions of said pathway means with said delivery reservoir means,
second fluid conduit means interconnecting said supply reservoir means with said valve means, and
controllable pumping means for transferring liquid from said delivery reservoir means, through said first fluid conduit means, and through said chamber, so that fluid flows from a so interconnected supply reservoir through said valve means to said delivery reservoir means before passing through said chamber at each station, and (b) control means is provided for operating said apparatus.

12. The apparatus of claim 11 wherein at least one of said stations further includes
recycle reservoir means,
conduit means associating said recycle means with effluent from said removing pathways, and
controllable switching valve means associated with said recycle reservoir means, and associated return conduit means connected to said valve means, so that fluid received in said recycle reservoir can be recycled from said recycle reservoir means to the originating one of said supply reservoirs.

13. Apparatus for the multi-step, sequential processing of biological material mounted on a surface of a slide by fluid contacting comprising in combination:

(a) a processing station having a definable chamber through which fluids can be passed, including station inlet and outlet means for said chamber, (b) station reservoir means having an outlet means that is connected by a station conduit means to said station inlet means and further having two inlet means, (c) restriction means associated with said station conduit means for regulating fluid flow through said processing station, (d) a multiple position valve means having a plurality of input ports and a single output port and including internal means for adjustably interconnecting individual ones of said input ports with said output port, and further including external conduit means connecting said single output port to said reservoir inlet means, (e) a plurality of individual fluid supply reservoir means, each one thereof having reservoir inlet and outlet means, and the outlet means for each said supply reservoir means being connected by external conduit means to a different one of said multiple position valve input ports, (f) a plurality of openable and closable valve means, each one thereof being associated with a different inlet means of one of said supply reservoirs, and an additional one thereof being associated with one of said multiple position valve input ports, (g) a variable fluid flow regulating valve means associated with the second of said reservoir inlet means, (h) a pressurizing fluid bus line connected with the input side of each one of said open/close valve means, said bus line including means for connection thereof to a source of regulated pressurized fluid, and (i) means for regulating the operation of each of
said openable and closable valve means,
said multiple position valve means, and
said variable flow regulating valve means, so that a fluid selected from the fluid group consisting of fluid in each one of said supply reservoir means and said pressurized fluid is passable through said processing station at a predetermined flow rate, and so that other individual fluids of said group can each be subsequently sequentially individually passed through said processing station at a predetermined rate.

14. Apparatus for the sequential, multi-step controlled processing of biological material mounted on a surface of a slide comprising in combination:

(a) a plurality of processing stations, each of said stations having
(1) block means defining a processing chamber wherein a slide bearing said biological material is located associated with said block means,
(2) delivery reservoir means, and
(3) pulse width modulatable solenoid actuated valve means associated with said delivery reservoir means for releasing regulated amounts of compressed gas into said delivery reservoir means so that liquid is transferred by applied gas pressure form said delivery reservoir to said processing chamber;

(b) a plurality of liquid supply reservoirs;

(c) a solenoid actuated openable and closable valve means associated with each one of said reservoirs, and one further solenoid actuated openable and closable valve means;

(d) a first solenoid stepped rotary switching valve means having a single output port and multiple input ports, each of said reservoirs being associated by conduit means with a different one of said multiple input ports, and said one further valve means being associated by conduit means with another one of said multiple input ports, (e) a second solenoid stepped rotary switching valve means having multiple output ports and a single input port, each of said delivery reservoir means of said processing stations being functionally associated with a different one of said multiple output ports, and said single input port thereof being associated with said single output port of said first solenoid activated switching valve means;

(f) gas conduit means for supplying compressed gas to each one of
(1) said pulse width modulatable valve means, and
(2) said openable and closable valve means; and (g) solenoid actuated shunt valve means functionally interconnected with such conduit means for purging and bleeding;

(h) a control system for said apparatus; so that by operation of said valves and application of compressed gas to said gas conduit means:

(1) liquid from any one of said supply reservoirs is transferable to any one of said delivery reservoir means;

(2) liquid rom any one of said delivery reservoirs is transferrable through said block means; and (3) liquid is purgeable and/or bleedable from associated selected such conduit means.

15. The apparatus of claim 14 wherein said control system comprises:

(a) means for controlling the pulse width modulation applied to the solenoid of each said pulse width modulated valve, (b) means for controlling the solenoid actuation of each of said openable and closable valve means, (c) means for controlling the solenoid stepping of each of said first and said second rotary switching valve means; and (d) programmable computer means for controlling and sequencing the operation of each of said controlling means.

16. The apparatus of claim 14 wherein each one of said processing stations is additionally provided with temperature control means for said block means and said delivery reservoir means.

17. The apparatus of claim 14 wherein one said processing station is operational, said single output pot of said first switching valve is functionally associated with said delivery reservoir means of said processing station, and said second switching valve is bypassed.

18. The apparatus of claim 14 wherein additionally: each one of said processing stations is provided with recycle reservoir means for receiving effluent liquid from said block means, each said recycle reservoir means is provided with a solenoid activated openable and closable diverter valve means that is located in an effluent conduit means, and conduit means is provided for controllably supplying compressed gas to said delivery reservoir means, so that effluent liquid passing from said recycle reservoir means can flow either to waste or to the originating one of said reservoir means via said first and said second switching valves when such are suitably positioned.

19. The apparatus of claim 16 wherein said control system comprises:

(a) means for operating each of said variable output valve means, said operating means comprising for each said variable output valve means:

(1) computer means for generating an analog voltage signal whose strength is proportional to a predetermined pumping rate for said variable output valve means, (2) means for generating a reference analog sawtooth voltage signal of predetermined frequency, (3) voltage comparator means for comparing said analog voltage signal to said sawtooth voltage signal and or generating a resulting output pulsed voltage whose pulse frequency is proportioned to said analog voltage signal, and (4) circuit means functionally interconnecting said voltage comparator means and said variable output valve means for operating the solenoid of said variable output valve means with said pulsed output voltage;

(b) means for selectively operating individual ones of said openable and closable valve means comprising:

(1) computer means for generating multiplexed digital signals which incorporate an address code for each of said openable and closable valve means and which can incorporate an order code directing a particular one of said openable and classable valve means to open or close, (2) demultiplexer means for receiving said multiplexed digital signals, for decoding said signals, and for generating an output signal for each one of said openable and closable valve means, and (3) circuit means functionally interconnecting said demultiplexer means with each one of said openable and closable valve means for making each one of said valve means responsive to respective ones of said output signals;

(c) means for operating each one of said first and said second switching valve means said operating means comprising for each said switching valve means:

(1) computer means for generating a digital signal which includes information identifying a particular position desired for such one of said valve means, (2) gate means for receiving said digital signals and for passing said digital signals when such one switching valve is in a home position, (3) non-retriggerable monostable multivibrator means for receiving said so passed signals and for generating therefrom output voltage pulses that step the solenoid of such one switching valve to said particular desired valve position, and (4) circuit means functionally interconnecting said multivibrator means with such one switching valve for making such one switching valve respond to said output voltage pulses; and (d) programmable computer means for regulating and sequencing the respective operations of:

(1) said means for operating each of said variable output valve means, (2) said means for selectively operating individual ones of said openable and closable valve means, and (3) said means for operating each one of said first and said second switching valve means.

20. The sequential, multi-step controlled processing apparatus of claim 14, whereby said apparatus can be used to process material at each said processing station identically or variously relative to material being processed at other processing stations.

* * * * *

US005273905C1

(12) REEXAMINATION CERTIFICATE (4776th)
United States Patent
Muller et al.

(10) Number: US 5,273,905 C1
(45) Certificate Issued: Apr. 29, 2003

(54) PROCESSING OF SLIDE MOUNTED MATERIAL

(75) Inventors: Uwe R. Muller, Kendall County, IL (US); Lawrence J. Mika, Naperville, IL (US); Donald J. Lindley, Naperville, IL (US); Ernest J. Wisner, Elgin, IL (US)

(73) Assignee: Vysis, Inc., Downers Grove, IL (US)

Reexamination Request:
No. 90/006,110, Sep. 13, 2001

Reexamination Certificate for:
Patent No.: 5,273,905
Issued: Dec. 28, 1993
Appl. No.: 07/660,718
Filed: Feb. 22, 1991

(51) Int. Cl.[7] .................. C12M 1/20; G01N 21/00; G01N 31/00; G01N 33/00
(52) U.S. Cl. ............... 435/286.5; 435/287.2; 422/63; 422/67; 422/99; 422/100
(58) Field of Search ............ 435/286.5, 287.2, 435/288.3, 305.4; 422/63, 67, 99, 100, 102; 436/63; 359/398

(56) References Cited

U.S. PATENT DOCUMENTS

| | | | |
|---|---|---|---|
| 3,588,259 A | * 6/1971 | Harvey | 356/244 |
| 4,629,686 A | 12/1986 | Gruenberg | 435/1 |
| 4,738,824 A | 4/1988 | Takeuchi | 422/63 |
| 5,068,091 A | 11/1991 | Toya | 422/99 |
| 5,192,503 A | * 3/1993 | McGrath et al. | 356/244 |

FOREIGN PATENT DOCUMENTS

| | | |
|---|---|---|
| EP | 0 077 477 A1 | 4/1983 |
| EP | 0 270 363 A2 | 6/1988 |

* cited by examiner

Primary Examiner—William H. Beisner

(57) ABSTRACT

An apparatus for the sequential multi-step processing of slide surface portions. The apparatus includes subassemblies and assemblies and a computer driven control system therefor. The apparatus permits at least one step of such a process sequence to be carried out with minimal amounts of processing liquids which is advantageous for specimen treatment with costly reagents, such as aqueous compositions containing probes. Immunochemical and in situ hybridization procedures can be carried out.

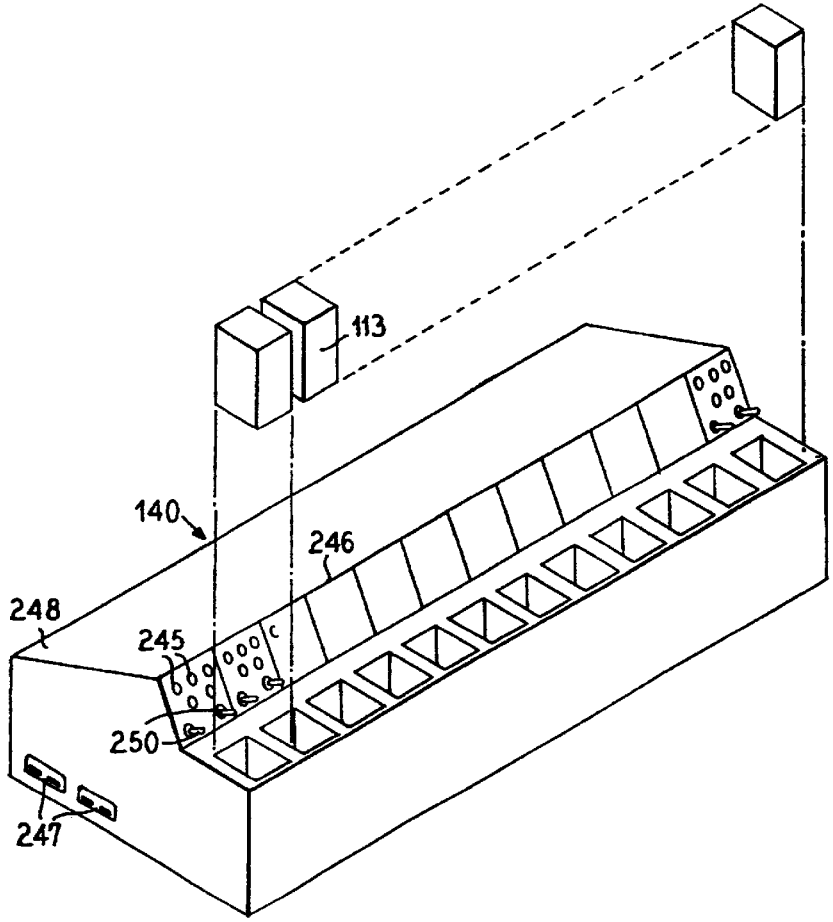

US 5,273,905 C1

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 13-20 is confirmed.

Claims 1, 2 and 4 are determined to be patentable as amended.

Claims 3 and 5-12, dependent on an amended claim, are determined to be patentable.

New claims 21-39 are added and determined to be patentable.

1. Apparatus for sequential multi-step processing of biological material mounted on a surface of a slide comprising:
    (a) a plurality of processing stations, each of said processing stations comprising:
        (1) block means defining a cavity and having fluid pathway means for inputting and removing fluid from said cavity, and
        (2) *a releasable* [holding means] *slide holder* for positioning a slide bearing said biological material adjacent said cavity to define a chamber, *wherein the slide holder comprises a cam roller or a toggle*;
    (b) a plurality of fluid supply reservoir means, each including conduit means for conducting fluid therefrom to said chamber;
    (c) valve means for selectively individually interconnecting each one of said supply reservoir means with each one of said processing stations so that fluid can flow from a selected one of said reservoirs to said pathway means of at least one of said processing stations into said chamber, including associated conduit means; and
    (d) regulatable pump means for pumping fluid from a so interconnected supply reservoir to said so interconnected pathway means; whereby material can be processed at each of said processing stations identically or variously relative to material being processed at other processing stations.

2. The apparatus for sequential, multi-step processing of biological material mounted on a surface of a slide of claim [28] *1* wherein the relationship between said slide and said [holding means] *slide holder* is such that the initial volume of said chamber is not greater than about 500 microliters.

4. The apparatus of claim 3 wherein each said gasket means is elastomeric and compressible, and the relationship between each said [holding means] *slide holder* and a slide associated therewith is such that each said chamber has a volume which can be varied by the amount of holding force applied to such slide by said [holding means] *slide holder*.

21. *Apparatus for sequential multi-step processing of biological material mounted on a surface of a slide comprising:*
    *(a) a plurality of processing stations, each of said processing stations comprising:*
        *(1) block means defining a cavity and having fluid pathway means for inputting and removing fluid from said cavity,*
        *(2) releasable holding means for positioning a slide bearing said biological material adjacent said cavity to define a chamber, and*
        *(3) a temperature regulating means, wherein the temperature of each of the processing stations is individually controllable;*
    *(b) a plurality of fluid supply reservoir means, each including conduit means for conducting fluid therefrom to said chamber;*
    *(c) valve means for selectively individually interconnecting each one of said supply reservoir means with each one of said processing stations so that fluid can flow from a selected one of said reservoirs to said pathway means of a least one of said processing stations into said chamber, including associated conduit means; and*
    *(d) regulatable pump means for pumping fluid from a so interconnected supply reservoir to said so interconnected pathway means; whereby material can be processed at each of said processing stations identically or variously relative to material being processed at other processing stations.*

22. *Apparatus for sequential multi-step processing of biological material mounted on a surface of a slide comprising:*
    *(a) a plurality of processing stations, each of said processing stations comprising:*
        *(1) block means defining a cavity and having fluid pathway means for inputting and removing fluid from said cavity, and*
        *(2) releasable holding means for positioning a slide bearing said biological material adjacent said cavity to define a chamber,*
    *wherein chamber volume of each of the processing stations is individually controllable;*
    *(b) a plurality of fluid supply reservoir means, each including conduit means for conducting fluid therefrom to said chamber;*
    *(c) valve means for selectively individually interconnecting each one of said supply reservoir means with each one of said processing stations so that fluid can flow from a selected one of said reservoirs to said pathway means of at least one of said processing stations into said chamber, including associated conduit means; and*
    *(d) regulatable pump means for pumping fluid from a so interconnected supply reservoir to said so interconnected pathway means; whereby material can be processed at each of said processing stations identically or variously relative to material being processed at other processing stations.*

23. *The apparatus of claim 21, wherein the relationship between said slide and said holding means is such that the initial volume of said chamber is not greater than about 500 microliters.*

24. *The apparatus of claim 21, wherein each said processing station further includes gasket means for making a fluid tight seal about the perimeter of said chamber.*

25. *The apparatus of claim 24, wherein each said gasket means is elastomeric and compressible, and the relationship between each said holding means and a slide associated therewith is such that each said chamber has a volume which can be varied by the amount of holding force applied to such slide by said holding means.*

26. *The apparatus of claim 21, which further includes control means for operational sequencing and regulating.*

27. *The apparatus of claim 21, wherein said block means of one of said processing station further includes*
    *a channel extending vertically therethrough from the block back face to said block interior portion, and*
    *check valve means in said channel which limits passage of fluid therethrough to one direction proceeding from said back face to said interior portion.*

28. The apparatus of claim 21, wherein each said station further includes:
   means for introducing into, and removing from, said chamber a volume of a liquid composition which is not substantially larger than the volume of said chamber, and
   liquid containment means for retaining such liquid composition so introduced into such a chamber a predeterminable length of time.

29. The apparatus of claim 21, wherein
   (e) each said station further includes:
      delivery reservoir means,
      first fluid conduit means interconnecting input portions of said pathway means with said delivery reservoir means,
      second fluid conduit means interconnecting said supply reservoir means with said valve means, and
      controllable pumping means for transferring liquid from said delivery reservoir means, through said first fluid conduit means, and through said chamber,
      so that fluid flows from a so interconnected supply reservoir through said valve means to said delivery reservoir means before passing through said chamber at each station, and
   (f) control means is provided for operating said apparatus.

30. The apparatus of claim 29, wherein at least one of said stations further includes
   recycle reservoir means,
   conduit means associating said recycle means with effluent from said removing pathways, and
   controllable switching valve means associated with said recycle reservoir means, and associated return conduit means connected to said valve means,
   so that fluid received in said recycle reservoir can be recycled from said recycle reservoir means to the originating one of said supply reservoirs.

31. The apparatus of claim 22, wherein the relationship between said slide and said holding means is such that the initial volume of said chamber is not greater than about 500 microliters.

32. The apparatus of claim 22, wherein each said processing station further includes gasket means for making a fluid tight seal about the perimeter of said chamber.

33. The apparatus of claim 32, wherein each said gasket means is elastomeric and compressible, and the relationship between each said holding means and a slide associated therewith is such that each said chamber has a volume which can be varied by the amount of holding force applied to such slide by said holding means.

34. The apparatus of claim 22, wherein each said processing station further includes termperature regulating means.

35. The apparatus of claim 22, which further includes control means for operational sequencing and regulating.

36. The apparatus of claim 22, wherein said block means of one of said processing station further includes
   a channel extending vertically therethrough from the block back face to said block interior portion, and
   check valve means in said channel which limits passage of fluid therethrough to one direction proceeding from said back face to said interior portion.

37. The apparatus of claim 22, wherein each said station further includes:
   means for introducing into, and removing from, said chamber a volume of a liquid composition which is not substantially larger than the volume of said chamber, and
   liquid containment means for retaining such liquid composition so introduced into such a chamber a predeterminable length of time.

38. The apparatus of claim 22, wherein
   (a) each said station further includes:
      delivery reservoir means,
      first fluid conduit means interconnecting input portions of said pathway means with said delivery reservoir means,
      second fluid conduit means interconnecting said supply reservoir means with said valve means, and
      controllable pumping means for transferring liquid from said delivery reservoir means, through said first fluid conduit means, and through said chamber,
      so that fluid flows from a so interconnected supply reservoir through said valve means to said delivery reservoir means before passing through said chamber at each station, and
   (b) control means is provided for operating said apparatus.

39. The apparatus of claim 38, wherein at least one of said stations further includes
   recycle reservoir means,
   conduit means associating said recycle means with effluent from said removing pathways, and
   controllable switching valve means associated with said recycle reservoir means, and associated return conduit means connected to said valve means,
   so that fluid received in said recycle reservoir can be recycled from said recycle reservoir means to the originating one of said supply reservoirs.

* * * * *